US012741145B2

(12) United States Patent
O'Connor et al.

(10) Patent No.: US 12,741,145 B2
(45) Date of Patent: Sep. 22, 2026

(54) WEARABLE DEVICES FOR TREATING SLEEP APNEA, AND ASSOCIATED SYSTEMS AND METHODS

(71) Applicant: RESTERA, INC., Santa Clara, CA (US)

(72) Inventors: Richard W. O'Connor, Atherton, CA (US); Timothy A. Fayram, Gilroy, CA (US); Dennis Potts, Scotts Valley, CA (US); Paul Paspa, Los Gatos, CA (US); Guillaume Raux, El Paso, TX (US); David Herron, Los Angeles, CA (US)

(73) Assignee: RESTERA, INC., Santa Clara, CA (US)

( * ) Notice: Subject to any disclaimer, the term of this patent is extended or adjusted under 35 U.S.C. 154(b) by 510 days.

(21) Appl. No.: 17/851,718

(22) Filed: Jun. 28, 2022

(65) Prior Publication Data

US 2022/0409897 A1 Dec. 29, 2022

Related U.S. Application Data

(60) Provisional application No. 63/216,292, filed on Jun. 29, 2021.

(51) Int. Cl.
*A61N 1/36* (2006.01)
*A61N 1/378* (2006.01)

(52) U.S. Cl.
CPC ........ *A61N 1/3611* (2013.01); *A61N 1/36171* (2013.01); *A61N 1/3787* (2013.01)

(58) Field of Classification Search
CPC ...... A61N 1/36; A61N 1/3601; A61N 1/3611; A61N 1/37; A61N 1/3787; A61B 5/6822
See application file for complete search history.

(56) References Cited

U.S. PATENT DOCUMENTS 4,365,636 A 12/1982 Barker
4,558,704 A 12/1985 Petrofsky
(Continued)

FOREIGN PATENT DOCUMENTS

CA 2477540 5/2005
CN 201361029 12/2009
(Continued)

OTHER PUBLICATIONS

Wirth et al., "Hypogloassal nerve stimulation therapy does not alter tongue protrusion strength and fatigability in obstructive sleep apnea," Journal of Clinical Sleep Medicine, vol. 16, No. 2., Feb. 2020, 8 pages.
(Continued)

*Primary Examiner* — Lynsey C Eiseman
(74) *Attorney, Agent, or Firm* — Ashurst Perkins Coie US LLP

(57) ABSTRACT

The present technology is generally directed to wearable devices for treating sleep apnea, and associated systems and methods. In some embodiments, a system for treating sleep apnea comprises an implantable device and a wearable device. The implantable device can be implantably positionable at a patient's head and/or neck, proximate to the patient's oral cavity, and include a signal generator configured to generate an electrical signal, an electrode coupled to the signal generator to direct the electrical signal to the patient's tissue, and a power receiver device coupled to the signal generator. The wearable device can include a power source and a power transmission device coupled to the power source and configured to transmit power wirelessly to the implantable device.

19 Claims, 31 Drawing Sheets

(56) References Cited

U.S. PATENT DOCUMENTS

| | | | |
|---|---|---|---|
| 4,830,008 | A | 5/1989 | Meer |
| 4,947,844 | A | 8/1990 | McDermott |
| 5,123,425 | A | 6/1992 | Shannon, Jr. et al. |
| 5,146,918 | A | 9/1992 | Kallok et al. |
| 5,190,053 | A | 3/1993 | Meer |
| 5,193,539 | A | 3/1993 | Schulman |
| 5,193,540 | A | 3/1993 | Schulman |
| 5,212,476 | A | 5/1993 | Maloney et al. |
| 5,265,624 | A | 11/1993 | Bowman |
| 5,284,161 | A | 2/1994 | Karell |
| 5,540,732 | A | 7/1996 | Testerman |
| 5,546,952 | A | 8/1996 | Erickson |
| 5,697,076 | A | 12/1997 | Troyk et al. |
| 5,792,067 | A | 8/1998 | Karell |
| 6,132,384 | A | 10/2000 | Christopherson et al. |
| 6,212,435 | B1 | 4/2001 | Lattner |
| 6,240,316 | B1 | 5/2001 | Richmond et al. |
| 6,251,126 | B1 | 6/2001 | Ottenhoff et al. |
| 6,269,269 | B1 | 7/2001 | Ottenhoff et al. |
| 6,345,202 | B2 | 2/2002 | Richmond et al. |
| 6,361,494 | B1 | 3/2002 | Lindenthaler |
| 6,582,441 | B1 | 6/2003 | He et al. |
| 6,587,725 | B1 | 7/2003 | Durand et al. |
| 6,618,627 | B2 | 9/2003 | Lattner |
| 6,636,767 | B1 | 10/2003 | Knudson |
| 7,189,204 | B2 | 3/2007 | Ni et al. |
| 7,252,640 | B2 | 8/2007 | Ni et al. |
| 7,367,935 | B2 | 5/2008 | Mechlenburg et al. |
| 7,369,896 | B2 | 5/2008 | Gesotti |
| 7,369,991 | B2 | 5/2008 | Manabe et al. |
| 7,371,220 | B1 | 5/2008 | Koh et al. |
| 7,574,357 | B1 | 8/2009 | Jorgensen et al. |
| 7,620,451 | B2 | 11/2009 | Demarais et al. |
| 7,634,315 | B2 | 12/2009 | Mashiach et al. |
| 7,660,632 | B2 | 2/2010 | Kirby et al. |
| 7,672,728 | B2 | 3/2010 | Libbus et al. |
| 7,680,538 | B2 | 3/2010 | Durand et al. |
| 7,684,858 | B2 | 3/2010 | He et al. |
| 7,711,438 | B2 | 5/2010 | Lattner et al. |
| 7,761,167 | B2 | 7/2010 | Bennett et al. |
| 7,822,480 | B2 | 10/2010 | Park et al. |
| 7,882,842 | B2 | 2/2011 | Bhat et al. |
| 7,890,193 | B2 | 2/2011 | Tingey |
| 7,920,915 | B2 | 4/2011 | Mann |
| 8,024,044 | B2 | 9/2011 | Kirby et al. |
| 8,200,486 | B1 | 6/2012 | Jorgensen et al. |
| 8,249,723 | B2 | 8/2012 | McCreery |
| 8,340,785 | B2 | 12/2012 | Bonde et al. |
| 8,359,108 | B2 | 1/2013 | McCreery |
| 8,498,712 | B2 | 7/2013 | Bolea |
| 8,574,164 | B2 | 11/2013 | Mashiach |
| 8,577,464 | B2 | 11/2013 | Mashiach |
| 8,577,478 | B2 | 11/2013 | Mashiach et al. |
| 8,585,617 | B2 | 11/2013 | Mashiach et al. |
| 8,620,438 | B1 | 12/2013 | Wijting |
| 8,655,451 | B2 | 2/2014 | Klosterman |
| 8,684,925 | B2 | 4/2014 | Manicka et al. |
| 8,688,219 | B2 | 4/2014 | Ransom |
| 8,768,474 | B1 | 7/2014 | Thompson et al. |
| 8,774,943 | B2 | 7/2014 | McCreery et al. |
| 8,812,130 | B2 | 8/2014 | Stahmann et al. |
| 8,855,767 | B2 | 10/2014 | Faltys et al. |
| 8,909,351 | B2 | 12/2014 | Dinsmoor et al. |
| 8,938,299 | B2 | 1/2015 | Christopherson et al. |
| 8,983,572 | B2 | 3/2015 | Ni |
| 8,983,611 | B2 | 3/2015 | Mokelke et al. |
| 9,031,653 | B2 | 5/2015 | Mashiach |
| 9,042,995 | B2 | 5/2015 | Dinsmoor |
| 9,061,162 | B2 | 6/2015 | Mashiach et al. |
| 9,136,728 | B2 | 9/2015 | Dinsmoor |
| 9,155,899 | B2 | 10/2015 | Mashiach et al. |
| 9,205,255 | B2 | 12/2015 | Strother |
| 9,227,053 | B2 | 1/2016 | Bonde et al. |
| 9,248,302 | B2 | 2/2016 | Mashiach et al. |
| 9,308,381 | B2 | 4/2016 | Mashiach et al. |
| 9,402,563 | B2 | 8/2016 | Thakur et al. |
| 9,409,013 | B2 | 8/2016 | Mashiach |
| 9,415,215 | B2 | 8/2016 | Mashiach |
| 9,415,223 | B2 | 8/2016 | Carbunaru et al. |
| 9,463,318 | B2 | 10/2016 | Mashiach et al. |
| 9,486,628 | B2 | 11/2016 | Christopherson et al. |
| 9,504,828 | B2 | 11/2016 | Mashiach et al. |
| 9,586,048 | B2 | 3/2017 | Ternes et al. |
| 9,643,022 | B2 | 5/2017 | Mashiach et al. |
| 9,687,664 | B2 | 6/2017 | Poon et al. |
| 9,808,620 | B2 | 11/2017 | Kent |
| 9,833,613 | B2 | 12/2017 | Sama |
| 9,839,786 | B2 | 12/2017 | Rondoni et al. |
| 9,849,289 | B2 | 12/2017 | Mashiach et al. |
| 9,855,431 | B2 | 1/2018 | Ternes |
| 9,888,864 | B2 | 2/2018 | Rondoni et al. |
| 9,889,299 | B2 | 2/2018 | Ni et al. |
| 9,895,541 | B2 | 2/2018 | Meadows et al. |
| 9,907,967 | B2 | 3/2018 | Mashiach et al. |
| 9,943,391 | B2 | 4/2018 | Chu |
| 9,950,166 | B2 | 4/2018 | Mashiach et al. |
| 10,004,896 | B2 | 6/2018 | Oron et al. |
| 10,004,913 | B2 | 6/2018 | Poon et al. |
| 10,052,097 | B2 | 8/2018 | Mashiach et al. |
| 10,058,701 | B2 | 8/2018 | Sama |
| 10,195,426 | B2 | 2/2019 | Kent |
| 10,195,427 | B2 | 2/2019 | Kent |
| 10,195,428 | B2 | 2/2019 | Scheiner |
| 10,238,872 | B2 | 3/2019 | Pivonka et al. |
| 10,314,501 | B2 | 6/2019 | Zitnik et al. |
| 10,335,596 | B2 | 7/2019 | Yakovlev et al. |
| 10,512,782 | B2 | 12/2019 | Mashiach et al. |
| 10,583,297 | B2 | 3/2020 | Ni |
| 10,594,166 | B2 | 3/2020 | Ho et al. |
| 10,716,940 | B2 | 7/2020 | Mashiach et al. |
| 10,744,339 | B2 | 8/2020 | Makansi |
| 10,751,537 | B2 | 8/2020 | Mashiach et al. |
| 10,806,926 | B2 | 10/2020 | Christopherson et al. |
| 10,827,786 | B2 | 11/2020 | Amour et al. |
| 10,828,502 | B2 | 11/2020 | Poon et al. |
| 10,898,709 | B2 | 1/2021 | Wagner et al. |
| 10,932,682 | B2 | 3/2021 | Christopherson et al. |
| 10,967,183 | B2 | 4/2021 | Yakovlev et al. |
| 10,994,139 | B2 | 5/2021 | Fayram et al. |
| 11,033,738 | B2 | 6/2021 | Steier |
| 11,090,491 | B2 | 8/2021 | Mashiach et al. |
| 11,160,980 | B2 | 11/2021 | Mashiach et al. |
| 11,253,712 | B2 | 2/2022 | Mashiach |
| 11,266,837 | B2 | 3/2022 | Scheiner et al. |
| 11,273,305 | B2 | 3/2022 | Scheiner et al. |
| 11,291,842 | B2 | 4/2022 | Caparso et al. |
| 11,298,549 | B2 | 4/2022 | Mashiach et al. |
| 11,324,950 | B2 | 5/2022 | Dieken et al. |
| 11,654,283 | B2 | 5/2023 | Tesfayesus et al. |
| 11,964,154 | B1 | 4/2024 | Raux et al. |
| 2001/0023362 | A1 | 9/2001 | Kobayashi |
| 2003/0069626 | A1 | 4/2003 | Lattner et al. |
| 2003/0078643 | A1 | 4/2003 | Schulman et al. |
| 2003/0195571 | A1 | 10/2003 | Burnes et al. |
| 2003/0199945 | A1 | 10/2003 | Ciulla |
| 2004/0073272 | A1 | 4/2004 | Knudson |
| 2004/0147975 | A1 | 7/2004 | Popovic |
| 2004/0153127 | A1 | 8/2004 | Gordon et al. |
| 2005/0038485 | A1 | 2/2005 | Ludwig |
| 2005/0043644 | A1 | 2/2005 | Stahmann et al. |
| 2005/0085874 | A1 | 4/2005 | Davis |
| 2005/0137646 | A1 | 6/2005 | Wallace |
| 2005/0261600 | A1 | 11/2005 | Aylsworth |
| 2006/0155206 | A1 | 7/2006 | Lynn |
| 2006/0224211 | A1 | 10/2006 | Durand et al. |
| 2006/0247729 | A1 | 11/2006 | Tehrani |
| 2006/0266369 | A1 | 11/2006 | Atkinson et al. |
| 2007/0112343 | A1 | 5/2007 | Mische et al. |
| 2007/0173893 | A1 | 7/2007 | Pitts |
| 2007/0270632 | A1 | 11/2007 | Nelson |
| 2007/0277836 | A1 | 12/2007 | Longley |
| 2008/0033304 | A1 | 2/2008 | Dalal |
| 2008/0103545 | A1 | 5/2008 | Bolea |
| 2008/0103769 | A1 | 5/2008 | Schultz et al. |

(56) References Cited

U.S. PATENT DOCUMENTS

| | | | |
|---|---|---|---|
| 2008/0208287 A1 | 8/2008 | Palermo | |
| 2009/0030469 A1 | 1/2009 | Meiry | |
| 2009/0118610 A1 | 5/2009 | Karmarkar et al. | |
| 2009/0221943 A1 | 9/2009 | Burbank | |
| 2010/0023103 A1 | 1/2010 | Elborno | |
| 2010/0094376 A1 | 4/2010 | Penner | |
| 2010/0094379 A1 | 4/2010 | Meadows | |
| 2010/0094398 A1 | 4/2010 | Malewicz | |
| 2010/0100153 A1 | 4/2010 | Carlson et al. | |
| 2010/0137726 A1* | 6/2010 | Matsumura | A61B 5/25 600/509 |
| 2010/0152546 A1 | 6/2010 | Behan et al. | |
| 2010/0152808 A1 | 6/2010 | Boggs, II | |
| 2010/0185254 A1 | 7/2010 | Lindquist et al. | |
| 2010/0198041 A1 | 8/2010 | Christian et al. | |
| 2010/0201500 A1 | 8/2010 | Stirling et al. | |
| 2010/0241195 A1 | 9/2010 | Meadows | |
| 2010/0280570 A1 | 11/2010 | Sturm | |
| 2011/0093032 A1 | 4/2011 | Boggs, II | |
| 2011/0093036 A1 | 4/2011 | Mashiach | |
| 2011/0112601 A1 | 5/2011 | Meadows et al. | |
| 2011/0132378 A1 | 6/2011 | Levendowski | |
| 2011/0152965 A1 | 6/2011 | Mashiach | |
| 2011/0172733 A1 | 7/2011 | Lima et al. | |
| 2011/0172743 A1 | 7/2011 | Davis et al. | |
| 2011/0213438 A1 | 9/2011 | Lima et al. | |
| 2011/0230702 A1 | 9/2011 | Honour | |
| 2011/0264164 A1 | 10/2011 | Christopherson | |
| 2011/0295083 A1 | 12/2011 | Doelling et al. | |
| 2012/0024297 A1 | 2/2012 | Hedge | |
| 2012/0029362 A1 | 2/2012 | Patangay et al. | |
| 2012/0089153 A1 | 4/2012 | Christopherson | |
| 2012/0095531 A1 | 4/2012 | Derbas et al. | |
| 2012/0192874 A1 | 8/2012 | Bolea | |
| 2012/0197340 A1 | 8/2012 | Tesfayesus | |
| 2012/0234331 A1 | 9/2012 | Totada | |
| 2012/0256585 A1 | 10/2012 | Partovi et al. | |
| 2013/0072999 A1 | 3/2013 | Mashiach | |
| 2013/0085537 A1 | 4/2013 | Mashiach | |
| 2013/0085544 A1 | 4/2013 | Mashiach | |
| 2013/0085545 A1 | 4/2013 | Mashiach | |
| 2013/0085558 A1 | 4/2013 | Mashiach | |
| 2013/0085559 A1 | 4/2013 | Mashiach | |
| 2013/0085560 A1 | 4/2013 | Mashiach | |
| 2013/0140289 A1 | 6/2013 | Barateir | |
| 2013/0261693 A1 | 10/2013 | Gross | |
| 2014/0046221 A1 | 2/2014 | Mashiach | |
| 2014/0135868 A1 | 5/2014 | Bashyam | |
| 2014/0228905 A1* | 8/2014 | Bolea | A61F 5/56 607/42 |
| 2014/0236031 A1 | 8/2014 | Banet et al. | |
| 2015/0029030 A1 | 1/2015 | Aoyama | |
| 2015/0038865 A1 | 2/2015 | Shigeto | |
| 2015/0039046 A1 | 2/2015 | Gross | |
| 2015/0057719 A1 | 2/2015 | Tang | |
| 2015/0073232 A1 | 3/2015 | Ahmed | |
| 2015/0105840 A1 | 4/2015 | Boggs, II | |
| 2015/0112697 A1 | 4/2015 | Bradley | |
| 2015/0134028 A1 | 5/2015 | Greatbatch | |
| 2015/0142120 A1 | 5/2015 | Papay | |
| 2015/0182753 A1 | 7/2015 | Harris | |
| 2015/0190630 A1 | 7/2015 | Kent et al. | |
| 2015/0206151 A1 | 7/2015 | Carney | |
| 2015/0224307 A1 | 8/2015 | Bolea | |
| 2015/0273177 A1 | 10/2015 | Lizuka | |
| 2015/0374991 A1 | 12/2015 | Morris et al. | |
| 2016/0029927 A1 | 2/2016 | Finkelstein et al. | |
| 2016/0030740 A1* | 2/2016 | Mashiach | A61N 1/37211 607/42 |
| 2016/0089540 A1 | 3/2016 | Bolea | |
| 2016/0114159 A1 | 4/2016 | Kent | |
| 2016/0235981 A1 | 8/2016 | Southwell | |
| 2016/0317160 A1 | 11/2016 | Smith et al. | |
| 2016/0317345 A1 | 11/2016 | Marie | |
| 2016/0331952 A1 | 11/2016 | Faltys | |
| 2017/0014068 A1 | 1/2017 | Gotoh et al. | |
| 2017/0087360 A1 | 3/2017 | Scheiner | |
| 2017/0095667 A1 | 4/2017 | Yakovelev et al. | |
| 2017/0135604 A1 | 5/2017 | Kent | |
| 2017/0135629 A1 | 5/2017 | Kent | |
| 2017/0143257 A1 | 5/2017 | Kent | |
| 2017/0143259 A1 | 5/2017 | Kent | |
| 2017/0143280 A1 | 5/2017 | Kent | |
| 2017/0143960 A1 | 5/2017 | Kent | |
| 2017/0151432 A1 | 6/2017 | Christopherson | |
| 2017/0224987 A1 | 8/2017 | Kent | |
| 2017/0368341 A1 | 12/2017 | Bolea | |
| 2018/0015282 A1 | 1/2018 | Waner | |
| 2018/0028824 A1 | 2/2018 | Pinvonka et al. | |
| 2018/0085593 A1 | 3/2018 | Fayram et al. | |
| 2018/0214079 A1 | 8/2018 | Banet et al. | |
| 2018/0220921 A1 | 8/2018 | Rondoni et al. | |
| 2018/0221660 A1 | 8/2018 | Suri et al. | |
| 2018/0272118 A1* | 9/2018 | Goldwasser | A61N 1/0492 |
| 2019/0001139 A1 | 1/2019 | Mishra et al. | |
| 2019/0022383 A1 | 1/2019 | Hadlock | |
| 2019/0057700 A1 | 2/2019 | Kent | |
| 2019/0060642 A1 | 2/2019 | Boggs, II et al. | |
| 2019/0099285 A1 | 4/2019 | Bachelder et al. | |
| 2019/0117967 A1 | 4/2019 | Scheiner | |
| 2019/0374776 A1 | 12/2019 | Mishra et al. | |
| 2020/0001077 A1 | 1/2020 | Kent | |
| 2020/0016401 A1 | 1/2020 | Papay et al. | |
| 2020/0038033 A1 | 2/2020 | Clark et al. | |
| 2020/0054867 A1 | 2/2020 | Schwartz et al. | |
| 2020/0054889 A1 | 2/2020 | Makansi | |
| 2020/0069947 A1 | 3/2020 | Kent | |
| 2020/0139138 A1 | 5/2020 | Sit | |
| 2020/0281763 A1 | 9/2020 | Scheiner | |
| 2020/0282219 A1 | 9/2020 | Scheiner et al. | |
| 2020/0316373 A1 | 10/2020 | Bolea | |
| 2020/0338358 A1 | 10/2020 | Makansi | |
| 2020/0346010 A1 | 11/2020 | Papay et al. | |
| 2020/0346016 A1 | 11/2020 | Caparso et al. | |
| 2020/0346024 A1 | 11/2020 | Caparso et al. | |
| 2020/0376261 A1 | 12/2020 | Stevens et al. | |
| 2021/0052888 A1 | 2/2021 | Kent | |
| 2021/0106824 A1 | 4/2021 | Caparso et al. | |
| 2021/0321939 A1 | 10/2021 | Kent | |
| 2021/0322767 A1 | 10/2021 | Kent | |
| 2022/0032052 A1 | 2/2022 | Kent et al. | |
| 2022/0126103 A1 | 4/2022 | Pivonka et al. | |
| 2022/0133222 A1 | 5/2022 | Ferreira dos Santos da Fonseca | |
| 2022/0134101 A1 | 5/2022 | Scheiner et al. | |
| 2022/0134102 A1 | 5/2022 | Kent | |
| 2022/0161031 A1 | 5/2022 | O'Connor et al. | |
| 2022/0218988 A1 | 7/2022 | Caparso et al. | |
| 2022/0233857 A1* | 7/2022 | Dassos | A61N 1/3615 |
| 2022/0339441 A1 | 10/2022 | Elliott | |
| 2022/0346666 A1 | 11/2022 | Elliott | |
| 2022/0362553 A1 | 11/2022 | Gouveris et al. | |
| 2022/0370797 A1 | 11/2022 | O'Connor | |
| 2022/0379114 A1 | 12/2022 | Kent | |
| 2022/0401728 A1 | 12/2022 | Dassos et al. | |
| 2023/0026728 A1 | 1/2023 | Elliott | |
| 2023/0172479 A1 | 6/2023 | Verzal | |
| 2023/0240715 A1 | 8/2023 | Paspa et al. | |
| 2023/0302280 A1 | 9/2023 | O'Connor | |
| 2023/0321440 A1 | 10/2023 | O'Connor | |
| 2023/0414945 A1 | 12/2023 | Ward | |
| 2024/0307697 A1 | 9/2024 | Mullins et al. | |

FOREIGN PATENT DOCUMENTS

| | | | |
|---|---|---|---|
| EP | 1128868 | 3/2010 | |
| JP | 2007202939 A * | 8/2007 | A61B 5/6822 |
| JP | 2011-500143 | 1/2011 | |
| JP | 2012521864 A | 9/2012 | |
| JP | 2013509943 A | 3/2013 | |
| JP | 2014-521403 | 8/2014 | |
| JP | 2014158607 | 9/2014 | |
| JP | 2018-504243 | 2/2018 | |
| JP | 2019503722 A | 2/2019 | |
| JP | 2019-506960 | 3/2019 | |

(56) References Cited

FOREIGN PATENT DOCUMENTS

| | | | |
|---|---|---|---|
| KR | 20060087852 | 8/2006 | |
| KR | 10-2019-0049502 | 5/2019 | |
| KR | 2020-0091279 | 7/2020 | |
| WO | WO-9720522 | 6/1997 | |
| WO | WO-2008100779 | 8/2008 | |
| WO | 2009048580 | 4/2009 | |
| WO | WO-2010006218 | 1/2010 | |
| WO | WO-2012027648 | 3/2012 | |
| WO | 2013009371 | 1/2013 | |
| WO | WO-2013172935 | 11/2013 | |
| WO | 2016124739 | 8/2016 | |
| WO | WO-2017070372 | 4/2017 | |
| WO | 2017149436 | 9/2017 | |
| WO | 2017178694 | 10/2017 | |
| WO | 2018126062 A1 | 7/2018 | |
| WO | WO-2019140404 | 7/2019 | |
| WO | 2020153561 | 7/2020 | |
| WO | 2020185549 A1 | 9/2020 | |
| WO | WO-2020181120 | 9/2020 | |
| WO | 2020240480 | 12/2020 | |
| WO | WO-2020240480 A1 * | 12/2020 | ........... A61B 5/0205 |
| WO | WO-2021050829 | 3/2021 | |
| WO | WO-2021163228 | 8/2021 | |
| WO | WO-2021216724 | 10/2021 | |
| WO | WO-2021242633 | 12/2021 | |
| WO | WO-2022058024 | 3/2022 | |
| WO | 2022098786 | 5/2022 | |
| WO | WO-2022129234 | 6/2022 | |
| WO | WO-2022129236 | 6/2022 | |
| WO | WO-2022129247 | 6/2022 | |
| WO | 2022246320 | 11/2022 | |
| WO | 2023169955 | 9/2023 | |
| WO | 2023247333 | 12/2023 | |

OTHER PUBLICATIONS

Atkinson, Martin, "Anatomy for Dental Students," OUP Oxford Fourth Edition, Mar. 14, 2013, p. 298.
Caycedo et al., "Electromyographic Analysis for Silent Speech Detection," ARPN Journal of Engineering and Applied Sciences, vol. 12, No. 1 Jan. 2017, 8 pages.
Janke et al., "A Spectral Mapping Method for EMG-based Recognition of Silent Speech," In B-Interface, 2010, 10 pages.
Weaker, Frank, "Structures of the Head and Neck," F.A. Davis, Sep. 24, 2013, p. 77.
Website: CawBing: Snore Stopper Adjustable Snore Reduction Straps Anti Apnea Snore Support Belt Jaw Sleep Band Snoring Chin Strap, https://www.walmart.com/ip/Snore-Stopper-Adjustable-Snore-Reduction-Straps-Anti-Apnea-Snore-Support-Belt-Jaw-Sleep-Band-Snoring-Chin-Strap/788742945, accessed Jun. 2022, 5 pages.
Website: Halo Chinstrap by Breathwear Inc., https://www.cpap.com/productpage/breathewear-halo-chinstrap, accessed Jun. 2022, 3 pages.
International Search Report and Written Opinion for International Patent Application No. PCT/US22/35281, Applicant: Invicta Medical, Inc., mailed Nov. 18, 2022, 18 pages.
Kent et al., "Ultrasound Localization and Percutaneous Electrical Stimulation of the Hypoglossal Nerve and Ansa Cervivalis," Otolaryngology Head and Neck Surgery, 2020, 7 pages.
Benbassat et al., "The specific branches leading to the genioglossus muscle: three dimensional localisation using skin reference points," Surgical and Radiologic Anatomy, 2019, 9 pages.
Delaey et al., "Specific branches of hypoglossal nerve to genioglossus muscle as a potential target of selective neurostimulation in obstructive sleep apnea: anatomical and morphometric study," Surg Radiol Anata, 2017, 9 pages.
Gharb et al., "Microsurgical Anatomy of the Terminal Hypoglossal Nerve Relevant for Neurostimulation in Obstructive Sleep Apnea," Neuromodulation: Technology at the Neural Interface, 2015, 8 pages.
Heiser et al., "Surgical anatomy of the hypoglossal nerve: A new classification system for selective upper airway stimulation," Wiley Periodicals, Inc., wileyonlinelibrary.com/journal/hed, 2017, 10 pages.
Li et al., "Dynamic Drug-Induced Sleep Computed Tomography in Adults with Obstructive Sleep Apnea," Scientific Reports—www.nature.com/scientificreports, Oct. 2016, 8 pages.
Mu et al., "Human Tongue Neuroanatomy: Nerve Supply and Motor Endplates," National Institute of Health, 2012, 27 pages.
Pearse et al., "Review: Sleep-Disordered Breathing in Heart Failure," Imperial College London and Royal Brompton Hospital, London, United Kingdom, https://onlinelibrary.wiley.com/doi/full/10.1002/ejhf.492, published Feb. 11, 2016, 26 pages.
Vroegop et al., "Sleep endoscopy with simulation bite for prediction of oral appliance treatment outcome," Obstructive Sleep Apnea, European Sleep Research Society, 2012, 8 pages.
U.S. Appl. No. 18/331,109, filed Jun. 7, 2023, Raux et al.
"Muscular System: Genioglossus Muscle," Elsevier, https://www.elsevier.com/resources/anatomy/muscular-system/muscles-of-head/genioglossus-muscle/17818, 2016, 4 pages.
Extended European Search Report for European Patent Application No. 22834048.5, Applicant: Invicta Medical, Inc., mailed May 30, 2025, 9 pages.

* cited by examiner

WEARABLE DEVICES FOR TREATING SLEEP APNEA, AND ASSOCIATED SYSTEMS AND METHODS

CROSS-REFERENCE TO RELATED APPLICATION

The present application claims priority to U.S. Provisional App. No. 63/216,292, filed Jun. 29, 2021, the entirety of which is incorporated herein by reference.

TECHNICAL FIELD

The present technology is directed to wearable devices for treating sleep apnea, and associated systems and methods. Representative devices include collars, chin straps, pillows and/or other wearables that provide power transcutaneously to minimally invasive implanted power converters, signal generators, and/or electrodes.

BACKGROUND

Obstructive sleep apnea (OSA) is a medical condition in which a patient's upper airway is occluded (partially or fully) during sleep, causing sleep arousal. Repeated occlusions of the upper airway may cause sleep fragmentation, which in turn may result in sleep deprivation, daytime tiredness, and/or malaise. More serious instances of OSA may increase the patient's risk for stroke, cardiac arrhythmias, high blood pressure, and/or other disorders.

OSA may be characterized by the tendency for soft tissues of the upper airway to collapse during sleep, thereby occluding the upper airway. OSA is typically caused by the collapse of the patient's soft palate, oropharynx, tongue, epiglottis, or combination thereof, into the upper airway, which in turn may obstruct normal breathing and/or cause arousal from sleep.

Some treatments have been available for OSA including, for example, surgery, constant positive airway pressure (CPAP) machines, and electrically stimulating muscles or related nerves associated with the upper airway to move the tongue (or other upper airway tissue). Surgical techniques have included procedures to remove portions of a patient's tongue and/or soft palate, and other procedures that seek to prevent the tongue from collapsing into the back of the pharynx. These surgical techniques are very invasive. CPAP machines seek to maintain upper airway patency by applying positive air pressure at the patient's nose and mouth. However, these machines are uncomfortable, cumbersome, and may have low compliance rates.

Some electrical stimulation techniques seek to prevent the tongue from collapsing into the back of the pharynx by causing the tongue to protrude forward (e.g., in an anterior direction) and/or flatten during sleep. However, existing techniques for electrically stimulating the nerves of the patient's oral cavity suffer from being too invasive, and/or not sufficiently efficacious. Thus, there is a need for an improved minimally-invasive treatment for OSA and other sleep disorders.

DETAILED DESCRIPTION

Figure 1:
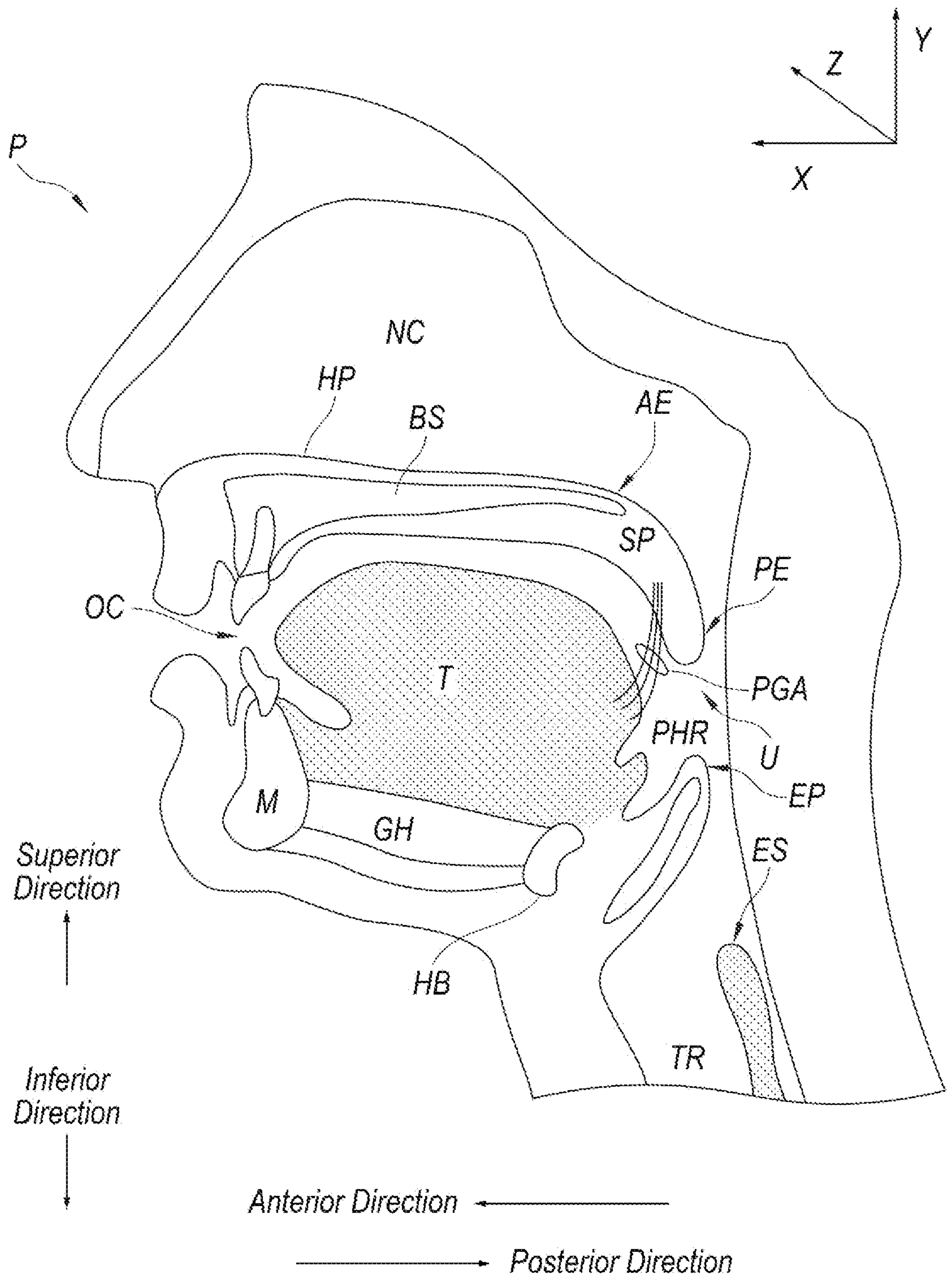
FIG. 1 is a side sectional view depicting a patient's upper airway.

The present technology is discussed under the following headings for ease of readability:

Heading 1: "Introduction"

Heading 2: "Overall Patient Physiology" (with a focus on FIGS. 1-3)

Heading 3: "Overall System" (with a focus on FIG. 4)

Heading 4: "Representative Implantable Devices" (with a focus on FIGS. 5A-5C)

Heading 5: "Representative Stimulation Targets and Implantation Techniques" (with a focus on FIGS. 6A-8B)

Heading 6: "Representative Wearable Devices" (with a focus on FIGS. 9-21)

Heading 7: "Representative Waveforms" (with a focus on FIGS. 22A-24C)

While embodiments of the present technology are described under the selected headings indicated above, other embodiments of the technology can include elements discussed under multiple headings. Accordingly, the fact that an embodiment may be discussed under a particular heading does not necessarily limit that embodiment to only the elements discussed under that heading.

1. Introduction

Electrical stimulation for obstructive sleep apnea (OSA) typically includes delivering an electrical current that modulates nerves and/or muscles, e.g., to cause the tongue and/or other soft tissue to move. The electrical stimulation can accordingly remove an obstruction of the upper airway, and/or prevent the tongue or other soft tissue from collapsing or obstructing the airway. As used herein, the terms "modulate" and "stimulate" are used interchangeably to mean having an effect on, e.g., an effect on a nerve and/or a muscle that in turn has an effect on one or more motor functions, e.g., a breathing-related motor function.

Representative methods and apparatuses for reducing the occurrence and/or severity of a breathing disorder, such as OSA, OSA with complete concentric collapse ("CCC"), central sleep apnea, and/or the like, are disclosed herein. In accordance with representative embodiments, a minimally-invasive signal delivery device is implanted proximate to or adjacent to nerves that innervate the patient's oral cavity, soft palate, oropharynx, and/or epiglottis. Representative nerves include the hypoglossal nerve, branches of the ansa cervicalis, and/or the vagus nerves, which are located adjacent and/or around the oral cavity or in the neck. The signal delivery device can be implanted in the patient via a percutaneous injection. A non-implanted power source, e.g., including one or more mouthpiece portions, collar portions, chinstrap portions, pillow portions, mattress overlay portions, other suitable "wearables," and/or one or more adhesive, skin-mounted devices, can wirelessly provide electrical power to the implanted signal delivery device. The signal delivery device emits accurately targeted electrical signals (e.g., pulses) that improve the patient's upper airway patency and/or improve the tone of the tissue of the intraoral cavity to treat sleep apnea. The electrical current delivered by the signal delivery device can stimulate at least a portion of a patient's hypoglossal nerve and/or other nerves associated with the upper airway. By moving the tongue forward and/or by preventing the tongue and/or soft tissue from collapsing onto the back of the patient's pharynx and/or into the upper airway, the devices and associated methods disclosed herein can in turn improve the patient's sleep, e.g., by moving the potentially obstructing tissue in the upper airway/pharynx down. More specifically, applying the electrical signal to the medial branch of the hypoglossal nerve can cause the tongue to move forward (anteriorly), and applying the electrical signal to the ansa cervicalis can cause the hyoid bone, the thyroid (e.g., the thyroid cartilage), and/or the larynx to move downward (inferiorly or caudally), a motion typically referred to as caudal traction.

Many embodiments of the technology described below may take the form of computer- or machine- or controller-executable instructions, including routines executed by a programmable computer or controller. Those skilled in the relevant art will appreciate that the technology can be practiced on computer/controller systems other than those shown and described below. The technology can be embodied in a special-purpose computer, controller or data processor that is specifically programmed, configured or constructed to perform one or more of the computer-executable instructions described below. Accordingly, the terms "computer" and "controller" as generally used herein refer to any suitable data processor and can include Internet appliances and hand-held devices (including palm-top computers, wearable computers, tablets, cellular or mobile phones, multi-processor systems, processor-based or programmable consumer electronics, network computers, minicomputers and the like). Information handled by these computers can be presented at any suitable display medium, including a liquid crystal display (LCD).

The present technology can also be practiced in distributed environments, where tasks or modules are performed by remote processing devices that are linked through a communications network. In a distributed computing environment, program modules or subroutines may be located in local and remote memory storage devices. Aspects of the technology described below may be stored or distributed on any suitable computer-readable media, including one or more ASICs, (e.g., with addressable memory), as well as distributed electronically over networks. Data structures and transmissions of data particular to aspects of the technology are also encompassed within the scope of the embodiments of the technology.

2. Overall Patient Physiology

Representative embodiments described herein include signal delivery devices having electrodes that can be positioned to deliver one or more electrical currents to one or more specific target locations, e.g., specific nerves and/or specific positions along a nerve. FIG. 1 illustrates the general anatomy of the patient's oral cavity, and later Figures illustrate specific target locations. Such locations include locations along the patient's hypoglossal nerve, branches of the ansa cervicalis, and/or vagus nerves, as well as those nerves that innervate muscles of airway (e.g., palatal, oropharyngeal, laryngeal, omohyoid, sternohyoid, and/or sternothyroid muscles) besides the tongue. The target location can be identified with respect to any of, or any combination of, intrinsic or extrinsic muscles, associated nerve branches and/or portions thereof, and/or other physiological features. Such a target location and/or position can also be distal from the salivary glands (e.g., medial to the sublingual salivary gland) and/or other structures to avoid causing pain and/or other undesired effects.

FIG. 1 illustrates a patient P relative to a coordinate system in which the x-axis denotes the anterior-posterior directions, the y-axis denotes the superior-inferior directions, and the z-axis denotes the medial-lateral directions. The patient P has a hard palate HP which overlies the tongue T and forms the roof of the oral cavity OC (e.g., the mouth). The hard palate HP includes bone support BS, and thus does not typically deform during breathing. The soft palate SP, which is made of soft tissue such as membranes, fibrous material, fatty tissue, and muscle tissue, extends rearward (e.g., in a posterior direction) from the hard palate HP toward the back of the pharynx PHR. More specifically, an anterior end AE of the soft palate SP is anchored to a posterior end of the hard palate HP, and a posterior end PE of the soft palate SP is unattached. Because the soft palate SP does not contain bone or hard cartilage, the soft palate SP is flexible and may collapse onto the back of the pharynx PHR and/or flap back and forth (e.g., especially during sleep).

The pharynx PHR, which passes air from the oral cavity OC and the nasal cavity NC into the trachea TR, is the part of the throat situated inferior to (below) the nasal cavity NC, posterior to (behind) the oral cavity OC, and superior to (above) the esophagus ES. The pharynx PHR is separated from the oral cavity OC by the palatoglossal arch PGA, which runs downward on either side to the base of the tongue T. Although not shown for simplicity, the pharynx PHR includes the nasopharynx, the oropharynx, and the laryngopharynx. The nasopharynx lies between an upper surface of the soft palate SP and the wall of the throat (i.e., superior to the oral cavity OC). The oropharynx lies behind the oral cavity OC and extends from the uvula U to the level of the hyoid bone HB. The oropharynx opens anteriorly into the oral cavity OC. The lateral wall of the oropharynx includes the palatine tonsil and lies between the palatoglossal arch PGA and the palatopharyngeal arch. The anterior wall of the oropharynx includes the base of the tongue T and the epiglottic vallecula. The superior wall of the oropharynx includes the inferior surface of the soft palate SP and the uvula U. Because both food and air pass through the pharynx PHR, a flap of connective tissue called the epiglottis EP closes over the glottis (not shown for simplicity) when food is swallowed, to prevent aspiration. The laryngopharynx is the part of the throat that connects to the esophagus ES, and lies inferior to the epiglottis EP. Below the tongue T is the lower jaw or mandible M, and the geniohyoid muscle GH, which is one of the muscles that controls the movement of the tongue T. The genioglossus muscle, which also controls tongue movement, and is a particular target of the presently disclosed therapy, is discussed later with reference to FIG. 4.

Figure 2:
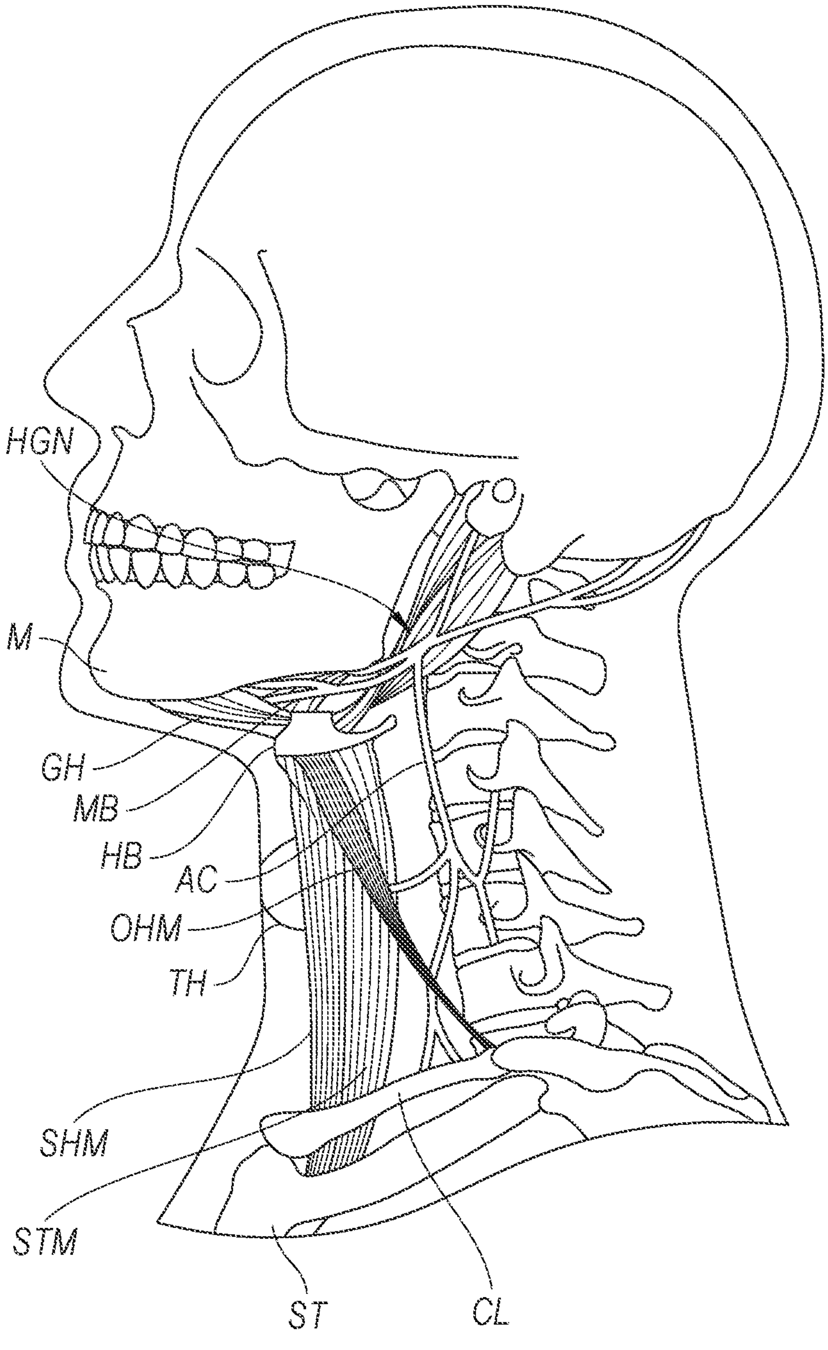
FIG. 2 is another partially schematic, side sectional view of a patient's upper airway.

FIG. 2 is a partially schematic illustration of representative neural structures and musculature of the patient's upper airway. Representative musculature includes the geniohyoid muscle GH which extends between the patient's mandible M and the hyoid bone HB. The omohyoid muscle OHM extends between the hyoid bone HB and the clavicle CL. The sternohyoid muscle SHM extends between the hyoid bone HB and the sternum ST, and the sternothyroid muscle STM extends between the clavicle CL and the patient's thyroid cartilage TH. The associated neural structures include the medial branch MB of the hypoglossal nerve HGN, which enervates the tongue, genioglossus muscle (shown in FIG. 4), and geniohyoid muscle GH. The ansa cervicalis AC, and related branches emanating from the ansa cervicalis AC, enervate the omohyoid muscle OHM, the sternohyoid muscle SHM, and the sternothyroid muscle STM. By positioning and activating minimally invasive electrodes positioned proximate to the foregoing neural structures and/or associated musculature, embodiments of the present technology can control, reduce, and/or eliminate the effects of OSA.

Figure 3:
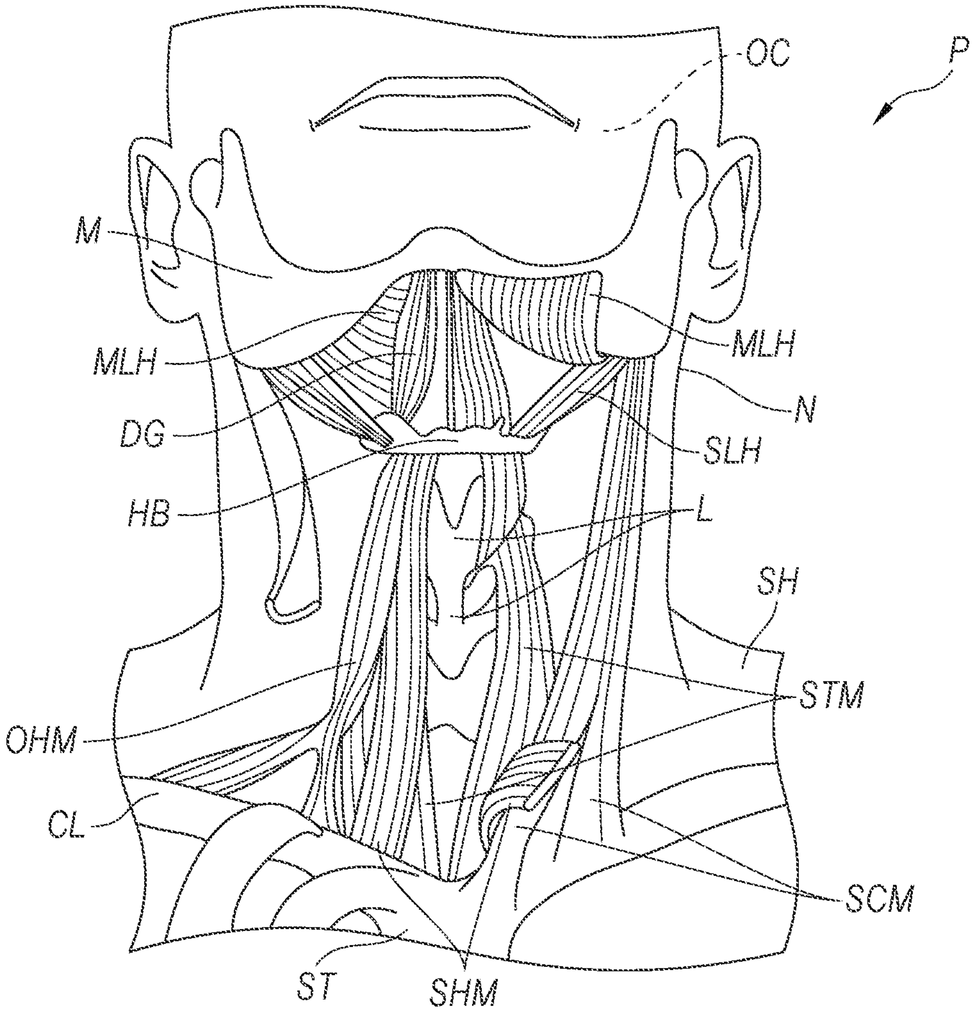
FIG. 3 is a partially schematic front view of the musculature of the patient's upper airway.

FIG. 3 is a front view of the patient P, illustrating several of the anatomic structures described above with reference to FIGS. 1 and 2. In particular, FIG. 3 illustrates the patient's mandible M, mylohyoid muscle MLH, digastric muscle DG, and the stylohyoid muscle SLH, as well as the sternothyroid muscle STM, sternocleidomastoid muscle SCM, and the sternohyoid muscle SHM. FIG. 3 also illustrates the larynx L, the patient's sternum ST, and clavicle CL. The muscles described above are contained within the patient's oral cavity OC, neck N, and/or shoulder SH, any of which may support wearable devices in accordance with the present technology.

3. Overall System

Figure 4:
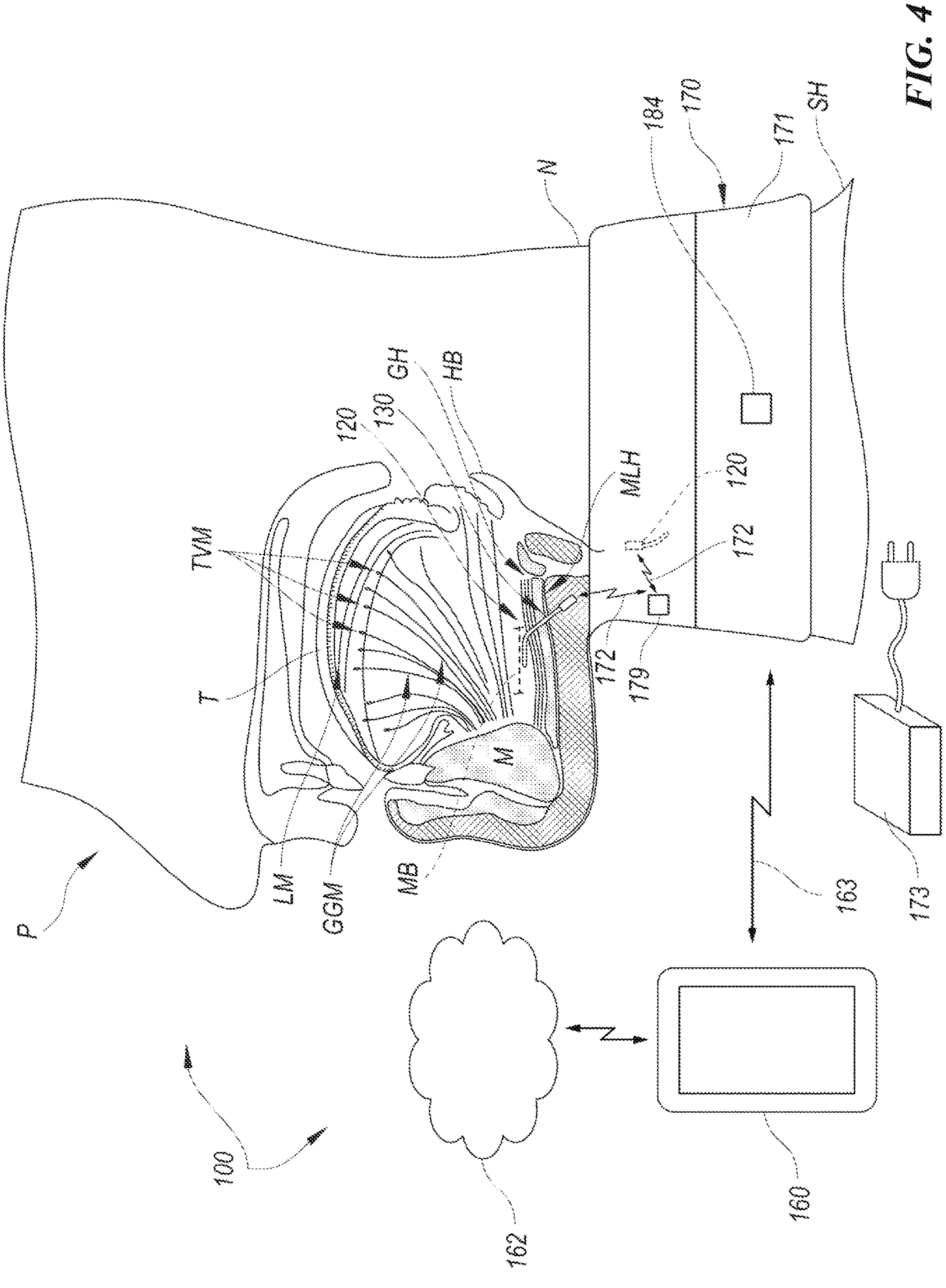
FIG. 4 is a partially schematic side-view of the patient's upper airway, including a system having a wearable device for addressing sleep apnea, in accordance with embodiments of the present technology.

FIG. 4 is a partially schematic illustration (not to scale) of a representative system 100 configured to provide electrical stimulation to the patient P in accordance with embodiments of the present technology. The musculature of the patient's oral cavity shown in FIG. 4 includes the geniohyoid muscle GH, the genioglossus muscle GGM, and the longitudinal muscle LM and transverse muscle TVM, which are part of the patient's tongue T. FIG. 4 also illustrates a portion of the median branch MB of the patient's hypoglossal nerve.

In a representative embodiment, the system 100 includes both implanted elements and external elements. The implanted elements can include one or more implantable devices 120. In the illustrated embodiment, two implanted devices 120 are shown, one positioned proximate to the median branch MB, and one positioned proximate to the ansa cervicalis AC. Each implantable device 120 can include a signal delivery device 130 positioned adjacent to the target neural and/or muscle structure. The signal delivery device 130 can be secured in place with one or more anchors, suture threads, and/or other devices. The signal delivery device 130 is operatively coupled to a signal generator. In some embodiments, all the signal generation functions are performed by the implantable device 120, and in other embodiments, some signal generation functions may be performed by external elements. The signal generation functions and signal delivery functions may be performed by a single implantable device, or multiple devices.

The implantable device(s) 120 receive power from a wearable device 170. The wearable device 170 can be configured to be worn and/or supported on, around, and/or about at least a portion of the patient's P anatomy. In a representative embodiment shown in FIG. 4, the wearable device 170 includes a collar 171 positioned around the patient's neck N and above the patient's shoulders SH. The collar 171 can support, among other elements, a power source 184, which supplies electrical power to the implantable device(s) 120, via one or more power transmission devices 179 and corresponding power transmission links 172. For purposes of illustration, a single planar power transmission device 179 is shown in FIG. 4. However, as will be described further under Heading 6, the collar 171 can include multiple power transmission devices, individual ones of which can conform to the shape of the collar 171 and/or the wearable device 170 as it is worn by the patient and can be configured to transmit power (e.g., wirelessly) to one or more of the implantable devices 120. For example, a single power transmission device 179 can be configured to transmit power to at least one, two, three, four, or all implantable devices 120. Alternatively, the collar 171 can include multiple power transmission devices, and each one of the power transmission devices 179 can be configured to transmit power to some subset of the one or more implantable devices 120.

Elements carried by the wearable device 170, and (directly or indirectly) the implantable devices 120, can be controlled by a programmer or a controller 160, via a wireless communication link 163. In addition, the programmer 160 can communicate with the cloud 162 and/or other computer services to upload data received from the patient P, and/or download information to the wearable device 170 and/or the implantable devices 120. Downloaded data can include instructions and/or other data regarding suitable treatments (e.g., from other similarly-situated patients), updates for software executed on the circuitry carried by the wearable device 170 and/or the implantable devices 120, and/or other useful information. In other embodiments, the implantable devices 120 and/or the wearable device 170 include state machine components, which are not updatable. Representative downloaded data received from the patient can include respiratory rate, heart rate, audio signals (corresponding to audible snoring, hypopnea events, and/or apnea events), body temperature, head orientation/position, saturated blood oxygen levels, air flow levels, thyroid movement, and/or tongue movement, among others. The wearable device 170 and/or the programmer 160 can receive and/or analyze these data, whether or not any of the implantable devices 120 have been implanted in the patient P. For example, prior to implantation of the implantable device(s) 120, the patient P can wear the wearable device 170 (e.g., during sleep) to collect data associated with the patient's sleep and/or sleep disorder. These data can be at least generally similar or identical to the data collected during a sleep study, such as a polysomnography ("PSG") procedure and/or a drug-induced sleep endoscopy ("DISE") procedure. The data can be uploaded to the patient's medical records and/or medical treatment history (e.g., via the cloud 162) and/or used (e.g., by a practitioner and/or the programmer 160) to (i) determine whether and/or to what extent the patient's sleep disorder could be treated by implantation of one or more of the implantable devices 120, and/or (ii) develop a sleep disorder treatment plan including one or more of the implantable devices 120.

Additionally or alternatively, after the one or more implantable devices 120 have been implanted, the wearable 170 can collect (e.g., continue to collect) data associated with the patient's sleep and/or sleep disorder, for example, to provide information (e.g., for practitioners and/or the programmer 160) for use when treating the patient's sleep disorder. For example, between and/or during therapy sessions, and based at least partially on the data collected by the wearable device 170, the programmer 160 can automatically adjust and/or optimize one or more parameters of the electrical signal delivered to the patient P (e.g., in response to a change in the patient's sleep state and/or the onset of an apneic event), and/or the programmer 160 can receive one or more adjusted/optimized signal delivery parameters (e.g., via the cloud 162). Continuing to collect such data over time (e.g., before and after implantation of one or more of the implantable devices 120) can further improve the extent to which the signal delivery parameter(s) of the therapy signal(s) can be customized and/or responsive to address the patient's P particular sleeping disorder(s). Suitable sensors for collecting such data will be described later herein. In any of the foregoing embodiments, the wearable device 170 transmits power to the implantable devices 120 via the power transmission links 172, and receives power (e.g., on an intermittent basis) from a charger 173. The charger 173 can accordingly include a conventional inductive coupling arrangement (e.g., Qi standard charging) and/or a conventional wired connection.

Further details of implantable devices are described below with reference to FIGS. 5A-5C. Further details of suitable wearable devices for powering the implantable devices, including wearable devices having a collar form factor of the type shown in FIG. 4, are described below with reference to FIGS. 9-21.

4. Representative Implantable Devices

Figure 5A:
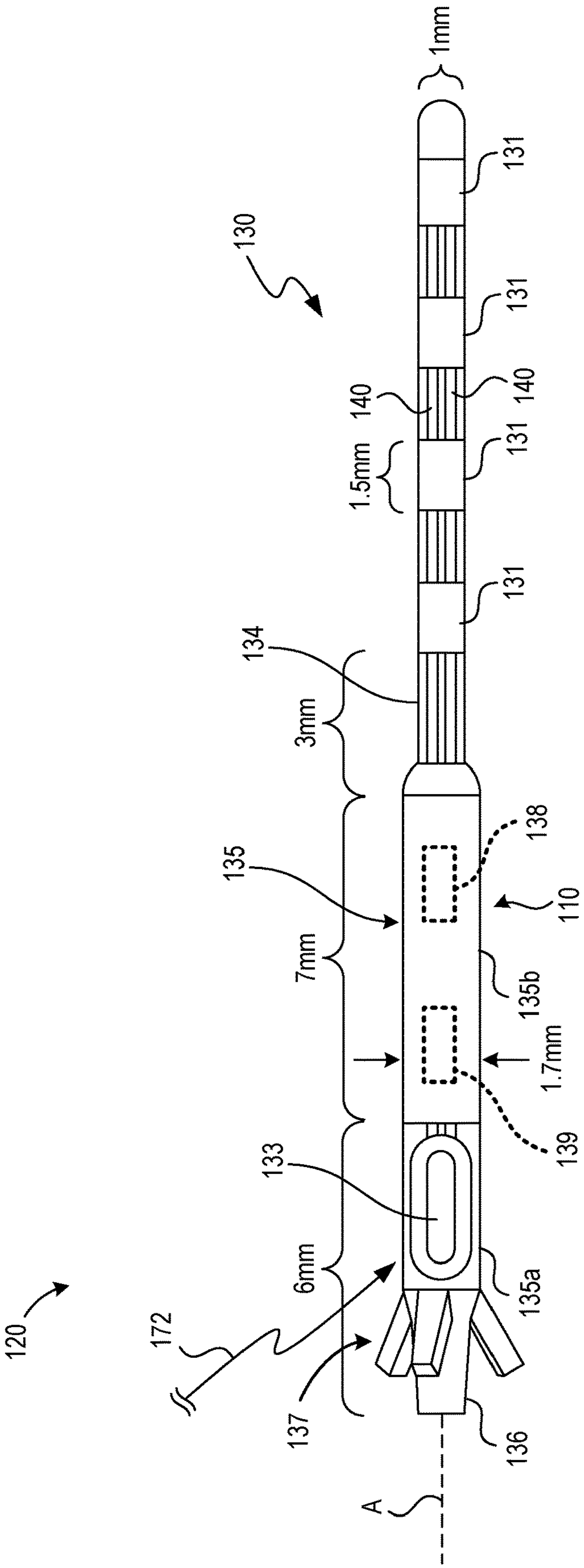
FIGS. 5A-5C are partially schematic illustrations of implantable devices configured in accordance with embodiments of the present technology.

FIG. 5A is a partially schematic side view of an implantable device 120 having elements configured in accordance with representative embodiments of the present technology. In an embodiment shown in FIG. 5A, a single implantable device 120 performs both signal generation functions and signal delivery functions. Accordingly, the implantable device 120 includes both the implantable signal delivery device 130, and an implantable signal generator 110. Representative dimensions are indicated in FIG. 5A to provide a sense of scale, but the technology is not limited to these dimensions unless expressly stated. The signal delivery device 130 includes a lead body 134, which can be generally flexible, and can carry one or more electrodes 131, which are generally rigid in some embodiments, and may be flexible in others. Flexible electrodes can increase the flexibility of the lead body 134 generally to accommodate the tortuous anatomy/insertion path near the target nerve. For purposes of illustration, the lead body 134 is shown as carrying four electrodes 131 in FIG. 5A, but in other embodiments, the lead body 134 can carry other suitable numbers of electrodes, for example, two electrodes 131. The electrodes 131 can be arranged in an array, for example, a one-dimensional linear array. The electrodes 131 can include conventional ring-shaped, or cylindrical electrodes, manufactured from a suitable, bio-compatible material, such as platinum/iridium, stainless steel, MP35N and/or other suitable conductive implant materials. The electrodes 131 can each be connected to an individual conductor 140, for example, a thin wire filament, that extends through the lead body 134. Each electrode 131 can have a length of approximately 1.5 mm as shown in FIG. 5A, or another suitable length in other embodiments. In particular embodiments, portions of the electrode(s) may be circumferentially masked to more precisely target the electrical field in a clockwise or counter-clockwise direction around the longitudinal axis A of the lead body 134.

In the embodiment illustrated in FIG. 5A, the lead body 134 is connected to, and carried by, a housing 135, which in turn carries the signal generator 110 and circuit elements for receiving power. For example, the overall housing 135 can include an antenna housing or housing portion **135*a* and a circuit housing or housing portion 135*b*. The antenna housing 135*a* may be flexible, and can carry a receiver antenna 133 (or other suitable power reception device), which receives power from the wearable device 170 (FIG. 4) via the wireless transmission link 172. The circuit housing 135*b*** can have the form of a generally cylindrical metallic "can"

formed from titanium, platinum, a platinum-iridium alloy, a ceramic, and/or another suitable material, and/or a combination thereof. The signal generator 110 can include a charge pump and/or DC-DC converter 139 and/or circuitry 138 (e.g., second circuitry) coupled to the receiver antenna 133. In some embodiments, the receiver antenna 133 can be coupled to an AC-DC convertor configured to convert the received power signal (e.g., via the wireless transmission link 172, shown in FIG. 4) to DC current. The circuitry 138 can include an ASIC, which can in turn include corresponding machine-readable instructions. The instructions can be updated wirelessly, using the electrode receiver antenna 133 for data transfer in addition to power transfer. For example, data can be transferred using pulse-width modulation (PWM) and/or other suitable techniques. Data can also be transferred in the opposite direction, e.g., using backscatter and/or other suitable techniques. For example, the implantable device 120 can transmit a receipt to indicate that power has been received, and what magnitude the power is. This information can be used to autoregulate (up or down) the output of the signal generator 110, e.g., the transmitted signal and phase. Accordingly, the circuitry 138 can include a processor and memory, including pre-programmed and updatable instructions (e.g., in the form of an ASIC) for delivering therapy signals to the patient. For example, the system can include boot loader embedded firmware. Furthermore, the overall system can use RFID-type power transmission authorization to discriminate between multiple implantable devices, which may be powered by a wearable device 170, as described above with reference to FIG. 4. RFID and/or other techniques can be used to implement security measures, e.g., to ensure that no foreign or unintended stimulation occurs. Such techniques can be implemented with suitable hardware/software carried by the implantable device 120, in at least some embodiments.

The overall housing 135 can further include a base 136, which is generally rigid, and one or more anchors 137. The anchor(s) 137 can be used in addition to or in lieu of the suture threads shown in FIG. 4 to securely position the implantable device 120 relative to the patient's tissue. In a representative embodiment, the anchor 137 includes one or more tines that extend outwardly and into the patient's tissue when the implantable device 120 is injected or otherwise implanted in the patient. Suitable techniques for implanting the signal delivery device are included in pending U.S. application Ser. No. 17/749,025, filed on May 19, 2022, the entirety of which is incorporated herein by reference. In other embodiments, the implantable device 120 can include other suitable anchors, and/or anchoring may occur at the distal and/or mid-section of the signal delivery device 130. Other suitable anchors include but are not limited to: (a) a bow spring that runs the longitudinal length of the electrode array and bows out to create fixation friction when the introducer sheath is withdrawn; (b) a small wire on a spring-loaded hinge that runs the longitudinal length of the electrodes array and bows out to create fixation friction when the introducer sheath is withdrawn; (c) a cam that, when rotated, expands in diameter to create frictional fixation when the corresponding push rod is rotated by the implanter; and/or (d) a torsion spring that, when rotated, expands in diameter to create frictional fixation when the push rod is rotated by the implanter.

Other suitable anchoring techniques include bending or deforming the lead body 134 so that it is biased into contact with the walls of the channel formed by the insertion needle. The lead body can have a bend that is straightened out during insertion (e.g., via a stylet, or by virtue of being constrained within introducer or cannula), but which reforms and produces an anchoring force when the constraint is removed. In still a further technique, the distal end of the lead body 134 is buckled (in an axial or columnar direction) once at the target location. The buckling action locally expands the diameter of the lead body so as to expand it against the tissue in which it is placed. For instances in which the device is implanted temporarily, the stylet used to introduce the device can include a bend or kink.

Yet further techniques for securing the lead body and/or other implantable element include using a mesh. For example, a plug or mesh can be inserted over at least a portion of an already deployed lead body to improve anchoring. Accordingly, the plug or mesh is not integral with the lead body 134 when the lead body is injected but is instead added to secure the lead body after the lead body is in place. The plug or mesh can be expanded radially in the manner of a suture sleeve to secure the lead body 134 against the adjacent tissue. The plug or mesh can be applied as a temporary anchor or it can for the basis for a chronic anchor. Like the other elements described above, the plug or mesh can be delivered via injection.

In at least some instances, the plug or mesh described above can have acute as well as (or in lieu of) long term or chronic applications. For example, if the practitioner induces a hemorrhage or a subsequent infection occurs, the plug/mesh can be used to manage or minimize negative sequalae, e.g., by stopping a hemorrhage.

In operation, the receiver antenna 133 receives power wirelessly from the power source 184 (FIG. 4) carried by the associated wearable device 170. In at least some embodiments, the power received at the receiver antenna 133 is in a range, for example, a radio frequency in a range of from about 300 MHz to about 6 GHz, e.g., from about 400 MHz to about 2.5 GHz, from about 600 MHz to about 2.45 GHz, from about 900 MHz to about 1.2 GHz, or any other frequency or frequency range therebetween. At this frequency, the useable range of the wireless power transmission link 172 is about 10 cm, more than enough to cover the distance between the implanted signal delivery device 130 and the wearable device 170. At this range, the power transmission process is not expected to cause tissue heating, and accordingly provides an advantage over other power transmission techniques, for example, inductive transmission techniques.

The power transmission process can be controlled (e.g., reduced, cycled, deactivated, etc.) to further reduce or prevent patient heating, such as heating of the patient's skin in contact with and/or near to the wearable device 170 and/or the power transmission device(s) 179 by, for example, temporarily and/or intermittently stopping the power transmission to reduce or prevent any heating associated with the power transmission and/or to allow the patient's tissue(s) time to cool. Additionally or alternatively, the power transmission process can be controlled to improve (e.g., optimize) therapy, therapy efficacy, patient therapy tolerance, and/or battery power. For example, power transmission from the wearable device 170 to individual ones of the implantable devices 120 can be cycled on and off based at least partially in response to data (e.g., received via one or more sensors 190, described in detail herein, e.g., with reference to FIG. 9) associated with one or more apneic events, sleep positions, and/or sleep states of the patient. Continuing with this example, the power transmission can be activated in response to data indicating that the patient is experiencing an apneic event. Additionally or alternatively, the power transmission can be activated or cycled (e.g., "duty cycled")

intermittently, such as at an ON:OFF ratio of 10:1, 5:1, 1:1, 1:5, 1:11, or another suitable ON:OFF ratio. Cycling the power transmission OFF may or may not interrupt delivery of electrical signals by one or more of the implantable devices 120, e.g., depending on the power storage capacity, if any, of the implantable devices. Additionally or alternatively, cycling the power transmission can reduce power consumption by the wearable device 170, and/or can increase the time during which the wearable device 170 can be used before recharging via the power source 184. In these and other embodiments, the system can be configured to receive an input (e.g., from the patient P and/or via the programmer 160) associated with a desired temperature or heating threshold, and can be configured to control the power transmission from the wearable 170 to the implantable device(s) 120 such that any tissue heating does not exceed the heating threshold. Further, in embodiments for which the potential heating caused by inductive power transmission is adequately controlled, inductive techniques can be used in lieu of the other (e.g., RF) power transmission techniques described herein.

In some embodiments, the wearable device 170 can be configured to transmit power using multiple power transmission devices 179 and/or at multiple frequencies. For example, a first power transmission device can be configured to transmit power at a first frequency (e.g., 904 MHz) and a second power transmission device can be configured to transmit power at the same time and at a second frequency (e.g., 906 MHz) different than the first frequency. The difference between the first and second frequencies can cause a beat frequency (e.g., a signal having a frequency equal to the absolute value of the difference between the first and second frequencies), which can be used to power and/or communicate with one or more of the implantable devices 120. For example, a first portion of the beat frequency can be rectified (e.g., to DC) by circuitry 138 onboard the implantable device 120 and used to power the implantable device 120, and/or a second portion of the beat frequency can be reflected back toward the wearable device 170. The second portion can be modulated for communication purposes, e.g., to communicate data with the wearable device 170 and/or the programmer 160. In at least some embodiments, the beat frequency is at a lower power level than the power transmitted by the first and/or the second power transmission devices and, as such, reduces the power and/or computational expenditure associated with receiving and/or processing communications from the implantable device(s) 120.

Additionally, or alternatively, the wearable device 170 can be configured to transmit power at multiple power levels. The wearable device 170 can be configured to transmit power at a first (e.g., low) power level, a second (e.g., medium) power level greater than the first power level, and/or a third (e.g., high) power level greater than the second power level. For example, the wearable device 170 can include a network of switches configured to control the transmitted power level, at least one power transmission device for each of the power levels (e.g., a first power transmission device configured to transmit power at the first power level, a second power transmission device configured to transmit power at the second power level, and a third power transmission device configured to transmit power at the third power level), and/or a digital-to-analog converter ("DAC") configured to control the power level of the power signal provided to the power transmission device(s) 179 for transmission. In some embodiments, the first power level can be from about 0.01 W to about 0.05 W, the second power level can be from about 0.1 W to about 0.3 W, and the third power level can be from about 0.5 W to about 1 W. In other embodiments, the first power level, the second power level, and/or the third power level can have other suitable values/value ranges.

Each of the power levels can be associated with a different operating state of one or more of the implantable devices 120. For example, at the first power level, one or more of the implantable devices 120 receiving power can be configured to send and/or receive transmissions, e.g., to/from the wearable 170 and/or programmer 160. At the second power level, one or more of the implantable devices 120 receiving power can perform the functions associated with the first power level, and one or more sensors carried by the implantable devices 120 receiving power can be configured to receive data associated with the patient. At the third power level, one or more of the implantable devices 120 receiving power can perform functions associated with the first and/or second power levels, and/or be configured to deliver one or more electrical signals to the patient, e.g., to reduce, prevent, or treat an apneic event. By transmitting power at multiple power levels, the amount of power transmitted can be selected to correspond to the desired operating state of the implantable device, e.g., to optimize power delivery and reduce or prevent transmission of excess power. In at least some embodiments, this multi-level power delivery can reduce the size of the power transmission device(s) 179 carried by the wearable device 170, reduce patient tissue heating during power transmission, improve the battery life of the wearable device 170, and/or improve (e.g., optimize) the quality, efficacy, efficiency, and/or timing/time delivery of the electrical signal(s) to the patient and/or the patient's response to the electrical signal(s).

Upon receipt of power from one or more of the power transmission devices 179, one or more of the implantable devices 120 can be configured to transmit a power receipt signal, e.g., to indicate that the power transmitted by the wearable device 170 was received by one or more of the implantable devices 120. The power (e.g., AC power) received at the receiver antenna 133 is rectified to DC (via, e.g., an AC-DC converter), then transmitted to a DC-DC converter, charge pump, and/or transformer 139, and converted to pulses in a range from about 10 Hz to about 500 Hz, such as from about 30 Hz to about 300 Hz. In other embodiments, the pulses can be delivered at a higher frequency (e.g., 10 kHz or more), and/or in the form of bursts. The amplitude of the signal can be from about 1 mV to about 5 V (and in particular embodiments, 1 V to 2 V) in a voltage-controlled system, or from about 0.5 mA to about 12 mA in a current-controlled system. The circuitry 138 controls these signal delivery parameters, and transmits the resulting electrical signal to the electrodes 131 via the wire filaments or other conductors 140 within the lead body 134. Accordingly, the circuitry forms (at least part of) the signal generator 110 in that it receives power that is wirelessly transmitted to the implantable device 120, and generates the signal that is ultimately delivered to the patient. The electrical field(s) resulting from the currents transmitted by the electrodes 131 produces the desired effect (e.g., excitation and/or inhibition) at the target nerve. In at least some embodiments, the implantable device 120 need not include any on-board power storage elements (e.g., power capacitors and/or batteries), or any power storage elements having a storage capacity greater than 0.5 seconds, so as to reduce system volume. In other embodiments, the implantable device 120 can include one or more small charge storage devices (e.g., low voltage, high capacitance capacitors, solid state batteries, and/or the like) that are compatible with the overall compact shape of the implantable device 120, and have a total charge storage capacity of no more than 1 second, 5 seconds, 10 seconds, 15 second, 20 seconds, 25 seconds, 30 seconds, 1 minute, 2 minutes, 5 minutes, any time period therebetween, or another suitable time period, depending on the embodiment.

Figure 5B:
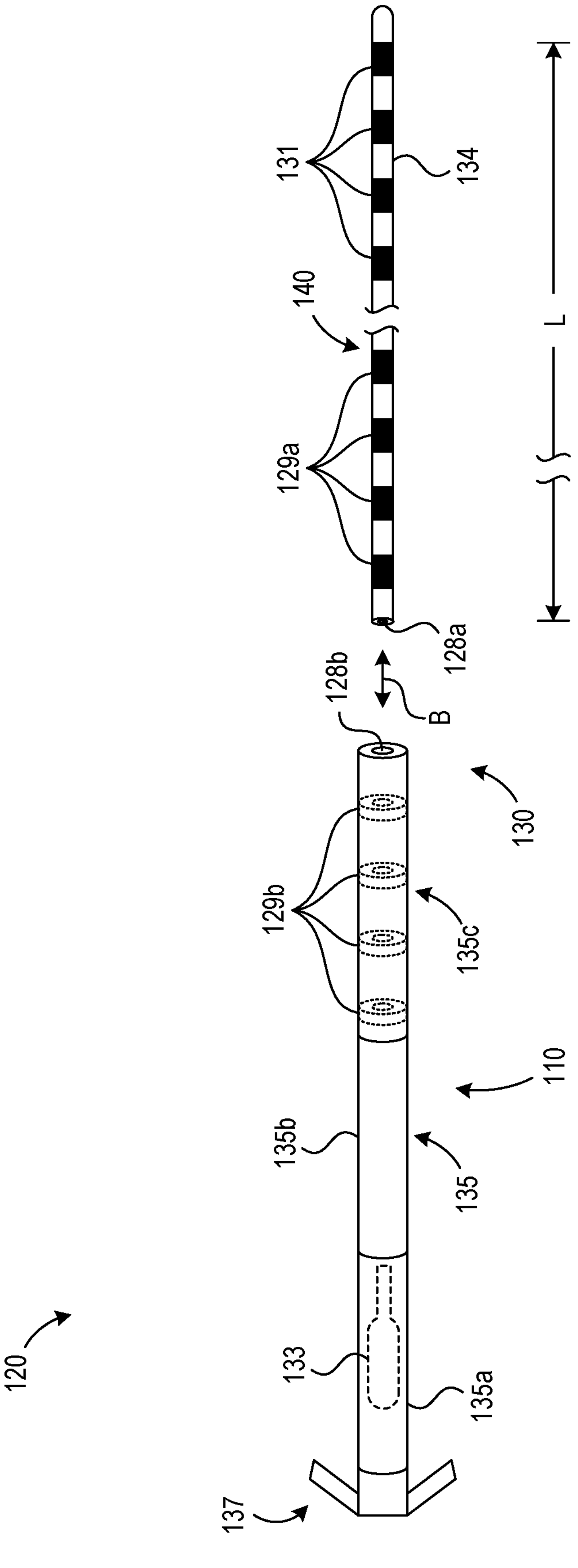

FIG. 5B is a partially schematic illustration of an implantable device 120 configured in accordance with further embodiments of the present technology. One feature of this embodiment is that the overall housing 135 (carrying the signal generator 110) and the lead body 134 are initially separate elements. Accordingly, the lead body 134 can be introduced into the patient, then positioned at or near the target neural population, and then connected to the overall housing 135. One advantage of this approach is that the practitioner can select from among different lead bodies 134 having different lengths, choosing the lead body 134 having the appropriate length (and/or other configuration attribute) for the particular patient undergoing therapy. Another advantage is that the diameter of the tunnel into which the (small diameter) lead body 134 is positioned can remain small enough to accommodate only the lead body 134, and not the (larger diameter) overall housing 135. This approach can reduce trauma to the tissue and allow the patient to achieve a therapeutic endpoint. Other techniques can also be used to further the foregoing results. For example, the tunnels (or at least portions of the tunnels) into which the signal delivery device 130 fit, can be formed via tissue dilation/dilatation rather than cutting. In addition to being less traumatic, this approach can produce tissue compression around the signal delivery device 130, which can at least reduce the tendency for this element to migrate.

The overall housing 135 can be positioned at, or very close to, an entry opening into the patient's tissue. This approach has the added advantage that the overall housing 135, which includes the antenna 133, will be positioned close to the patient's skin, which reduces power losses associated with transmitting power through the patient's skin to the signal delivery device 130. Because power losses typically produce heat, this approach can also reduce tissue heating.

The lead body 134 can include multiple electrodes 131 positioned toward its distal end. For purposes of illustration, four electrodes 131 are shown in FIG. 5B, but in other embodiments, the signal delivery device 130 can include other numbers of electrodes 131. Each electrode 131 is coupled to a corresponding first terminal 129*a* via a corresponding conductor 140 (not visible in FIG. 5B). The lead body 134 can have an overall length L that has any of a number of suitable predetermined/standard (or non-standard) values. The lead body 134 can include an axial lead opening 128*a*, for example, if the lead body 134 is delivered into the patient via a stylet. The stylet is then removed before connecting the lead body 134 to the overall housing 135. In other embodiments, no stylet is required, and instead, the lead body 134 is housed in the lumen of a needle, introducer, or sheath, and then deployed into the patient as the needle, introducer, or sheath is withdrawn from the patient.

The overall housing 135 includes an antenna housing 135*a* and circuit housing 135*b* at least generally similar to those discussed above with reference to FIG. 5A. The overall housing 135 can further include a connector housing 135*c* that houses second terminals 129*b*, shaped and positioned to receive the first terminals 129*a* of the lead body 134. The connector housing 135*c* can be partly or completely flexible. The second terminals 129*b* can be partly rigid, with flexible components (e.g., springs) to provide resilient physical and electrical contact with the first terminals 129*a*. In particular embodiments, the second terminals 129*b* can include donut-shaped terminals positioned along an axial housing opening 128*b*. Representative second terminals are manufactured by Bal Seal Engineering, Inc. of Lake Forest, Calif. In operation, the practitioner introduces the lead body 134 into the patient separately from the overall housing 135, for example, via a stylet. The lead body 134 is then connected to the overall housing 135 by inserting the lead body 134 into the housing axial opening 128*b* as indicated by arrow B. If the lead body 134 has previously been secured in position, then all or most of the insertion motion is undertaken by the overall housing 135, not the lead body 134. The overall housing 135 can be secured in position via one or more anchors 137, and/or sutures. If, in the unlikely event that either the lead body 134 or the overall housing 135 need to be replaced, each can be replaced separately from the other by separating the lead body 134 from the overall housing 135.

Because the lead body 134 and portions of the overall housing 135 are flexible, in addition to being separable, each of these components can have a different orientation when inserted into the patient's tissue. For example, the lead body 134 can extend at a shallow or steep angle into the patient's tissue to access the target nerve. The overall housing 135 can extend at a shallower angle (e.g., parallel to the patient's skin surface) to position the antenna 133 for better (e.g., optimal) power reception. However, both elements can be introduced into the patient through the same opening, thus limiting the invasiveness of the implant procedure. In addition, the proximity of the overall housing 135 to the opening reduces the length of the sheath and/or other introducer required to position the overall housing 135 at its target location. In other embodiments, the lead body 134 can be delivered using both a distal and proximal opening, as discussed in greater detail in U.S. application Ser. No. 17/749,025, filed on May 19, 2022, previously incorporated herein by reference.

Whether the implantable device 120 is implanted as a single unit or as two initially separated units, the technique of placing different portions of the implantable device 120 into tunnels have different diameters (as described above), can apply. This approach can more firmly secure elements of the implantable device 120 in place. For example, the implantation process can include inserting a small diameter guide wire (e.g., 0.014"), without further dilation, to form the distal 5-30 mm of the tunnel. This portion of the tunnel can snuggly accommodate the (small diameter) lead body 134. The portion of the tunnel that snuggly accommodates the (larger diameter) overall housing 135 can have a slightly larger diameter, e.g., 7 Fr (2.33 mm) to 8 Fr (2.66) mm. In the foregoing example, the lead body 134 can have a diameter of 3 Fr (1 mm), and the overall housing 135 can have a diameter of 6 Fr (2 mm). In other embodiments, these diameters can be different (larger or smaller) and the tunnel diameters adjusted accordingly. This approach can eliminate the need for tines or other slightly more invasive anchors. As described above, the opening(s) that accommodate the implantable device 120 can be formed primarily via dilation/dilatation, to reduce tissue trauma and/or improve device anchoring.

In at least some embodiments, the electrical signal delivered to the patient can be delivered via a bipole formed by two of the electrodes 131. In other embodiments, the signal can be a monopolar signal, with the housing 135 (e.g., the circuit housing 135*b*) forming a ground or return electrode.

In general, the waveform includes a biphasic, charge balanced waveform, as will be discussed in greater detail below with reference to FIGS. 22A-24C.

Figure 5C:
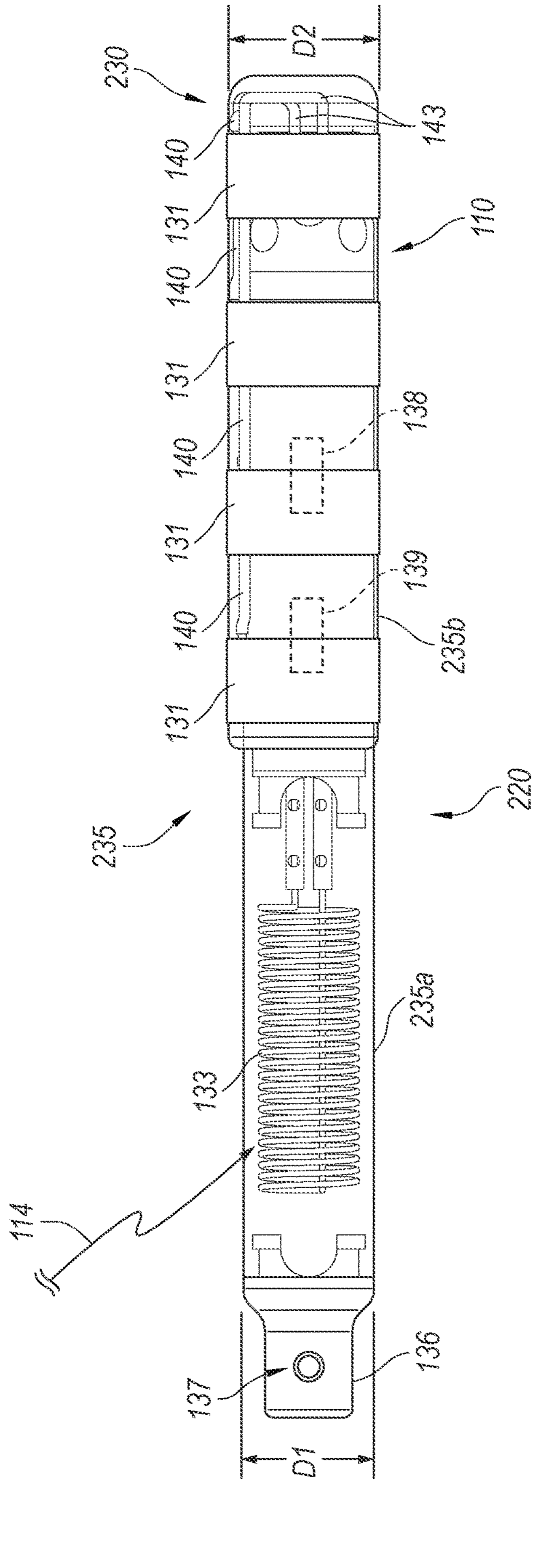

FIG. 5C is a side view of a further representative implantable device 220 including a leadless signal delivery device 230 configured in accordance with embodiments of the present technology. At least some aspects of the leadless signal delivery device 230 can be generally similar or identical in structure and/or function to the signal delivery device 130 of FIGS. 5A and/or 5B. Accordingly, like names and/or reference numbers (e.g., housing 235 of FIG. 6C versus the housing 135 of FIG. 6A) are used to indicate generally similar or identical components. The leadless signal delivery device 230 includes a housing 235 having a first housing portion 235*a*, a second housing portion 235*b*, and a base 136. The first housing portion 235*a* can be generally similar to the antenna housing 135*a*, and/or can have a first outer dimension D1 (e.g., a first width, a first diameter, a first circumference, and/or the like). The second housing portion 235*b* can be generally similar to the circuit housing 135*b*, and/or can have a second outer dimension D2 (e.g., a second width, a second diameter, a second circumference). In the illustrated embodiment the first outer dimension D1 is less than the second outer dimension D2. In other embodiments, the first outer dimension D1 can be equal to or greater than the second outer dimension D2. The base 136 can include one or more of the anchors 137.

The leadless signal delivery device 230 can further include the electrode receiver antenna 133, the signal generator 110, the circuitry 138, the charge pump 139, and the one or more electrodes 131. In the illustrated embodiment, the electrode receiver antenna 133 is positioned within the first housing portion 235*a*, the signal generator 110, the circuit 138, and the charge pump 139 are positioned within the second housing portion 235*b*, and the electrodes 131 are carried by the second housing portion 235*b*. For example, as shown in FIG. 5C, the electrodes 131 are positioned to be exposed from an exterior surface of the second housing portion 235*b*, such that individual ones of the electrodes 131 extend at least partially around a circumference of the second housing portion 235*b*. Accordingly, one or more of the electrodes 131 can extend at least partially or fully around (e.g., circumferentially around, axially around, etc.) one or more of the internal components of the leadless signal delivery device 230. In the illustrated embodiment, the signal generator 110, the circuitry 138, and the charge pump 139 are each positioned within the second housing portion 235*b* such that one or more of the electrodes 131 extend at least partially around each of the signal generator 110, the circuitry 138, and the charge pump 139. More specifically, in the illustrated embodiment the electrodes 131 and/or the second housing portion 235*b* define an axial space or volume within which each of the signal generator 110, the circuitry 138, and the charge pump 139 are positioned. Additionally, or alternatively, the electrode receiver antenna 133 can be positioned within the second housing portion 235*b*, such that one or more of the electrodes 131 can extend at least partially around the electrode receiver antenna 133. In such embodiments, the second housing portion 235*b* can be configured to reduce or prevent interference with the electrode receiver antenna's reception of the power transmission link 114. The electrodes 131 and/or the second housing portion 235*b* are not expected to interfere with the operation of the electrode receiver antenna 133. Additionally, or alternatively, one or more electrodes can be positioned on or at the first housing portion 235*a* to extend at least partially around the electrode receiver antenna 133. In these and other embodiments, one or more of the signal generator 110, the circuitry 138, and/or the charge pump 139 can be positioned within the first housing portion 235*a* and/or otherwise positioned outside and/or laterally relative to the space defined by the electrodes 131 and/or the second housing portion 235*b*.

Each of the electrodes 131 can be coupled to the signal generator 110 via a respective conductor 140. In the illustrated embodiment, each of the conductors 140 are positioned within the second housing portion 235*b*, for example, between the signal generator 110 and an inner surface of the second housing portion 235*b*. Additionally, or alternatively, one or more feedthroughs 143 can couple individual ones of the conductors 140 to the signal generator 110.

5. Representative Stimulation Targets and Implantation Techniques

Several stimulation targets and implantation techniques are described and/or illustrated with reference to FIGS. 6A-8B. For the purpose of illustrative clarity, these stimulation targets and implantation techniques are shown with reference to a left or right side of the patient P's anatomy, for example, a left medial branch of a left hypoglossal nerve of the patient P. It will be appreciated, however, that at least some or all of the stimulation targets and/or implantation techniques described and/or illustrated with reference to FIGS. 6A-8B are equally suitable for application to another side of the patient's anatomy, for example, a right medial branch of a right hypoglossal nerve of the patient P. Additionally, at least some of the stimulation targets and/or implantation techniques can be used for bilateral signal delivery, for example, to apply a first electrical signal to a first stimulation target on a first side of the patient P and to apply a second electrical signal to a second stimulation target on a side of the patient P. In some embodiments, the first and second stimulation targets can be corresponding left and right portions of the patient's anatomy, such as the left and right medial branches of the left and right hypoglossal nerves. In other embodiments, the first and second stimulation targets can be different, such as a left medial branch of the left hypoglossal nerve and a right ansa cervicalis nerve of the patient.

Figure 6A:
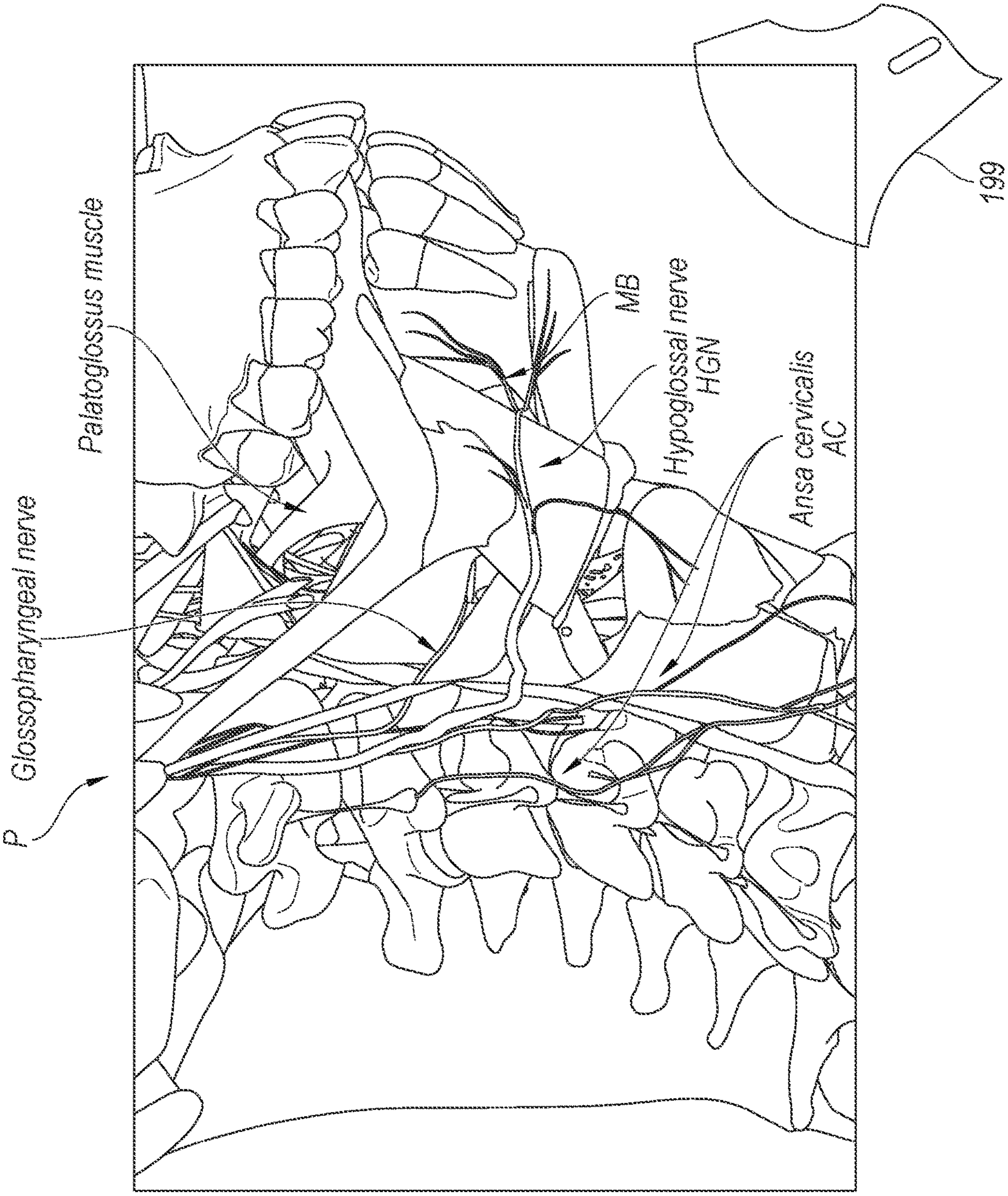
FIG. 6A is a side view of a patient's skull, illustrating representative signal delivery targets in accordance with embodiments of the present technology.

FIG. 6A is a partially schematic, partially cut-away sagittal view of the neck and lower head region of the patient P. FIG. 6A illustrates representative neural structures of this region, including the hypoglossal nerve HGN (and its medial branch MB) and the ansa cervicalis AC. FIG. 6A also illustrates a representative ultrasound probe 199, used to aid in the process of positioning electrodes, which direct therapy signals to the target nerves.

Figure 6B:
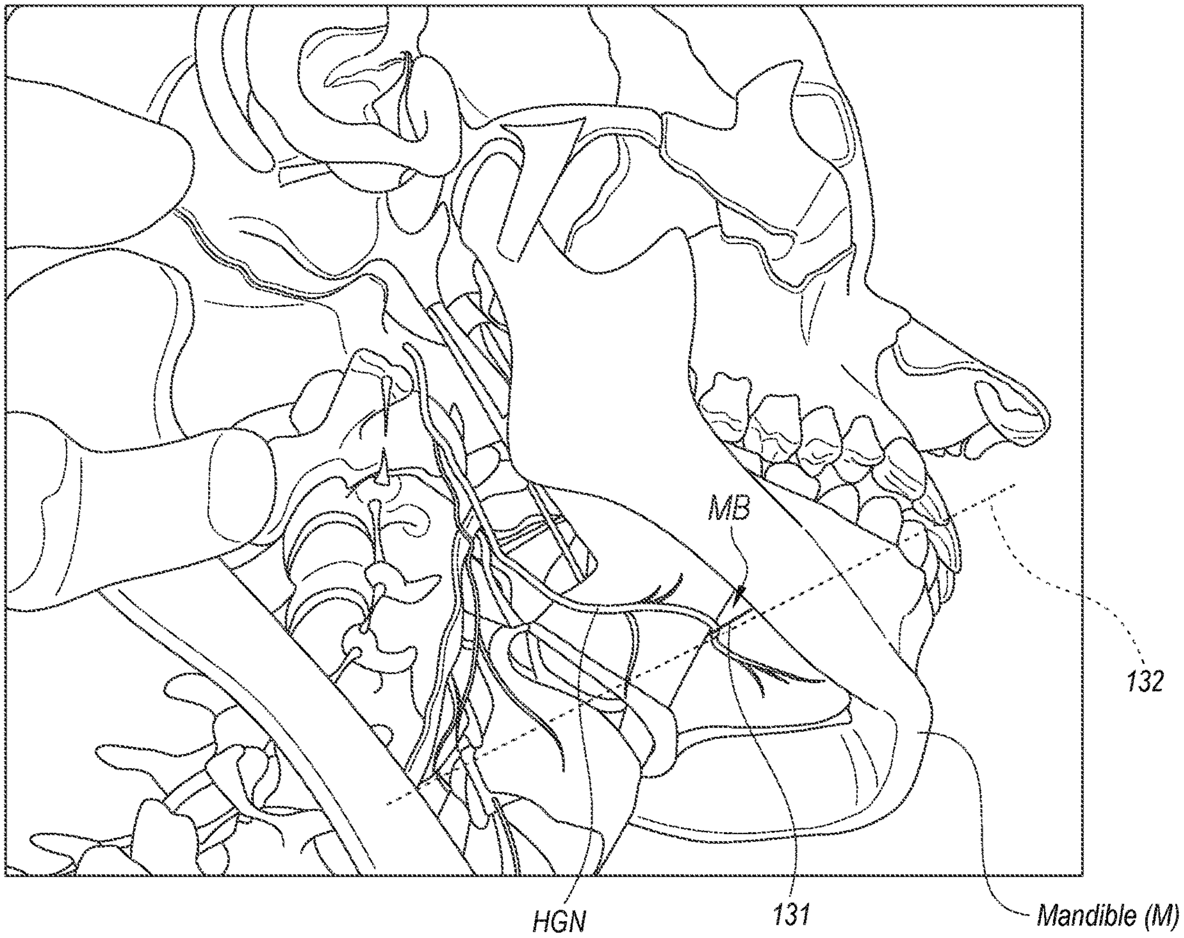
FIG. 6B is a view of a patient's skull, from below, illustrating the hypoglossal nerve and a representative electrode location in accordance with embodiments of the present technology.

FIG. 6B is a partially schematic, isometric illustration of the patient's skull, looking upwardly toward the mandible M. FIG. 6B also illustrates the hypoglossal nerve HGN which innervates the muscles controlling the patient's tongue T (FIG. 1). In representative embodiments, one or more electrodes 131 are positioned along the hypoglossal nerve HGN, in particular, at the medial branch MB of the HGN, in an electrode plane 132 defined by the medial branch MB. By precisely positioning the electrode(s) 131 within this plane 132, and adjacent to the hypoglossal nerve HGN, it is expected that systems in accordance with embodiments of the present technology can more effectively control the patient's airway patency, without causing discomfort, and/or other undesirable effects, and/or in a manner that reduces the amount of power required to produce effective therapy signals. As discussed elsewhere herein, other representative target nerves include the ansa cervicalis and vagal nerves, and/or one or more of the muscles innervated by these nerves. Still further representative targets include cranial nerves (e.g., the glossopharyngeal nerve) and the palatoglossus muscle, which are shown in FIG. 6A, and the left and/or right phrenic nerves.

Figure 6C:
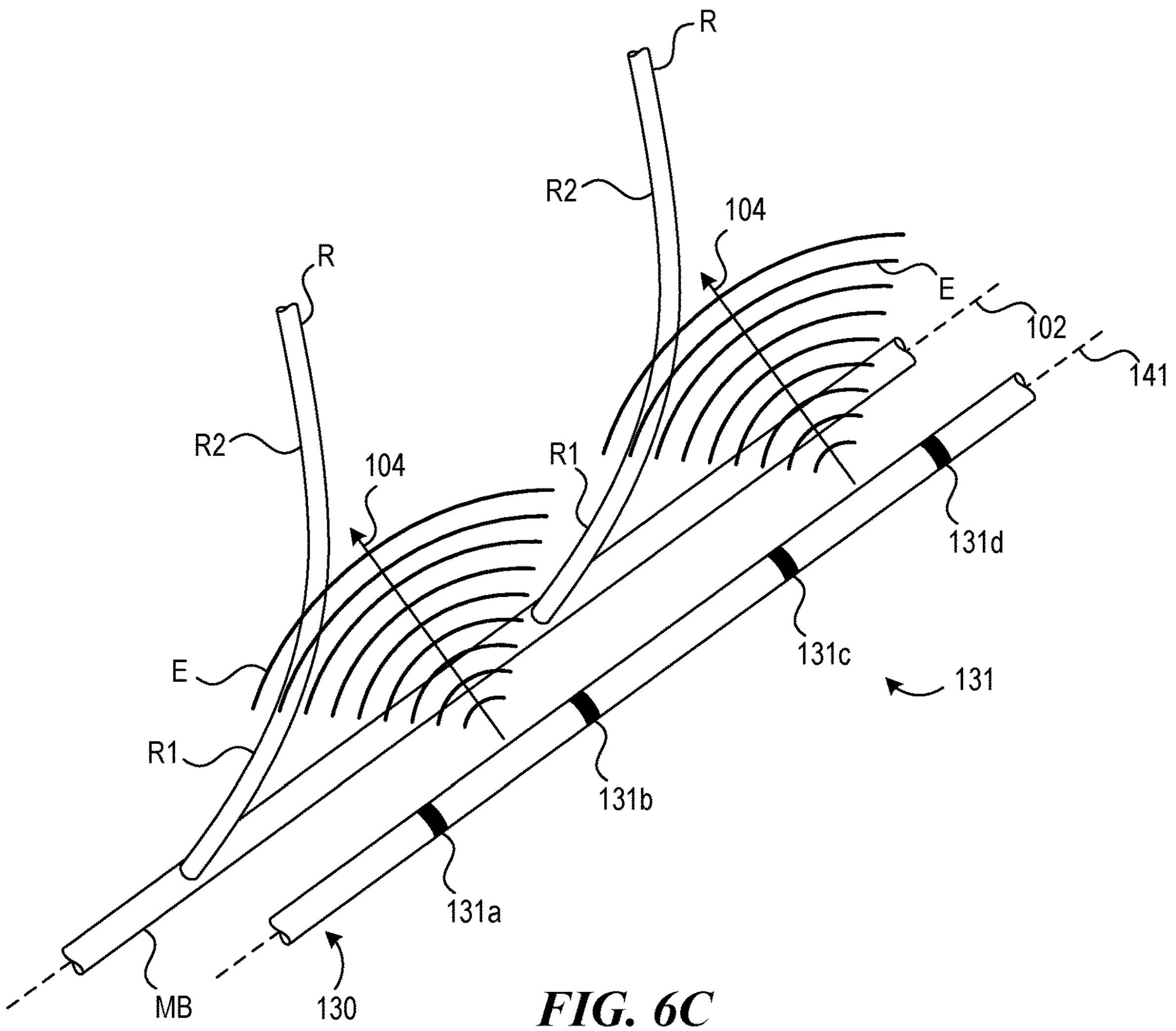
FIGS. 6C and 6D illustrate an isometric view and an end view, respectively, of the medial branch of the hypoglossal nerve, and an associated signal delivery device, positioned in accordance with embodiments of the present technology.

FIG. 6C is a partially schematic illustration of the medial branch MB, and an associated signal delivery device 130, positioned in accordance with embodiments of the present technology. The medial branch MB extends along a nerve axis 102 and innervates oral cavity muscles such as the genioglossus and geniohyoid muscles, which tend to pull the tongue forward (anteriorly), thus reducing the tendency for the soft tissue of the palate to prolapse into the patient's airway. However, the medial branch MB also includes retrusers R which innervate muscles such as the styloglossus and the hyoglossus muscles, which tend to pull the soft tissue backward (posteriorly), and/or can cause the tongue to curl left or right within the mouth—both are motor responses that can obstruct the patient's airway. Accordingly, it can be advantageous to stimulate the medial branch MB via the electrodes 131 in a manner that results in a net positive protrusive effect or a net protrusive motor response. This can include, for example, stimulating the medial branch MB so as to avoid activating the retrusers R entirely. Additionally, or alternatively, the net positive protrusive effect can be obtained when the protrusive response to an electrical signal is greater than, or otherwise counteracts, the retrusive response to the electrical signal. This can include, for example, delivering an electrical signal to one or more of a patient's nerves and/or muscles such that, in response to the electrical signal, the patient's airway is more open and/or allows more airflow than when the electrical signal is not delivered. One approach for obtaining the net positive protrusive effect is to position the electrodes 131 to preferentially stimulate the medial branch MB itself, without stimulating (or without significantly stimulating) the retrusers R.

As shown in FIG. 6C, the retrusers R typically include a first portion R1 that extends parallel or at least partially parallel to the nerve axis 102 of the medial branch MB. The retrusers R further include a second portion R2 that bends away from the nerve axis 102. Accordingly, one approach for avoiding or reducing stimulation of the retrusers R is to position the electrodes 131 axially so that the corresponding electrical fields they produce are less likely to activate the retrusers R. As shown in FIG. 6C, the electrodes 131 are arranged in electrode pairs, including a first pair (comprising first and second electrodes 131*a* and 131*b*), and a second pair (comprising third and fourth electrodes 131*c*, 131*d*). Other embodiments can include more or fewer electrodes and/or electrode pairs. Each electrode pair generates an electrical field E which decreases in strength in a direction away from the electrodes 131, as indicated by decreasing field strength arrows 104. The electrical fields E preferentially activate neural tissue that extends transverse to the field, rather than parallel to the field. Accordingly, with a device axis 141 of the signal delivery device 130 generally parallel to the nerve axis 102 of the medial branch MB, the electrical fields E preferentially activate the medial branch MB. However, if the electrical fields E are positioned close to the first portions R1 of the retrusers R (which are also parallel or close to parallel to the nerve axis 102), then the electrical fields E may also activate the retrusers R. One approach for avoiding this outcome is to position the electrodes 131 to be offset along the nerve axis 102 relative to the first portions R1 of the retrusers R. In this way, the electrical field E is less likely to activate the retrusers R at the first portions R1. Although the second portions R2 of the retrusers R are transverse to the electrical field (and therefore potentially susceptible to the field), the field at the second portions R2 is expected to be too weak to have a significant effect on the retrusers R. In these and other embodiments, one or more of the electrodes 131 can be masked (e.g., circumferentially masked), segmented (e.g., circumferentially segmented, individually addressable), directional, at least partially covered, and/or otherwise configured to direct the electrical field in specific direction(s) to further reduce the likelihood of stimulating the retrusers R.

Figure 6D:
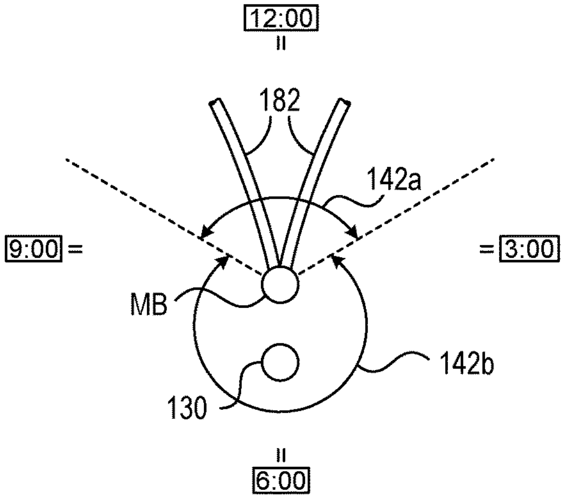

Another approach for reducing the effect of the electrical fields on the retrusers R is to selectively position the electrodes circumferentially, as illustrated in FIG. 6D. As shown in FIG. 6D, the retrusers R tend to exit the medial branch MB in a generally superior direction, while the signal delivery device 130 is positioned inferior to the medial branch MB. Accordingly, if the retrusers R extend away from the medial branch MB in a first area 142*a* at a clock position of from about 10 o'clock to about 2 o'clock (measured clockwise), the signal delivery device 130 can be positioned in a second area 142*b* away (e.g., axially offset, opposite, and the like) from the first area 142*a*: i.e., between about 2 o'clock and about 10 o'clock (measured clockwise), and/or any suitable subarea therein (e.g., between any of 2 o'clock, 3 o'clock, 4 o'clock, 5 o'clock, 6 o'clock, 7 o'clock, 8 o'clock, 9 o'clock, and 10 o'clock). If the retrusers R extend in a generally inferior direction from the medial branch MB, the signal delivery device 130 can be positioned generally superior to the medial branch MB.

A further approach for reducing the effect(s) of the electrical fields on the retrusers R is to position the electrodes at or proximate to the motor end plate of the target nerve, such as where the HGN innervates the patient's tongue and/or at or within the genioglossus muscle(s) GGM. For example, the signal delivery device 130 can be positioned proximate to and/or adjacent to a brachiated portion of the patient's target nerve. This is described in further detail with reference to FIG. 7A. With the signal delivery device 130 in this position, the electrical field E generated by the signal delivery device 130 is spaced apart from the retrusers R and is expected to be too weak to have a significant effect on the retrusers R. In some aspects, positioning the signal delivery device 130 further anterior, such as further into the brachiated portion of the patient's target nerve, can further focus the electrical fields on the target nerve and/or further reduce the likelihood of stimulating the retrusers R. The foregoing techniques (axial location, circumferential "clocking," and brachial positioning) can be used either individually or in combination, and it is expected that using these techniques in combination will further reduce the likelihood for activating the retrusers R.

As indicated above, it can be important to carefully position the electrodes to enhance the beneficial effects associated with the electrical therapy, and reduce countereffects, such as activating the retrusers R. U.S. application Ser. No. 17/749,025, filed on May 19, 2022, previously incorporated by reference herein, discloses a technique for percutaneously introducing and positioning a signal delivery device via a single entry location, with the aid of an ultrasound probe (shown in FIG. 6A).

In one approach a stylet is used to form a single puncture in the patient's skin. The puncture can be located in a posterior submandibular region of the patient. The signal delivery device 130 can be percutaneously introduced (e.g., implanted, injected, and/or the like) through the posterior submandibular puncture and be positioned proximate the medial branch MB of the hypoglossal nerve HGN.

In another approach a stylet is used to form a single puncture in the patient's mouth. The puncture can be located in an intraoral sublingual region of the patient's mouth, such as under the ventral surface of the tongue in the floor of the mouth, posterior to the sublingual caruncle and angled inferolaterally towards the medial branch of hypoglossal nerve. The signal delivery device 130 can be percutaneously introduced through the intraoral sublingual puncture and be positioned proximate the medial branch MB of the hypoglossal nerve HGN.

Another approach, described further in U.S. application Ser. No. 17/749,025, filed on May 19, 2022, previously incorporated by reference herein, uses a stylet and two punctures in the patient's skin to position the signal delivery device 130. The stylet can be curved, straight, or have any other suitable configuration. In particular embodiments, the signal delivery device can include a suture thread at each end, so that the practitioner can pull on one end and/or the other to precisely locate the signal delivery device (and the electrodes it carries) at the target location.

Figure 7A:
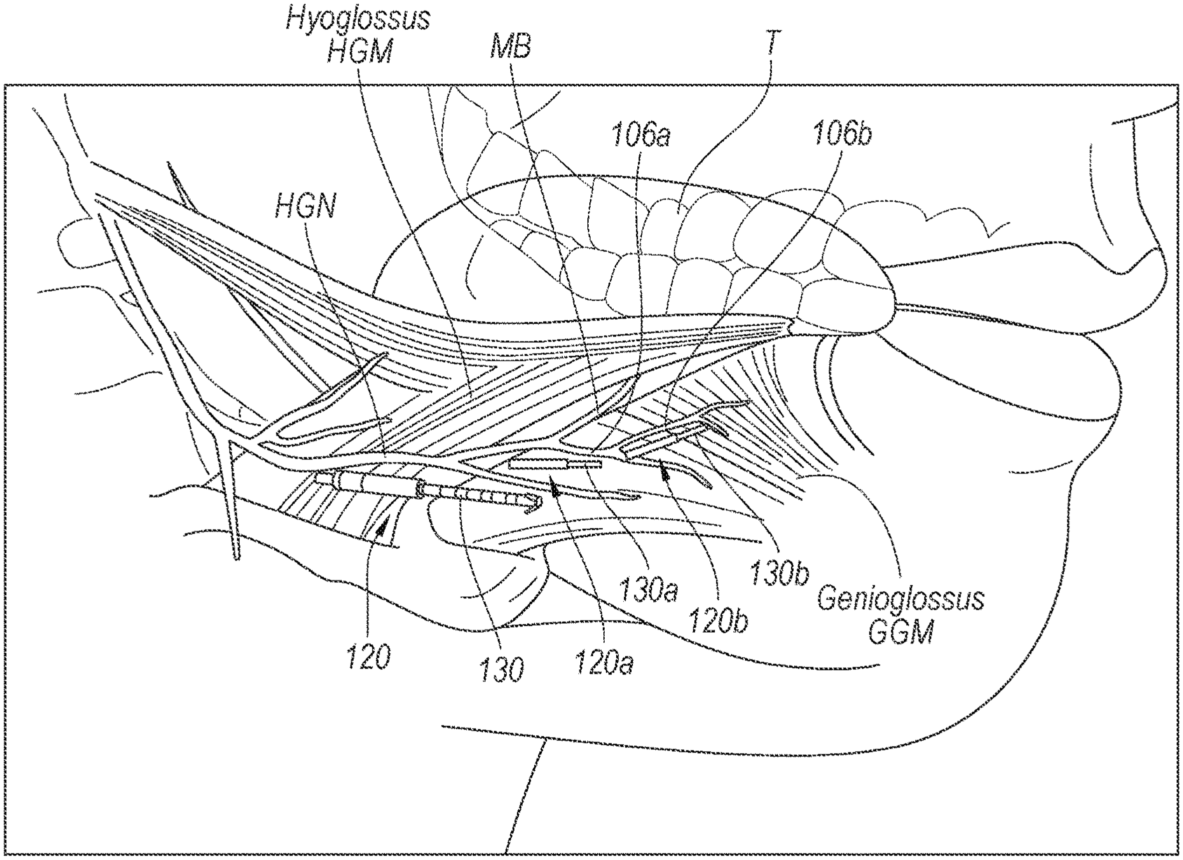
FIG. 7A is another illustration of the implantable device, with the signal delivery device positioned to direct an electrical field toward the medial branch of the hypoglossal nerve.

FIG. 7A is another illustration of the implantable device 120, with the signal delivery device 130 positioned to direct an electrical field toward the medial branch MB of the hypoglossal nerve HGN. As shown in FIG. 7A, the signal delivery device 130 can be positioned between the planes defined by the mylohyoid (which is out of the plane of FIG. 7A), the genioglossus muscle GGM and the hyoglossus muscle HGM. Accordingly, in some embodiments, the signal delivery device 130 can abut or be close to the surface of the genioglossus muscle GGM, without penetrating into the genioglossus muscle GGM. In other embodiments, the signal delivery device 130 can penetrate into the genioglossus GGM, which can aid in supporting the signal delivery device at its target location. The signal delivery device 130 can be positioned anterior to the anterior edge of the hyoglossus HGM (as shown in FIG. 7A) so as to direct therapeutic signals to the medial branch MB, and/or can have other suitable positions, e.g., closer to the medial branch MB (as shown in FIGS. 6A-6D). In some embodiments, the implantable device 120 can be positioned anteriorly relative to the position shown in FIG. 7A, such that the signal delivery device 130 can be positioned to direct an electrical field toward one or more portions 106*a*-*b* of the HGN and/or at or proximate to the motor end plate where the HGN and/or one or more of the portions 106*a*-*b* thereof that innervate the tongue T. For example, in addition to or in lieu of positioning the implantable device 120 as shown, a first implantable device 120*a* (shown schematically) can be positioned such that a first signal delivery device 130*a* (shown schematically) is positioned to direct an electrical field toward a first portion 106*a* of the HGN, and/or a second implantable device 120*b* (shown schematically) can be positioned such that a second signal delivery device 130*b* (shown schematically) is positioned to direct an electrical field toward a second portion 106*b* of the HGN.

Figure 7B:
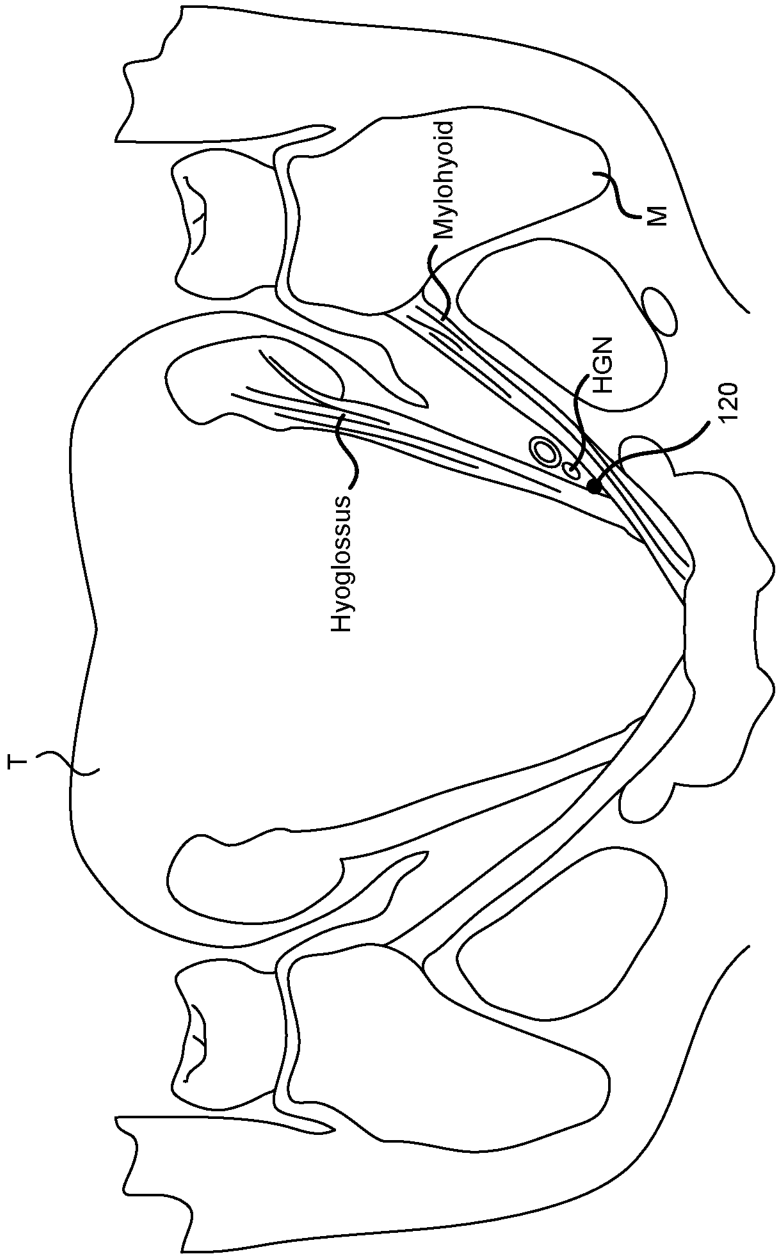
FIG. 7B is a coronal view taken through the patient's oral cavity, illustrating the implantable device in a representative position. The device is seen in cross-section as it extends into and out of the plane of FIG. 7B. In this position, the device is just lateral from the hyoglossus and just medial from the mylohyoid at or near the point at which the planes of these two muscles cross. The device is positioned just inferior to the HGN, which also extends into and out of the plane of FIG. 7B FIGS. 8A and 8B are partially schematic illustrations of the ansa cervicalis, hypoglossal nerve, associated musculature, and associated signal delivery devices, positioned in accordance with embodiments of the present technology.

FIG. 7B is a coronal view taken through the patient's oral cavity, illustrating the implantable device 120 in a representative position. The device 120 is seen in cross-section as it extends into and out of the plane of FIG. 7B. In this position, the device 120 is just lateral from the hyoglossus HGM and just medial from the mylohyoid at or near the point at which the planes of these two muscles cross. The device 120 is positioned just inferior to the HGN, which also extends into and out of the plane of FIG. 7B An advantage of the foregoing approach is that the practitioner can move the signal delivery device 130 back and forth to find a precise target location, without having to make an incision in the patient. Instead, the signal delivery device is introduced into the patient percutaneously, which can improve patient outcomes, for example, by reducing the likelihood for an infection to develop. In addition, while anchors 137 (FIG. 5A) may be used to secure the signal delivery device 130 in position, in at least some embodiments, suture threads, which can be coupled to one or both ends of the signal delivery device 130, are sufficient to do so. In still further embodiments, the signal delivery device 130 can be held in position solely by the forces provided by the adjacent muscles, e.g., the mylohyoid, the genioglossus GGM and the hyoglossus muscles HGM, or by virtue of penetrating into the genioglossus GGM, as discussed above, with suture threads and/or other anchor devices. Still further, in any of the foregoing embodiments, the signal generation function and the signal delivery function can be performed by initially separate elements, which are joined during the implant process, as discussed in further detail with reference to FIG. 5B.

Any of the techniques described herein for implanting the signal delivery device 130 can include one or more additional operations. For example, the practitioner can compress or otherwise manipulate (e.g., with his/her fingers) the submandibular or intraoral tissue to facilitate positioning the signal delivery device. These methods can allow the practitioner to manipulate the trajectory of the implant needle toward a desired endpoint. The additional force can be in the form of manual pressure applied intra- or extraoral, and/or vacuum that is targeted to move tissue as a way of improving the precision with which the signal delivery device is implanted. Pressure and/or suction can also be used to avoid structures, such as glands.

Figure 8A:
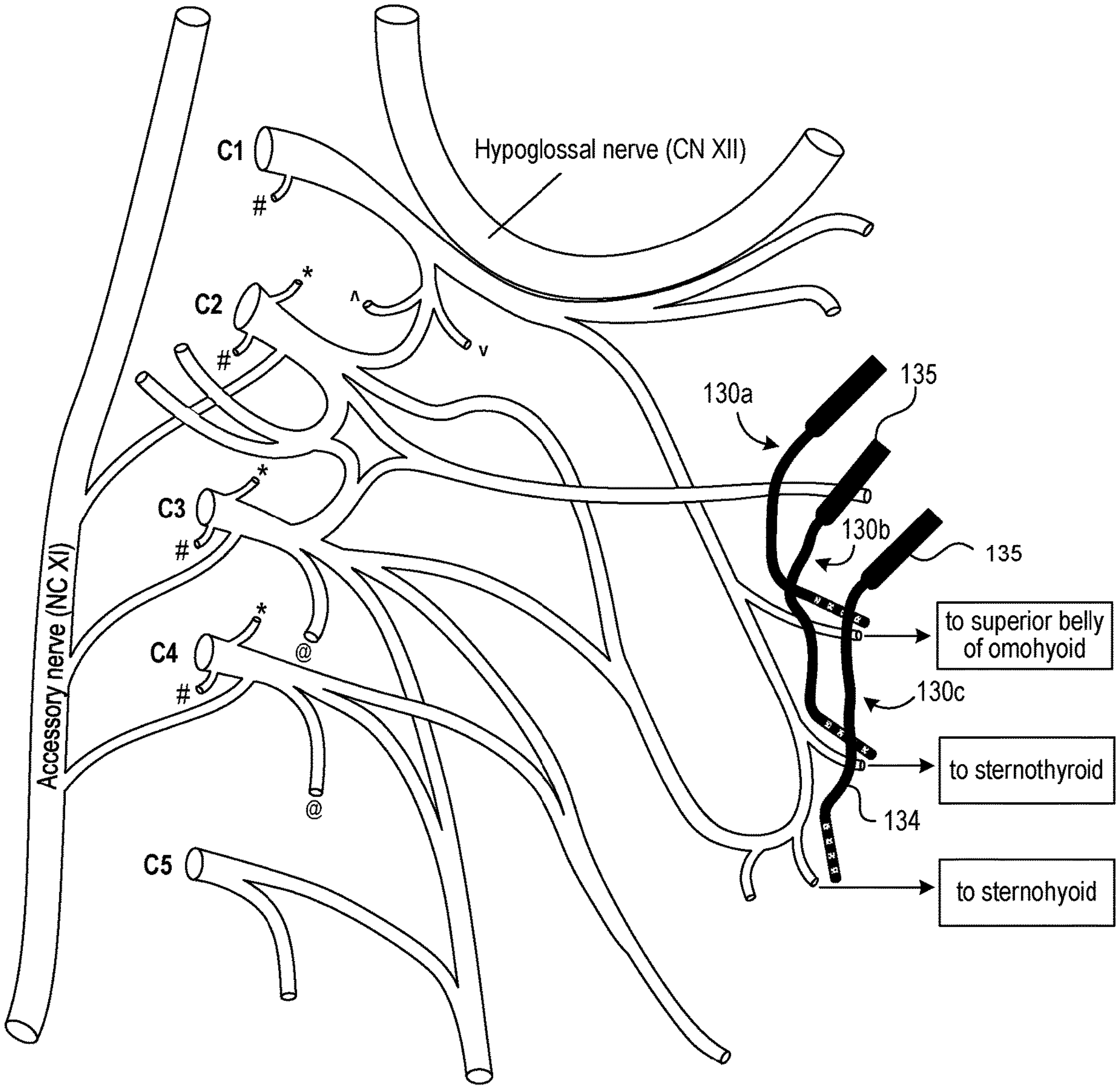

The foregoing discussion with reference to FIGS. 6A-7B focused on electrodes positioned to deliver signals to the medial branch MB of the hypoglossal nerve HGN. As discussed previously, it is expected to be advantageous to apply electrical signals to the ansa cervicalis AC and/or directly to one or more of the muscles innervated by the ansa cervicalis AC, in addition to or in lieu of applying signals to the medial branch. FIG. 8A is a partially schematic illustration of the hypoglossal nerve HGN and the ansa cervicalis AC, illustrating three branches of the ansa cervicalis AC that innervate the omohyoid, the sternothyroid, and the sternohyoid muscles. FIG. 8A also illustrates three representative signal delivery devices 130 (shown as devices 130*a*, 130*b*, 130*c*), each of which is positioned to direct electrical signals to a corresponding one of the branching nerves. In the illustrated embodiment, each signal delivery device 130 can include a lead body 134, carrying electrodes that are positioned to direct signals to the corresponding nerve, and a housing 135 that carries elements for receiving power from a remote power source, and generating the signals that are then supplied to the electrodes. In other embodiments, the electrode(s) 131 of one or more of the leadless signal delivery devices 230 of FIG. 5C can be positioned as shown in FIG. 8A; this can reduce the overall size (e.g., length) of the implantable device and improve the practitioner's ability to precisely position the signal delivery device 130 at or proximate the target nerve. Any of the implantation approaches discussed above and/or otherwise incorporated by reference herein can also be used to position the signal delivery device(s) 130 proximate to the ansa cervicalis AC.

Figure 8B:
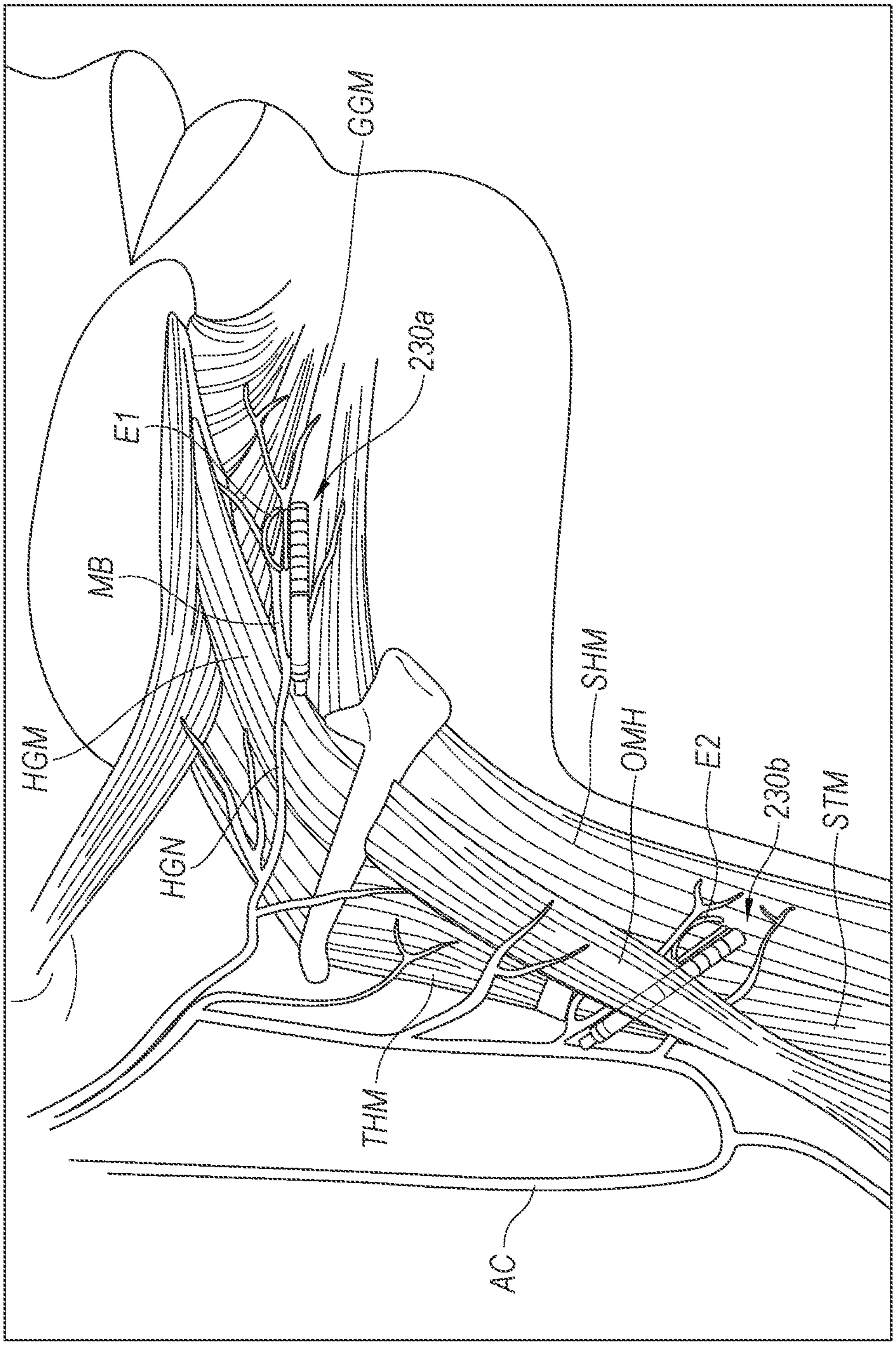

In some embodiments, electrical signals can be applied to multiple different targets. For example, FIG. 8B illustrates two of the signal delivery devices 230 of FIG. 5C (individually identified as a first signal delivery device 230*a* and a second signal delivery device 230*b*). The first signal delivery device 230*a* is positioned to deliver a first electrical signal (schematically represented as a first electrical field E1) to the medial branch MB of the hypoglossal nerve HGN and the second signal delivery device 230*b* is positioned to deliver a second electrical signal (schematically represented as a second electrical field E2) to the ansa cervicalis nerve AC. In other embodiments, the first signal delivery device 230*a* and/or the second signal delivery device 230*b* can be positioned to directly stimulate one or more of the muscles at or near their respective locations. For example, the first signal delivery device 130*a* can be positioned to deliver the first electrical signal/field E1 to the hyoglossus muscle HGM and/or the genioglossus muscle GGM, and/or the second signal delivery device 130*b* can be positioned to deliver the second electrical signal/field E2 to the thyrohyoid THM muscle, the sternohyoid muscle SHM, the omohyoid muscle OMH, and/or the sternothyroid muscle STM. Although the signal delivery devices 230 illustrated in FIG. 5B are leadless, in other embodiments leaded signal delivery devices, such as the signal delivery device 130, can be positioned as shown in FIG. 5B.

6. Representative Wearable Devices

Several wearable devices are described and/or illustrated with reference to FIGS. 9-21. For the purpose of illustrative clarity, at least some of these wearable devices are shown with reference to a left or right side of the patient P's anatomy, for example, a left side of the patient's head and/or neck. It will be appreciated, however, that at least some or all of the wearable devices described and/or illustrated with reference to FIGS. 9-21 are equally suitable for application to another side of the patient's anatomy, for example, a right side of the patient's head and/or neck. Additionally, at least some of the wearable devices can be used for bilateral power delivery, for example, to transmit a first power signal to a first implantable device positioned at or near a first stimulation target on a first side of the patient P and to transmit a second power signal to a second implantable device positioned at or near a second stimulation target on a second side of the patient P. In some embodiments, the first and second stimulation targets can be corresponding left and right portions of the patient's anatomy, such as the left and right medial branches of the left and right hypoglossal nerves. In other embodiments, the first and second stimulation targets can be different, such as a left medial branch of the left hypoglossal nerve and a right ansa cervicalis nerve of the patient.

Figure 9:
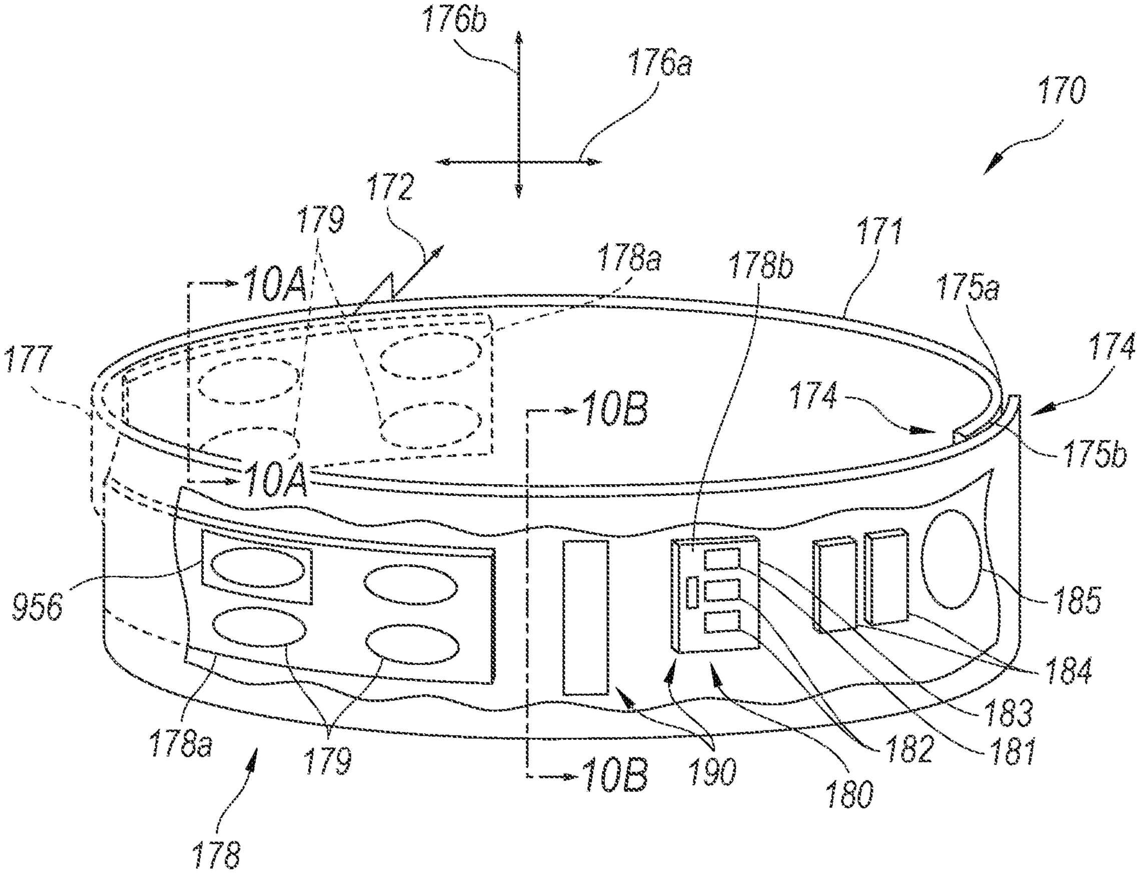
FIG. 9 is a partially schematic, partially cut-away illustration of a wearable device having a collar form factor, in accordance with embodiments of the present technology.

FIG. 9 is a partially schematic, partially cut-away illustration of a representative wearable device 170, having the form factor of a collar 171, and configured to communicate power and/or data to/from the implantable device 120 discussed above. The collar 171 can have a variety of suitable shapes and configurations, including a low profile sweatband type configuration (shown in FIG. 9), or a higher profile neck brace type configuration (described later with reference to FIG. 11). At least portions of the collar 171 can be formed from an elastic or another stretchable material so as to stretch along a first axis 176*a* and a second axis 176*b* to provide a comfortable fit for patients having a variety of physiologies. The collar 171 can have a one-piece configuration, so as to fit over the patient's head, or can have the form of an elongated band, with attachment portions 174 at each end, to releasably secure the collar 171 around the patient's neck. The attachment portions 174 can include corresponding hook and loop sections 175*a*, 175*b* configured to releasably couple each other when positioned in an overlapping or "wrapped" arrangement, such as shown in FIG. 9. In other embodiments, the attachment portion 174 can be configured to releasably couple to each other end-to-end (e.g., without or substantially without overlapping), and/or can include one or more buttons, buckles, snaps, ties, magnetic couplings, zippers, clasps, another suitable coupling feature, and/or have other suitable arrangements.

The collar 171 can carry multiple elements of wearable device circuitry 180, carried by one or more substrates 178, or carried directly by the collar 171 itself. Several of these elements can be internal to the collar 171, which is shown partially cut-away to illustrate these elements. For example, the collar 171 can carry one or more first substrates 178*a* that in turn carry one or more power transmission devices 179, e.g., antennae, coils, and/or other suitable structures. The collar 171, one or more of the substrates 178, and/or another portion of the wearable device can include and/or be formed from one or more thermally conductive material configured to at least partially or fully prevent patient heating, e.g., associated with the power transmission process. The power transmission devices 179 can be flexible/conformal to provide patient comfort, while at the same time being positioned with sufficient precision and certainty to provide power to the implantable device(s) described above with reference to FIGS. 4-5C. In at least some embodiments, multiple power transmission devices 179 can be arranged in an array to provide a greater degree of power transmission reliability, and/or to provide power to multiple implantable devices 120. The implantable device(s) 120 can be implanted with the associated power reception devices positioned to receive power from the power transmission devices 179, for example, within the projected area of the field generated by the power transmission device(s) 179 on the patient's skin. When it includes multiple power transmission devices 179, the wearable 170 can be configured to optimize power transmission to the implantable device(s) 120. For example, the circuitry can identify one or more of the power transmission devices 179 that are positioned the closest to one or more of the implantable devices 120 and then transmit power to those implantable devices 120 using the identified power transmission devices 179, and/or deactivate the other power transmission device(s) 179. Additionally, or alternatively, the circuitry can be configured to transfer power transmission duties between individual ones of the power transmission devices 179, such as from one power transmission device to one or more other power transmission devices. In these and other embodiments, proximity may not be the only factor in determining power transmission efficiency. Other factors (e.g., tissue impedance, patient sleep state, patient sleep position, and/or other factors/data described herein) may also play a role, and may affect which power transmission device is selected at any point in time, and/or for any particular implantable device 120.

Additionally or alternatively, at least one of the power transmission devices 179 can be movable relative to other portions of the wearable device 170. For example, the power transmission device 179 can be coupled to an actuator or drive element 956 (e.g., a stepper motor) configured to move at least partially around (e.g., circumferentially around) a patient's neck, such as between at least two different positions. As another example, the field generated by the power transmission device 179 can be directional (e.g., at least generally similar to the directional fields described above with reference to FIGS. 6C and 6D) and configured to be pointed or directed toward at least two different positions. In these and other embodiments, each of the positions to which the power transmission device 179 can be moved/oriented can be associated with a respective implantable device 120 and/or implantable device location, such that the power transmission device 179 can be aligned with and/or otherwise positioned to transmit power to one or more implantable devices 120 when moved/oriented to each of the positions. Representative locations for the implantable devices are described herein with reference to FIGS. 1-4 and 6A-8B, e.g., the medial branch MB of the patient's hypoglossal nerve HGN, and/or the ansa cervicalis AC.

In a particular embodiment, the collar 171 can include a cutout 177 (shown in dashed lines), e.g., having a V-shape configured to accommodate the patient's larynx, which tends to bulge outwardly from the patient's neck. The cutout 177 can accordingly aid in keeping the collar 171 at a target rotational position around the patient's neck. In other embodiments, other techniques can be used to provide this function, as will be described later.

The power transmission devices 179 can receive power from a power source 184 carried by the collar 171. The power source 184 can include one or more batteries. In some embodiments, the batteries are replaceable, e.g., by the user. In other embodiments, the batteries are re-chargeable, via an inductive charging coil 185, or a wired link (e.g., a mini-USB connection), and a corresponding charger 173 (shown in FIG. 4).

The collar 171 can further include a second substrate 178*b* that carries other elements of the wearable device circuitry 180. Such elements can include a processor 182, a memory 181, input/output devices 183, and/or other elements used to manage the process of transferring power from the power sources 184 to the power transmission devices 179, and/or perform other functions. Such functions can include receiving data from multiple sensors 190. The sensors 190 can be carried by any of the substrates 178 shown in FIG. 9, and/or can be located at other positions of the collar 171, independent of the substrates, as described further below with reference to FIG. 10B. The input/output devices 183 can include one or more data transmission/reception devices used to communicate data to/from the programmer 160, described above with reference to FIG. 4.

Figure 10A:
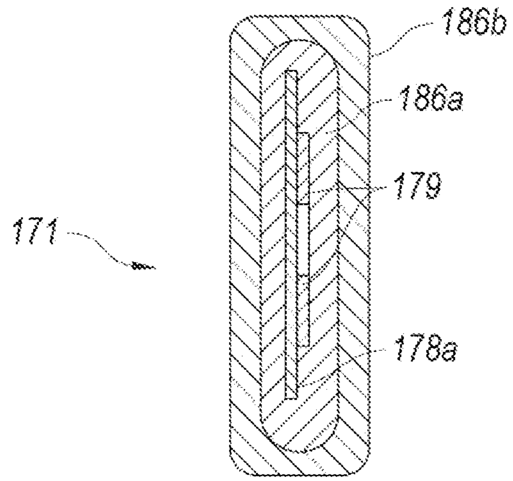
FIGS. 10A and 10B illustrate partially schematic cross-sectional views of the device shown in FIG. 9, taken generally along lines 10A-10A and 10B-10B, respectively, of FIG. 9.

FIG. 10A is a partially schematic, cross-sectional illustration of the collar 171, taken generally along line 10A-10A of FIG. 9. FIG. 10A illustrates the first substrate 178*a* carrying multiple power transmission devices 179. The collar 171 can further include a first layer 186*a* positioned around the first substrate 178*a*, and a second layer 186*b*, positioned around the first layer 186*a*. In particular embodiments, the first layer 186*a* can include a foam or other compressible material, and the second layer 186*b* can include a breathable fabric, for example, cotton or a suitable synthetic. In still further embodiments, the collar 171 can include a single material that provides both cushioning and breathability. In any of the foregoing embodiments, the first substrate 178*a*, the power transmission devices 179 and/or other circuit elements carried by the first substrate 178*a* can have a low profile, so as to be flexible, and so as not to project uncomfortably against the patient's skin. The first and/or second layers 186*a*, 186*b* can further provide cushioning and protection for both the circuit elements and the patient. In at least some embodiments, the collar 171 can include pockets into which the elements of the system fit, thus supporting a modular construction that can be used for collars of different sizes, and/or to allow components to be easily replaced, as needed or desired.

Figure 10B:
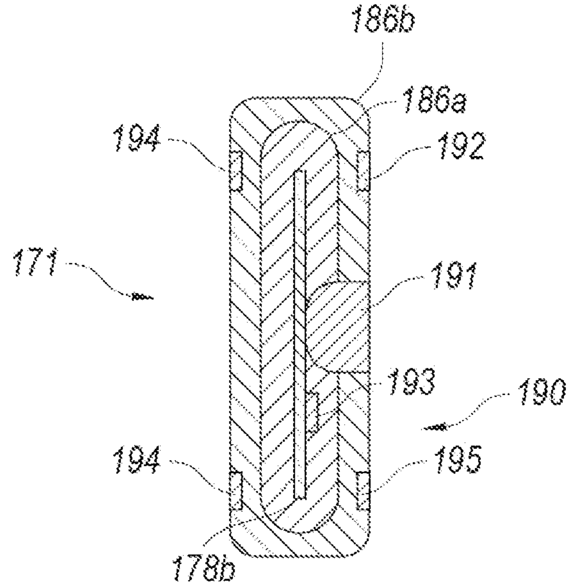

FIG. 10B is a partially schematic, cross-sectional illustration of the collar 171, taken generally along line 10B-10B of FIG. 9. FIG. 10B illustrates the second substrate 178*b*, as well as several sensors 190 that can be either carried by the second substrate 178*b*, or carried off the second substrate 178*b*. Representative sensors 190 include optical sources and optical signal detectors, for example, a photoplethysmography (PPG) sensor 191 that forms part of an $SPO_2$ oximetry sensor for sensing patient blood flow, heart rate, heart rate variability, respiratory rate, and oxygenation levels. In a particular embodiment, at least part of the PPG sensor 191 is positioned to contact the patient's skin, such as on the forehead and/or on or near (e.g., behind, below, etc.) the ear, to sense patient blood flow. Accordingly, the PPG sensor 191 can be located at a position within the collar 171 where it is in close proximity to the patient's jugular vein and/or carotid artery. The patient's $SPO_2$ values and/or changes in $SPO_2$ values over time can be used to determine the effectiveness of the therapy signal(s) applied to the patient P. For example, an increase in $SPO_2$ values can indicate that the therapy signal(s) is/are at least partially addressing the patient's sleep disorder, whereas constant or decreasing $SPO_2$ values can indicate that the therapy signal(s) are not addressing the patient's sleep disorder. As such, the patient's $SPO_2$ values can be used to adjust power transmission and/or one or more delivery parameters of the electrical signal generated by one or more of the implantable devices. In addition, the same optical sensor can detect the patient's respiration, which can then be used to determine when to deliver, modulate, and/or cease delivering the therapy signals to the patient. This feedback can accordingly be used to coordinate the resulting movement of the muscles in the patient's upper airway, with the patient's natural breathing cycles.

Other representative sensors 190 carried by the collar 171 can include one or more motion/orientation sensors 193 (e.g., accelerometers, tilt detectors, gyroscopes, inertial measurement units ("IMUs"), and/or the like) used to identify the motion and/or orientation of the patient while the patient is sleeping. This information can provide useful data for analyzing the effects of the system on the patient's sleep state and/or position, such as a position of the patient's body, head, and/or neck during sleep, and/or a change thereof. In at least some embodiments, the data received from the sensors 190 can be categorized based at least partially on the patient's sleep state (e.g., light vs deep, REM vs NREM) and/or sleep position (e.g., supine, left-side, right-side) to identify whether the patient's response to the therapy signal(s) differs based at least partially on the sleep state and/or the sleep position. For example, it is expected that the value of at least some of the signal delivery parameters (e.g., amplitude, frequency, etc.) associated with addressing or treating the patient's sleep disorder may vary based at least partially on the patient's sleep state and/or sleep position. Accordingly, these and/or other data can be used (e.g., by the wearable, 170, the programmer 160, and/or a practitioner) to adjust or optimize the signal delivery parameters of the therapy signal(s) delivered to the patient to address/treat the patient's sleep disorder when the patient's sleep state and/or sleep position changes (e.g., when the patient rolls over in their sleep).

The sensors 190 can further include and/or be configured to receive data associated with one or more of the following: inspiration cycle, expiration cycle, electroencephalography ("EEG"), electromyography ("EMG"), blood pressure, pulse transmit time ("PTT"), arterial tone (e.g., peripheral arterial tone ("PAT")), muscle tone, actigraphy, bioimpedance, pneumo-photoplethysmography, surgical pleth index, nociceptic analgesic index, bispectral index, and/or skin sympathetic nerve activity ("SKNA"), individual ones of which can be used to provide data for analyzing the effects of the system on the patient's sleep state and/or sleep position. In some embodiments, the wearable 170 can be configured to identify whether the patient is awake or asleep, in a REM sleep state versus an NREM sleep state, and/or a "light" sleep state versus a "deep" sleep state, based at least partially on data from one or more of the sensors 190 described herein. For example, an EMG sensor can be positioned on or near the patient's jaw and used to determine a muscle tone of one or more of the patient's jaw muscle. Continuing with this example, a reduction in jaw muscle tone (e.g., muscle laxity) can indicate that the patient is falling asleep and/or is sleeping. In these and other embodiments, a change in muscle tone associated with a patient's sleep state can occur in one or more muscles of the patient's neck, oral cavity, jaw, shoulder, and/or face, including any of the muscles described herein.

Other sensors can include one or more ECG electrodes 195 for identifying patient heartbeat, waveform, and/or arrythmias, thermal sensors 192 for identifying patient's skin temperature and/or body temperature, and one or more microphones 194. The microphone(s) 194 can be used to identify whether the patient is breathing through the nose and/or mouth, and/or when the patient is snoring and/or undergoing an apneic event. Additionally, or alternatively, the position/orientation of the patient's jaw can be measured using, for example, one or more EMG sensors, a force sensor, an optical measurement, etc., to identify whether the patient is breathing through the nose and/or mouth, and/or when the patient is snoring and/or undergoing an apneic event. In these and other embodiments, one or more of the sensors 190 can be configured to detect and/or measure a patient's respiratory effort. For example, respiratory inductance plethysmography ("RIP") is a method of evaluating pulmonary ventilation by measuring movement of the chest and/or abdominal wall, and can include one or more strain sensors and/or EMG sensors, e.g., positioned on or near the patient's chest and/or abdomen, such as by using a thorax belt to carry these sensors. As another example, one or more motion sensors can be positioned on or near the patient's neck (e.g., lower neck) and/or chest (e.g., upper chest) to detect movement associated with the patient's respiratory effort. Additionally, or alternatively, one or more mechanomyography ("MMG") sensors, EMG sensors, and/or strain sensors can be position on or near the patient's neck (e.g., lower neck) and/or chest (e.g., upper chest) to detect muscle activity associated with the patient's respiratory effort.

Any of the sensors 190 described herein can be used not only to record data for later analysis, but also to provide direct feedback that affects the stimulation provided to the patient. Accordingly, the power transmission device (FIG. 4) and the receiver device (FIGS. 5A-5C) can be configured to transmit data as well as power (as discussed above), or the system can include separate antennae (and/or other structures) to perform these functions. Additionally, in some embodiments the wearable device 170 includes a plurality (e.g., an array) of at least one of the sensors 190 described herein, and the data from the plurality of at least one of the sensors can be used to identify relative changes to the patient's anatomy, such as structural collapse in a first portion of the patient's oral tissue(s) versus structural collapse in a second portion of the patient's oral tissue(s). In a representative example, different structural collapse types can be associated with different characteristic audio feedback (e.g., breathing sounds, snoring sounds, etc.) and/or MMG frequencies that can be used to identify the type of collapse and/or the difference between the collapse in the first and second portions. In at least some embodiments, this relative data is used (e.g., by a practitioner, the wearable 170, and the programmer 160) to adjust the therapy signal(s) delivered to a portion of the patient's oral tissues. Continuing with the above example, if the first portion of the patient's oral tissue(s) are more collapsed relative to the second portion of the patient's oral tissue(s), the therapy signal(s) delivered to the first portion can be altered (e.g., relative to the therapy signal(s) delivered to the second portion) to reduce the collapse of the first portion of the patient's oral tissue(s). Additionally, or alternatively, data from a plurality of the same or different sensors can be used to locate (e.g., triangulate) one or more tissue collapse sites associated with patient apneic events.

Figure 11:
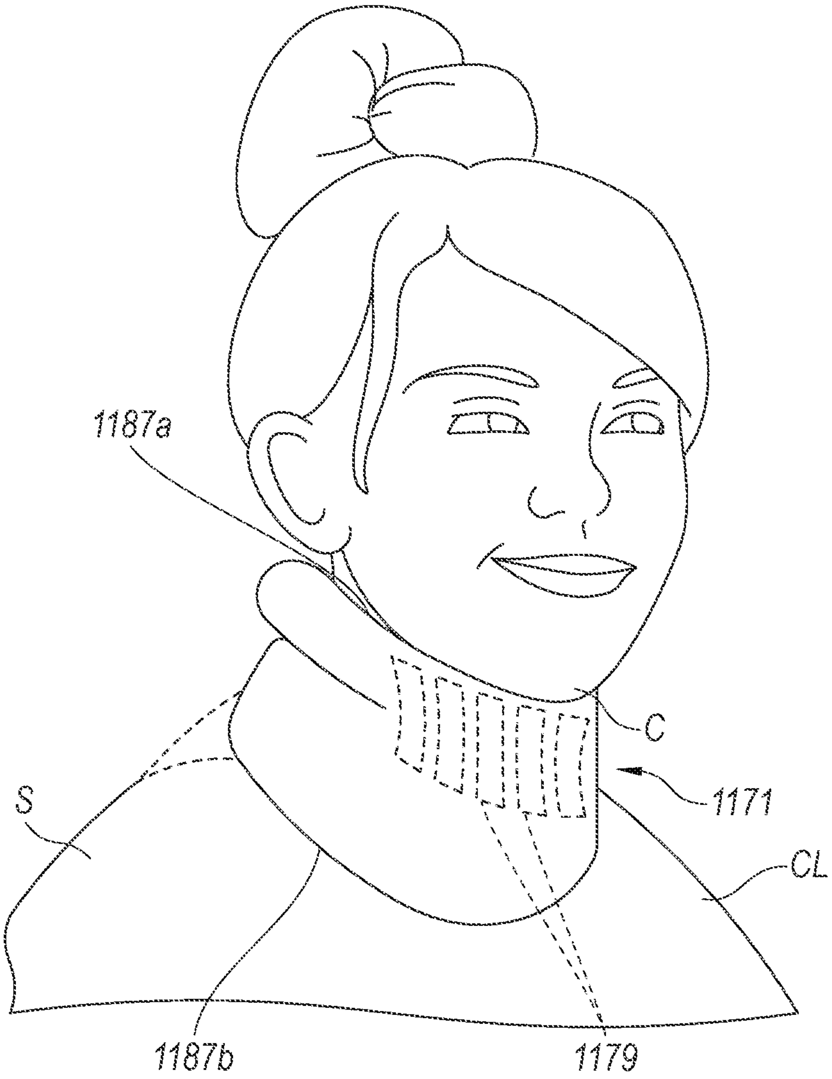
FIG. 11 is an illustration of a wearable device having a collar form factor configured to engage the patient's chin and shoulders, in accordance with representative embodiments of the present technology.

As indicated above, the collar 171 can include elements that aid in securing the collar in the correct position around the patient's neck. One such technique is to use the cutout 177 described above with reference to FIG. 9. FIG. 11 illustrates another representative technique. In this embodiment, a representative collar 1171 has an upper portion 1187*a* positioned to press gently upwardly against the patients chin C (and/or other portions of the lower jaw), and a lower portion 1187*b* positioned to press gently downwardly against the patient's shoulders S and/or clavicle CL. While this arrangement produces a collar having a larger form factor than the sweat-band form factor described above with reference to FIG. 9, it may be suitable for at least some patients, for example, patients whose tracheas do not extend anteriorly enough to fully engage with the cutout 177. In at least some embodiments, the collar 1171 can extend rearwardly or anteriorly over the patient's shoulder, as shown in dashed lines, to further aid in maintaining the collar's position. In addition to providing a secure position around the patient's neck, the collar 1171 can provide enough upward force on the patient's chin C to keep the patient's mouth closed while the patient sleeps, and therefore encourage the patient to breathe through their nose rather than their mouth. This in turn can reduce the likelihood for apneic events to occur as the patient sleeps.

The collar 1171 includes one or more power transmission devices 1179. In an embodiment shown in FIG. 11, the power transmission devices 1179 are arranged in an array and curve outwardly in an upward direction to conform the shape of the collar 171 and the patient's neck/jaw region. The conformal shape of the power transmission devices 1179 can produce one or more of several advantages. For example, the conformal shape can be more comfortable for the patient. The elongated, curved shape can efficiently deliver power both to implanted devices positioned in the jaw (e.g., to target the median branch of the hypoglossal nerve) and implanted devices positioned in the neck (e.g., to target the ansa cervicalis). In addition to or in lieu of the foregoing advantages, the curved shape of the power transmission devices 1179 can produce a broader field than can a planar device. In particular, while a planar device typically produces a focused, inwardly tapering conical field, the arcuate power transmission devices 1179 can produce an outwardly expanding field. This field can provide power to multiple implantable device at different locations, as discussed above, and/or can provide greater power transmission reliability in case the collar 1171 is not positioned precisely, and/or the collar moves relative to the patient as the patient stirs during sleep.

In other embodiments, any of the collars described above can have other features for securing the collar in position around the patient's neck. For example, the collars can include fabric earpieces that fit around the patient's ear, e.g., in the manner of a pair of glasses or a face mask. In still further embodiments, the collar can be clipped to the patient's hair, so long as doing so does not unnecessarily interfere with patient comfort.

Figure 12A:
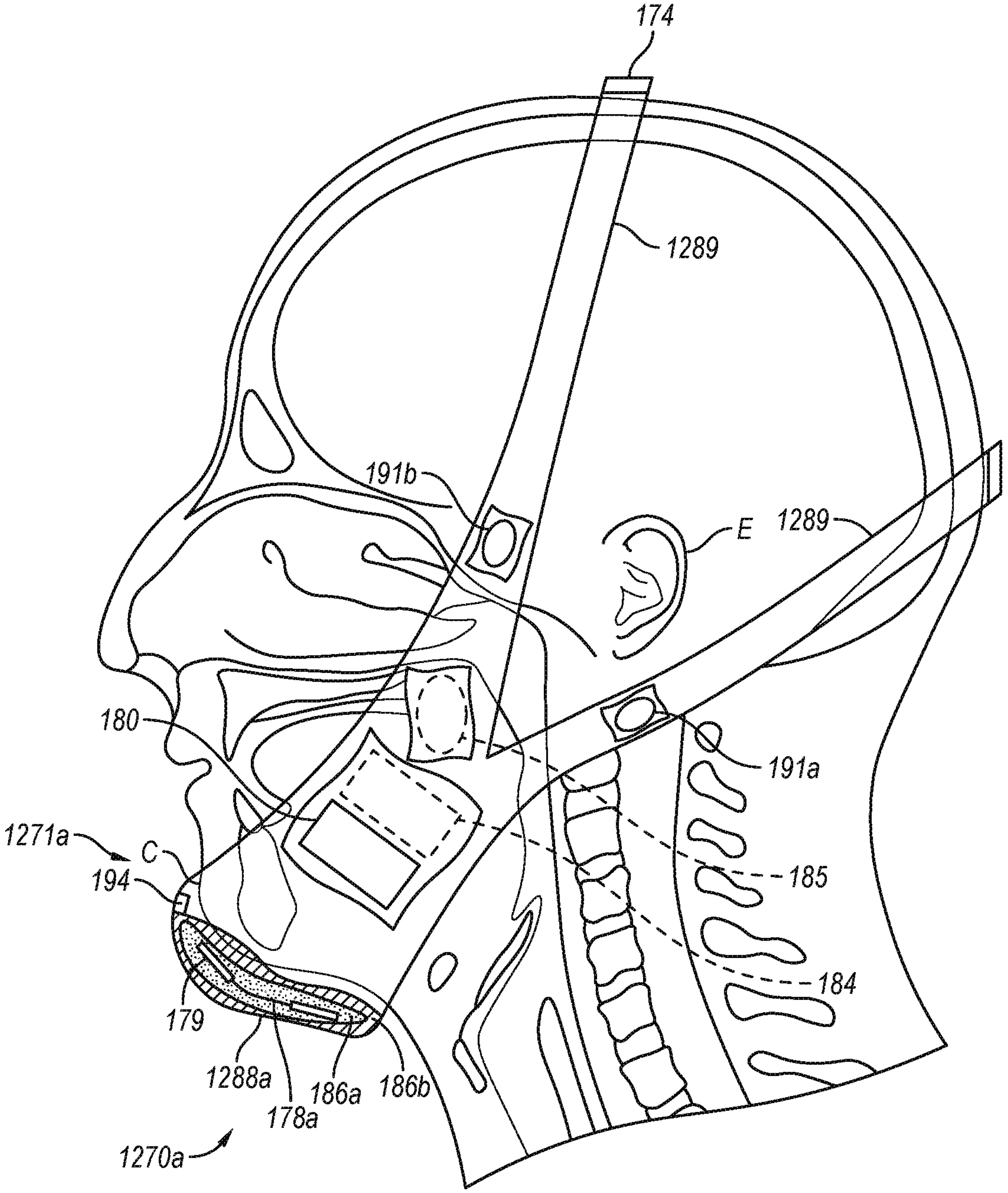
FIGS. 12A and 12B are partially schematic illustrations of respective wearable devices having a chin strap form factor, in accordance with embodiments of the present technology.

FIG. 12A is a partially schematic, partially cross-sectional, partially cut-away illustration of another wearable device 1270*a* having the form of a chin strap 1271*a*, in accordance with representative embodiments of the present technology. The chin strap 1271*a* can include a chin portion 1288*a* that fits around (e.g., cups) the patient's chin C, and one or more strap portions 1289 that fit around the top and/or back of the patient's head. The chin portion 1288*a* can house a first substrate 178*a* carrying one or more power transmission devices 179, generally in the fashion described above with reference to FIGS. 10A-B, and can accordingly include one or more conforming/protective layers, shown in cross-section in FIG. 12A as first and second layers 186*a*, 186*b*. The other elements described above with reference to the collar 171 shown in FIGS. 9-10B can also be carried by the chin strap 1271*a*. For example, the chin strap 1271*a* can include wearable device circuitry 180 at the part of chin portion 1288 positioned against the patient's left cheek. Other elements can be carried on the part of chin portion 1288*a* extending along the patient's right cheek. For example, a representative power source 184 and conductive coil 185 (both shown in dashed lines) can be located at such positions. One or more microphones 194 can be carried by the chin portion 1288*a*. One or more PPG sensors 191 (shown as a first PPG sensor 191*a* and the second PPG sensor 191*b*) can be carried by the chin portion 1288*a* or the strap portion 1289. For example, the first PPG sensor 191*a* is positioned just below the patient's ear E, and the second PPG sensor 191*b* is positioned at the patient's temple. In both embodiments, the PPG sensors are positioned at a portion of the patient's skin that is generally hairless, so as not to interfere with the sensing function carried out by these devices.

In particular embodiments, the one or more strap portions 1289 can be continuous, so that the patient can simply stretch the strap portion(s) 1289 over their head. In other embodiments, the strap portions 1289 can include detachable and re-attachable attachment portions 174, generally in the manner described above with reference to FIG. 9.

Figure 12B:
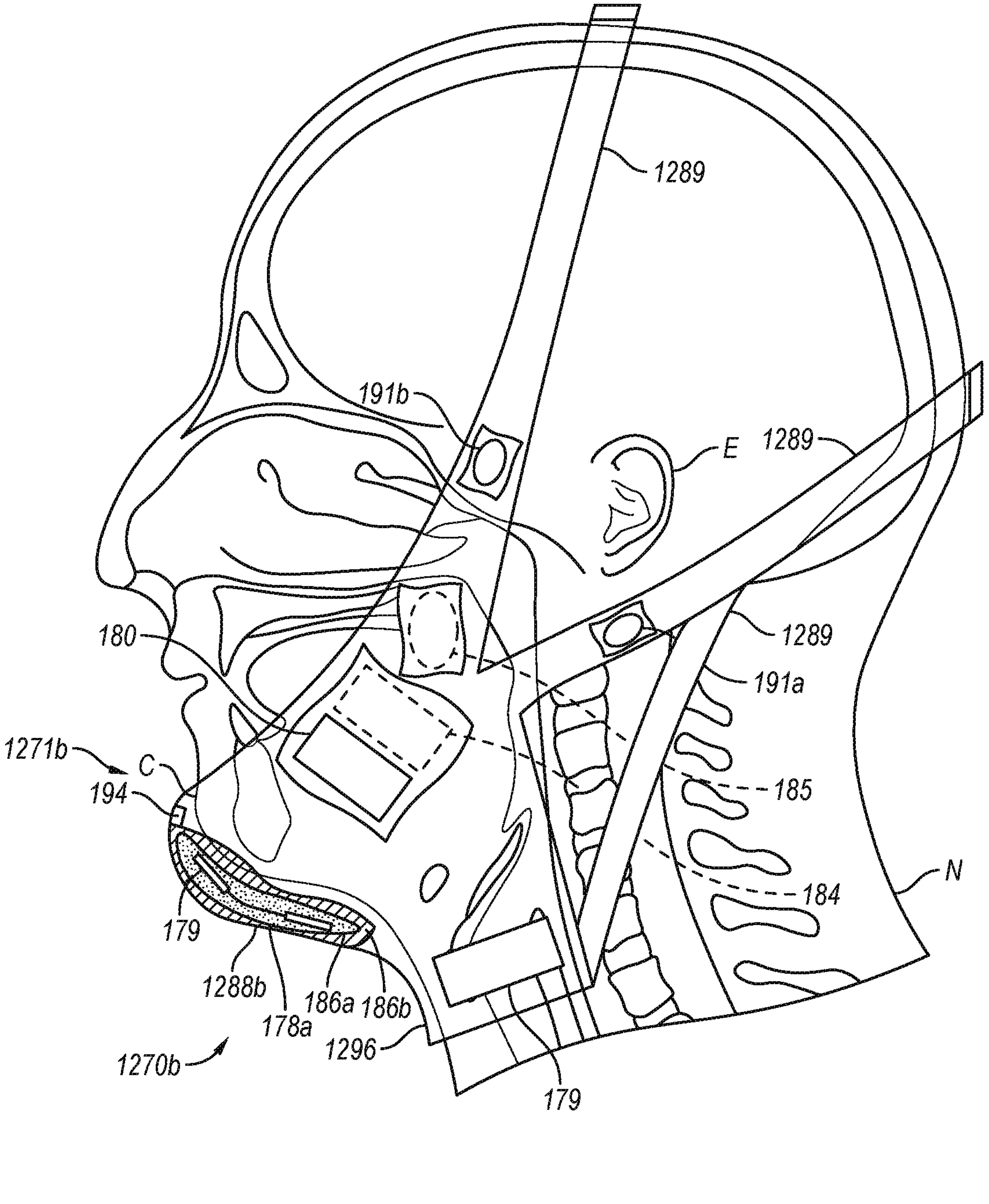

FIG. 12B is a partially schematic, partially cross-sectional, partially cut-away illustration of another wearable device 1270*b* having the form of a chin and neck strap 1271*b*, in accordance with representative embodiments of the present technology. At least some aspects of the wearable device 1270*b* can be generally similar or identical in structure and/or function to the wearable device 1270*a* of FIG. 12A. Accordingly, like names and/or references numbers (e.g., chin portion 1288*b* of FIG. 12B and the chin portion 1288*a* of FIG. 12A) are used to indicate generally similar or identical features. Additionally, the wearable device 1270*b* includes a neck portion 1296 inferior to the chin portion 1288*b* configured to fit at least partially around (e.g., cup) the patient's neck N. In the illustrated embodiment, the neck portion 1296 and the chin portion 1288*b* form a single-piece component, and the neck portion 1296 includes one or more of the straps 1289. In other embodiments, the neck portion 1296 can be detachably couplable to the chin portion 1288*b*.

The neck portion 1296 can include at least some elements of the wearable device 1270*b*. In the illustrated embodiment, for example, the neck portion 1296 carries a power transmission device 179 positioned to be aligned with one or more target signal delivery locations within the patient's neck N (e.g., the ansa cervicalis nerve). Accordingly, the power transmission device(s) 179 carried by the chin portion 1288*b* can be positioned to be aligned with one or more first target signal delivery locations at or near the patient's chin C (e.g., the HGN), and the power transmission device(s) 179 carried by the neck portion 1296 can be positioned to be aligned with one or more second target signal delivery locations at or near the patient's neck N (e.g., the ansa cervicalis), such that the wearable device 1270*b* can be configured to provide power to multiple implantable devices and/or to multiple locations within a patient. In these and other embodiments, the neck portion 1296 can include any of the other circuitry 180 of the wearable device 1270*b*, such as one or more of the substrate 178*a*, the layers 186*a-b*, the power source 184, the charging coil 185, the PPG sensors 191*a-b*, and/or the microphone 194.

In still further embodiments, the wearable device can have the form factor of a pillow, e.g., a bed pillow. For example, referring now to FIG. 13A, a representative wearable device 1370 includes a pillow 1371*a* on which the patient places his or her head while sleeping. In some embodiments, the pillow 1371*a* includes a cutout or notch 1377 having a V-shape or a U-shape configured to accommodate at least a portion of the patient's head H. The notch 1377 can accordingly aid in positioning the head H, the chin C, and/or the neck N relative to each other, such as to reduce movement of the patient's head H relative to the pillow and/or to align the patient's oral tissue(s) to at least partially reduce the onset of apneic events, e.g., even when the wearable device 1370 is not transmitting power. The pillow can carry multiple power sources 184, multiple power transmission devices 179, and corresponding substrates 178*a*, 178*b*. Sensors 190 can be carried by the substrates and/or can be positioned elsewhere on and/or in the pillow 1371*a*. In particular embodiments, the pillow 1371*a* can include more power transmission devices 179 than are used in either the collar 171 or the chin strap 1271, to account for the patient's movement while the patient sleeps. In particular embodiments, the system can include a proximity sensor (or other suitable device) to indicate if the patient has moved too far away from the nearest power transmission device. For example, the system can include a dedicated proximity sensor, or can use information transmitted by the implantable device and corresponding to the level of power received at the implantable device as an indication of the distance between the implantable device and the wearable device 1370. In particular embodiments, the system can emit a tone that changes in pitch (e.g., from low to high) as the patient moves closer to the power transmission device(s) 179 before going to sleep. Once the patient is asleep, the system can automatically direct power to the appropriate power transmission device(s) 179 to avoid waking the patient, as the patient moves about.

Figure 13A:
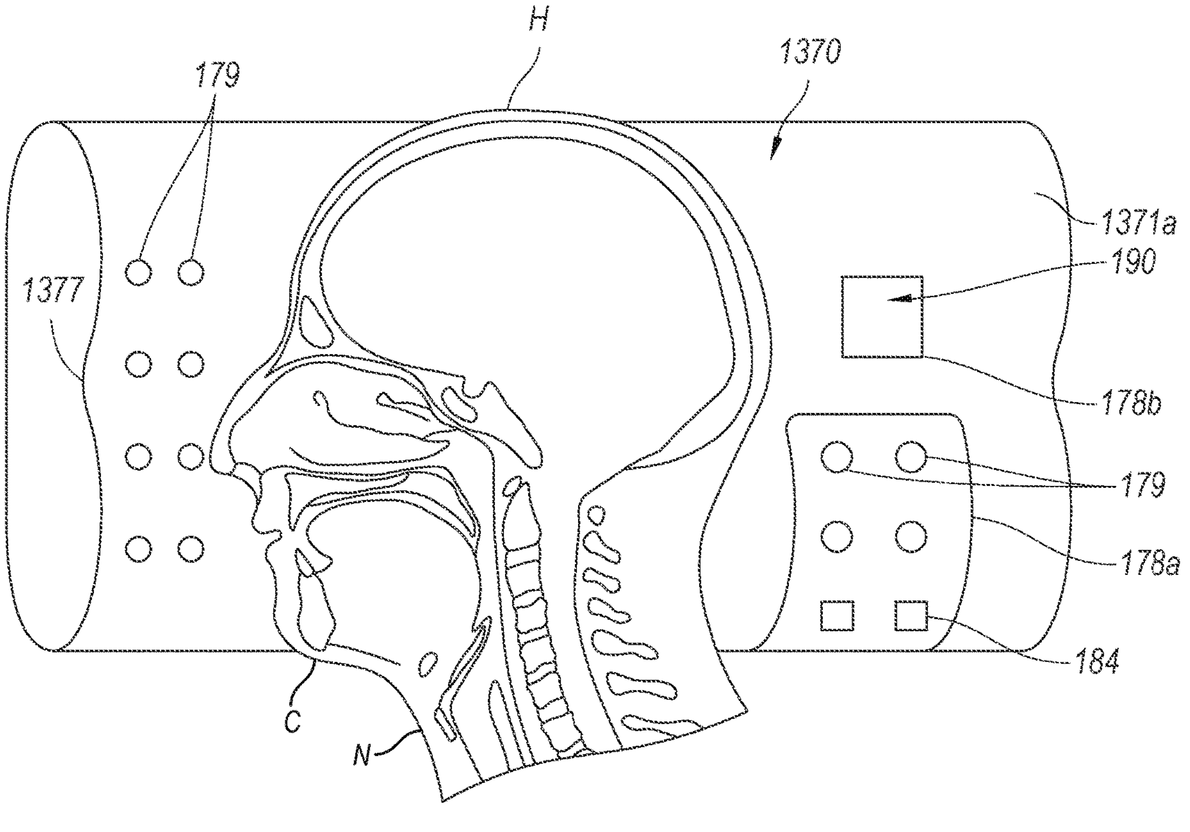
FIG. 13A is a partially schematic illustration of a wearable device having a pillow form factor in accordance with representative embodiments of the present technology.
Figure 13B:
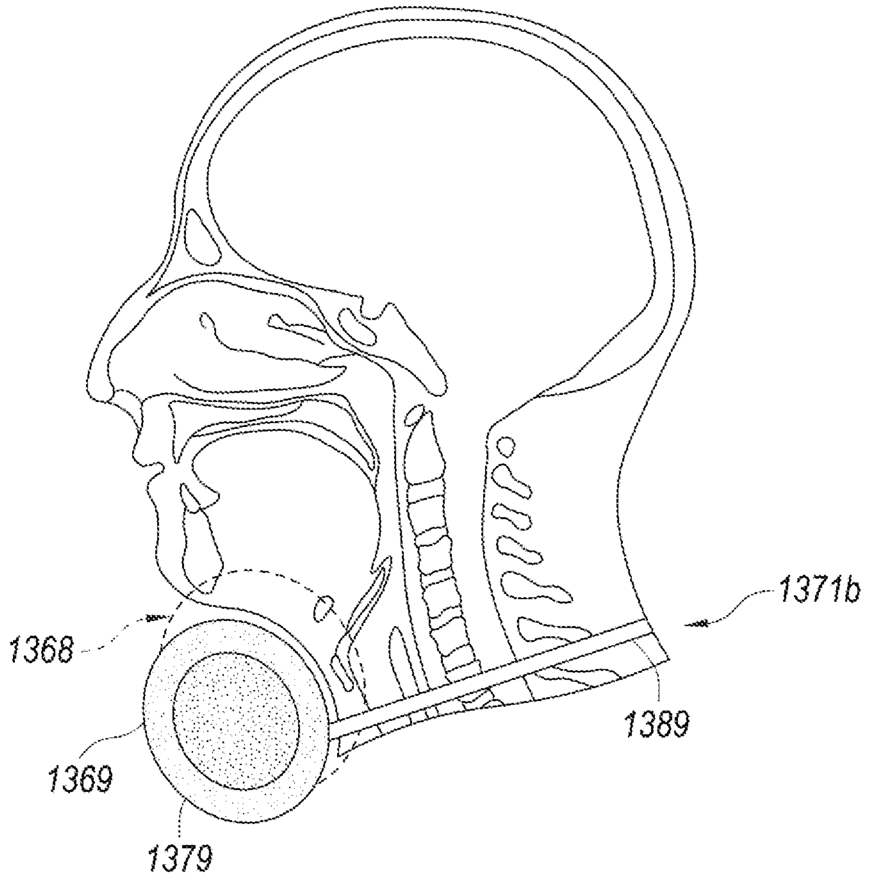
FIGS. 13B and 13C are partially schematic illustrations of a wearable device having a neck pillow form factor, in accordance with further embodiments of the present technology.
Figure 13C:
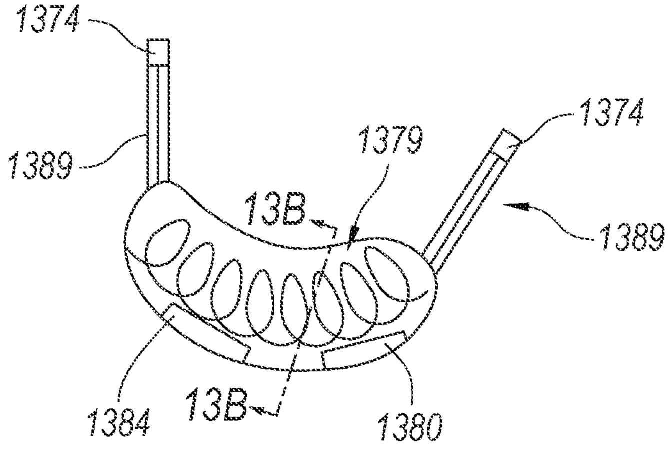

FIGS. 13B and 13C schematically illustrate another embodiment of a wearable device, having a configuration similar to that of a travel pillow, rather than a bed pillow. FIG. 13B is, in part, a cross-sectional view of the device shown in FIG. 13C, taken generally along line 13B-13B of FIG. 13C. The pillow 1371*b* can include a pillow portion 1369 secured around the patient's neck N with a strap portion 1389; the strap portion 1389 can include one or more attachment portions 1374 configured to couple to each other and secure the pillow portion 1369 around the patient's neck N. The pillow portion 1369 can have a cylindrical shape to accommodate a corresponding coiled power transmission device 1379. The power transmission device 1379 can generate an electric field 1368 having a shape generally extending upwardly into the patient's tissue at the patient's upper airway, as shown in FIG. 13B. The shape and position on the power transmission device 179 can be used to preferentially direct the field to the implantable devices at the patient's upper airway.

Referring now to FIG. 13C, the power transmission device 1379 can have an elongated coil-shaped configuration that generates a corresponding elongated electric field 1368, a cross-section of which was described above with reference to FIG. 13B. An advantage of the elongated electric field 1368, when compared to electric fields generated by the device described above, is that it may be broader, and therefore less likely to produce "holes" or other interruptions in power supply to the corresponding implanted signal delivery devices. Conversely, an advantage of the device configurations described above with reference to FIGS. 9-13A is that they may use less power than the device shown in FIGS. 13B and 13C.

In addition to the power transmission device 1379, the pillow 1371*b* can include the other elements described above with reference to suitable wearable devices, including circuitry 1380, a power source 1384, and sensors. For purposes of illustration, these additional components are not shown in FIGS. 13B or 13C, but are generally similar to those described above with reference to FIGS. 4-5C and 9-12.

Figure 13D:
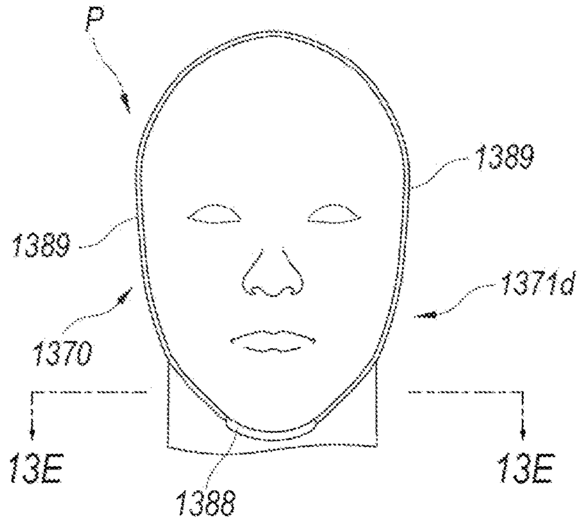
FIGS. 13D-13H are partially schematic illustrations of wearable devices having a chin strap form factor and power transmission devices with subwavelength structures, in accordance with embodiments of the present technology.

FIG. 13D is a partially schematic illustration of a patient P wearing a wearable device 1370 having the form of a chin strap 1371*d* configured in accordance with representative embodiments of the present technology. The chin strap 1371*d* can include one or more strap portions 1389 that secure a corresponding chin portion 1388 in position.

Figure 13E:
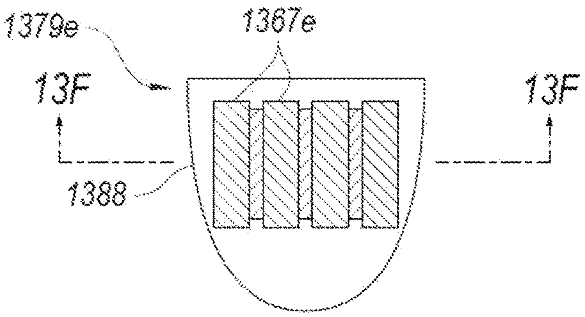

FIG. 13E is a partially schematic downward-looking view of the chin portion 1388, taken from the perspective of line 13E-13E of FIG. 13D. For purposes of illustration a conformal cover layer of the chin portion 1388 has been removed. As shown in FIG. 13E, the chin portion 1388 can carry at least one power transmission device 1379*e* that transmits power to an implantable device having any of the configurations described above. The power transmission device 1379*e* can include multiple subwavelength structures 1367*e* arranged in a pattern to produce the desired electric field (e.g., an evanescent field). In at least some embodiments, the subwavelength structures 1367*e* can be arranged to operate in a manner generally similar to that disclosed in U.S. Pat. No. 10,594,166. In other embodiments, however, the power transmission device 1379*e* can include other structures, such as whip and/or coil antennas.

Figure 13F:
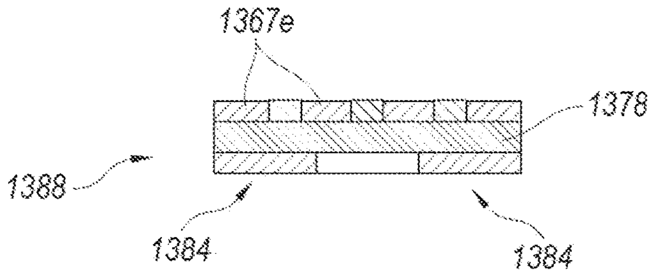

FIG. 13F is a partially schematic, cross-sectional view of the chin portion 1388, taken generally along line 13F-13F of FIG. 13E, with both the conformal cover layer and the conformal under layer removed. FIG. 13F illustrates a substrate 1378, which carries the subwavelength structures 1367*e*. The substrate 1378 can further carry one or more power sources 1384, e.g., a plurality of flat, re-chargeable batteries. The power sources 1384 are then coupled to the subwavelength structures 1367*e* via the substrate 1378. Similar to embodiments described above, the substrate 1378 (and the subwavelength structures 1367*e*) can be flexible so as to conform to the shape of the patient's jaw, chin, and/or neck.

Figure 13G:
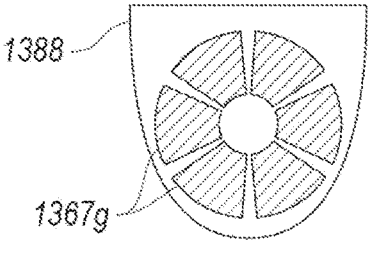
Figure 13H:
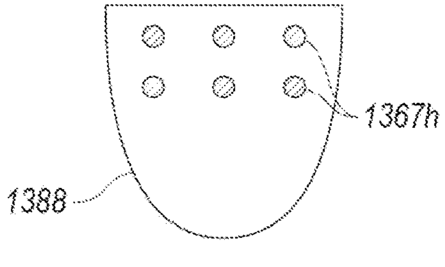

FIGS. 13G and 13H schematically illustrate chin portions 1388 having subwavelength structures 1367*g*, 1367*h*, respectively, arranged in patterns different than that shown in FIG. 13E. For example, in FIG. 13G, the subwavelength structures 1367*g* are arranged generally as pie-shaped sectors. In FIG. 13H, the subwavelength structures 1367*h* have generally circular shapes, and are arranged in a two-dimensional array. In other embodiments, the subwavelength structures can have other shapes and arrangements, depending upon patient physiology, the location of the corresponding implantable devices, and/or other factors.

Figure 14:
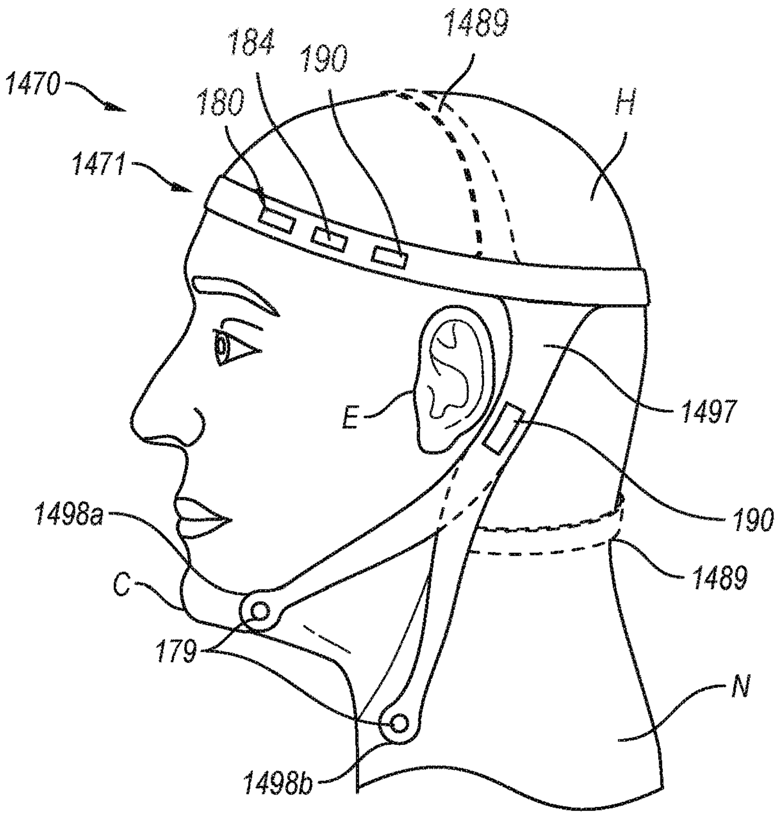
FIGS. 14-21 are partially schematic illustrations of wearable devices configured in accordance with embodiments of the present technology.

FIG. 14 is a partially-schematic side view of another wearable device 1470 configured in accordance with embodiments of the present technology. The wearable device 1470 includes a headband 1471 configured to extend at least partially around the patient's head H when worn. At least a portion of the headband 1471 can be elastic, deformable, rigid, and/or otherwise configured to reduce or prevent movement of the wearable device 1470 relative to the head H. In addition, the headband 1471 can include one or more straps 1489 configured to extend at least partially around the head H and/or the neck N to prevent or at least further reduce movement of the wearable device 1470. The headband 1471 can include the circuitry 180 and the power source 184. The headband 1471 can further include an ear portion 1497 configured to extend (e.g., downwardly) toward and/or past the patient's ear E. In the illustrated embodiment, the ear portion 1497 is positioned behind/posterior the ear E. In other embodiments, at least a portion of the ear portion 1497 can be positioned on, over and/or in front of/anterior to the ear E. The ear portion 1497 can carry one or more elements of the wearable device 1470. In the illustrated embodiment, for example, the ear portion 1497 carries one or more of the sensors 190, such as a motion sensors and/or an $SPO_2$ sensor. Additionally, or alternatively, one or more of the sensors 190 can be positioned at least partially around the patient's head H, such as on or near the forehead, as shown in FIG. 14.

The wearable device 1470 can further include one or more extension portions or arms 1498 (individually identified as a first arm 1498*a* and a second arm 1498*b* in FIG. 14). The arms 1498 can carry one or more of the power transmission devices 179, and can be adjustable, movable, or otherwise configured to be positioned at or near one or more target stimulation locations in the patient's chin C and/or neck N. The arms 1498 can include and/or be formed from a resilient and/or deformable material configured to allow a user to bend and/or otherwise set a position of one or more of the arms 1498 relative to the patient's chin C and/or neck N. In the illustrated embodiment, for example, the first arm 1498*a* is positioned so that the power transmission device 179 carried by the first arm 1498*a* can be positioned to transmit power to a first implantable device implanted at or near the patient's HGN (e.g., the medial branch MB of the HGN), and the second arm 1498*b* is positioned so that the power transmission device 179 carried by the second arm 1498*b* can be positioned to transmit power to a second implantable device implanted at or near the patient's ansa cervicalis AC. In other embodiments, one or both of the arms 1498 can have other suitable positions. In these and other embodiments, the arms 1498 of the wearable device 1470 are expected to improve power transmission to implantable devices at least because the positions of at least one of the arms 1498 can be adjusted to improve (e.g., optimize) alignment of the power transmission device(s) 179 with one or more of the implantable devices. In at least some embodiments, for example, one or more of the straps 1489 can be coupled to individual ones of the arms 1498 to at least partially prevent movement of the arms 1498 relative to the patient. In the illustrated embodiment, for example, the second arm 1498*b* is coupled to one of the straps 1489. Although the arms 1498 are shown on a left side of the patient's face in the illustrated embodiment, in these and other embodiments the wearable device 1470 can include one or more arms positioned on a right side of the patient's face.

Figure 15:
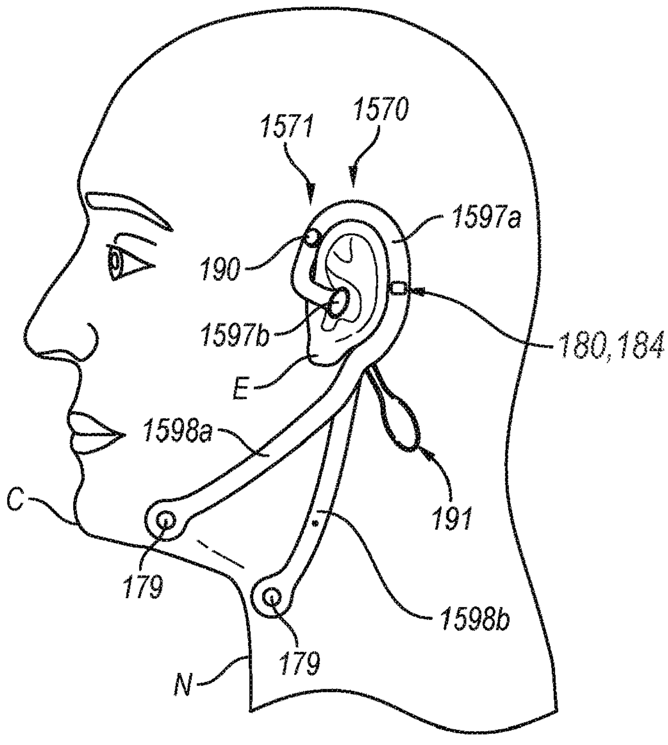

FIG. 15 is a partially schematic side view of another wearable device 1570 configured in accordance with embodiments of the present technology. The wearable device 1570 includes an earpiece 1571 configured to be worn at least partially around the patient's ear E. The earpiece 1571 can include a first earpiece portion 1597*a* configured to be positioned behind and/or extend at least partially over the top of the ear E. Optionally, the earpiece 1571 can include a second earpiece portion 1597*b* configured to be positioned at least partially within the ear E, e.g., within the concha and/or ear canal of the ear E. The earpiece further includes one or more extension portions or arms 1598 (individually identified as a first arm 1598*a* and a second arm 1598*b*) carrying one or more of the power transmission devices. The arms 1598 can be generally similar or identical in structure and/or function to the arms 1498 of FIG. 14; accordingly, the discussion of the arms 1498 with respect to FIG. 14 applies equally to the arms 1598 of FIG. 15. The earpiece 1571 can carry the elements of the wearable device 1570. In the illustrated embodiment, for example, the earpiece 1571 includes the circuitry 180, the power source 184, and one or more of the sensors 190. Optionally, the earpiece 1571 can include a PPG sensor 191 positioned at least partially behind the ear E. In these and other embodiments, the wearable device 1570 can include multiple earpieces, e.g., a first earpiece for a first (e.g., left) ear of the patient and a second earpiece for a second (e.g., right) ear of the patient.

Figure 16A:
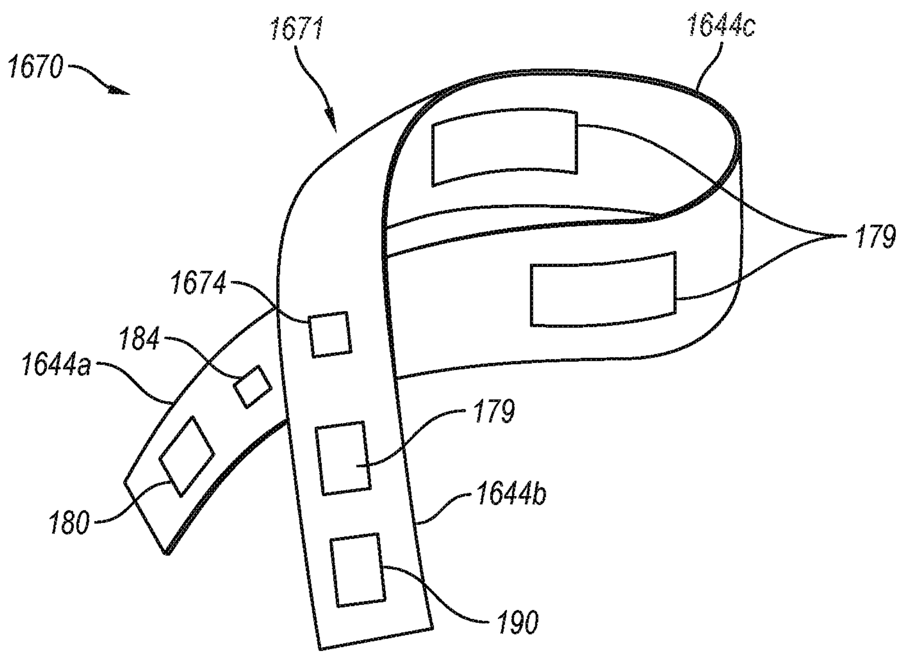
Figure 16B:
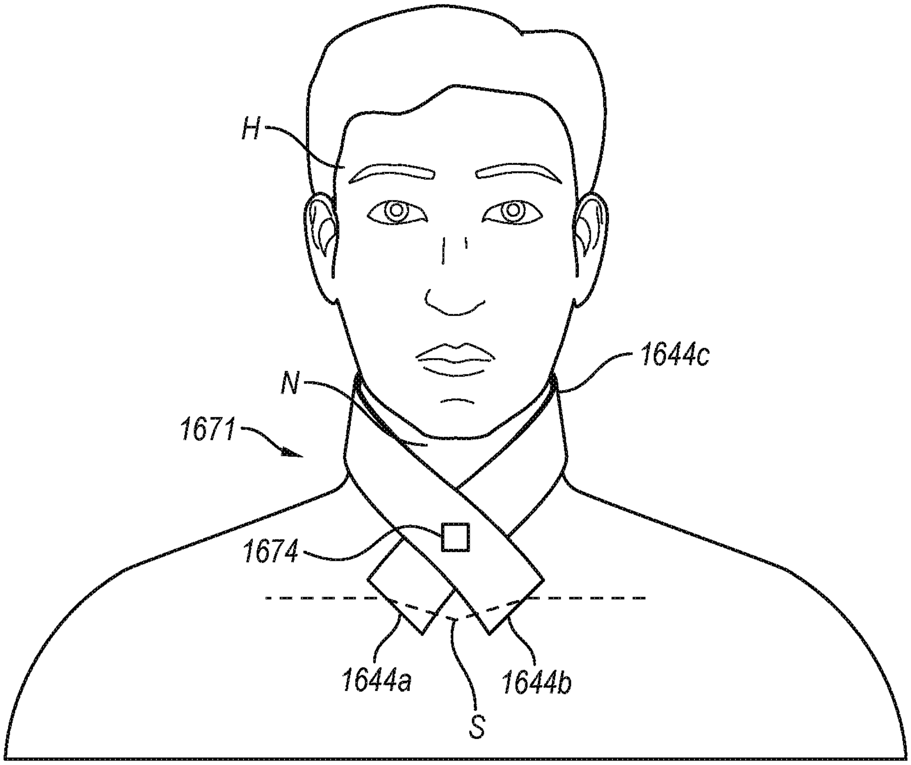

FIGS. 16A and 16B are partially schematic perspective and front views, respectively, or another wearable device 1670 configured in accordance with embodiments of the present technology. The wearable device 1670 includes a collar or neck-worn device 1671 which can have a scarf-like configuration. The collar 1671 includes a first end portion 1644*a*, a second end portion 1644*b*, and an intermediate or neck portion 1644*c* extending between the first end portion 1644*a* and the second end portion 1644*b*. When worn, the intermediate portion 1644*c* can be configured to extend at least partially around the patient's neck N and the first end portion 1644*a* and/or the second end portion 1644*b* can be configured to overlap each other and/or rest on the patient's chest, such as shown in FIG. 16B. In some embodiments, the first end portion 1644*a* and/or the second end portion 1644*b* can contact at least a portion of the patient's sternum S (shown in dashed line) when worn. The sternum S is generally expected to undergo little to no movement, for example, in response to movement of the patient's head H and/or neck N. Accordingly, positioning the first end portion 1644*a* and/or the second end portion 1644*b* to contact at least a portion of the patient's sternum S can reduce or prevent movement (e.g., rotational movement) of the wearable device 1670 relative to the patient. Additionally or alternatively, one or both of the first end portion 1644*a* and the second end portion 1644*b* can include one or more attachment features 1674 configured to (releasably) couple the first end portion 1644*a* to the second end portion 1644*b* and at least partially prevent (e.g., further prevent) movement of the wearable device 1670 relative to the patient. The attachment features 1674 can include one or more hook-and-loop portions, magnets, buttons, snaps, and/or any of the other attachment features described herein (e.g., with reference to FIG. 9).

Referring to FIG. 16A, one or more of the portions 1644*a-c* of the collar 1671 can carry the functional elements of the wearable device 1670. Generally, one or both of the end portions 1644*a-b* can include the circuitry 180, the power source 184, and/or the sensor(s) 190, and the intermediate portion 1644*c* can include the power transmission device(s) 179. In the illustrated embodiment, for example, the first end portion 1644*a* includes the circuitry 180 and the power source 184, the second end portion 1644*b* includes the sensor(s) 190, and the intermediate portion includes the power transmission devices 179. In other embodiments these and other elements of the wearable device 1670 can have other suitable positions. For example, in some embodiments the intermediate portion 1644*c* can include one or more of the sensors 190, and/or the first and/or second end portion 1644*a-b* can include one or more of the power transmission devices 179.

Figure 17A:
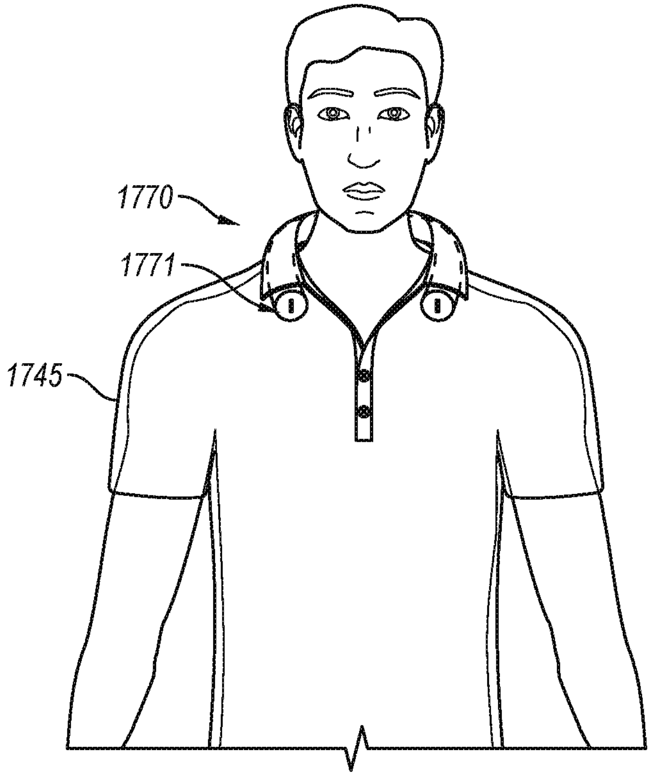
Figure 17B:
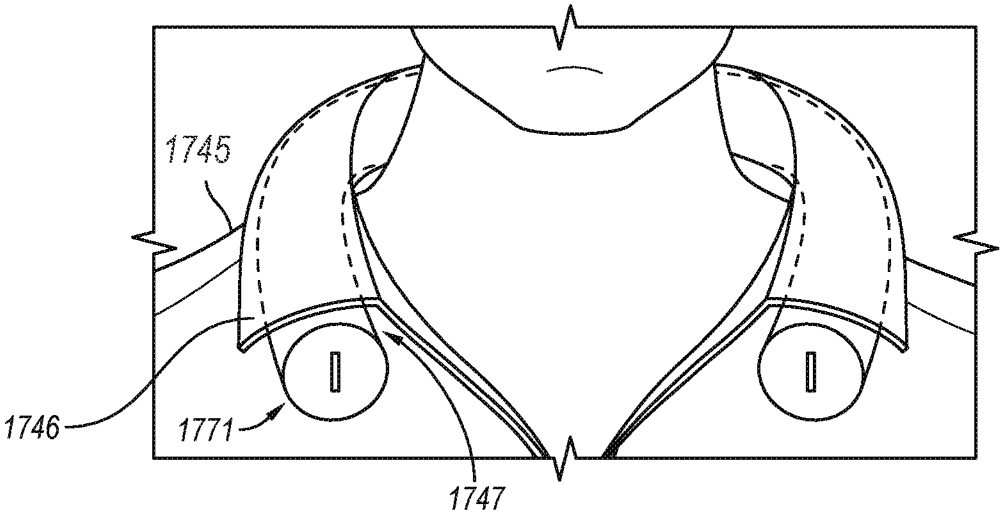

FIGS. 17A and 17B are partially-schematic front views of another wearable device 1770 configured in accordance with embodiments of the present technology. Referring to FIG. 17A, the wearable device 1770 includes a collar or other neck-worn wearable 1771 ("neck-worn wearable 1771") at least generally similar or identical in structure and/or function to the collar 171 of FIG. 9. In the illustrated embodiment, the neck-worn wearable 1771 extends partially around the patient's neck. In other embodiments, the neck-worn wearable 1771 can extend fully around the patient's neck. In these and other embodiments, the wearable device 1770 further includes a clothing article or garment 1745. In the illustrated embodiment, the garment 1745 includes a T-shirt or a polo shirt. In other embodiments, the garment 1745 can include a sweatshirt, a long-sleeve shirt, a tank top, a vest, a cropped shirt, or another suitable clothing article. Referring to FIG. 17B, the garment 1745 includes a collar portion 1746 defining a pocket or undercollar region 1747 configured to receive the neck-worn wearable 1771. In some embodiments, at least a portion of the undercollar region 1747 can be closed off by one or more buttons, zippers, magnets, etc. It is expected that combining the garment 1745 and the neck-worn wearable 1771 can at least partially reduce or prevent movement of the neck-worn wearable 1771 relative to the patient.

Figure 18:
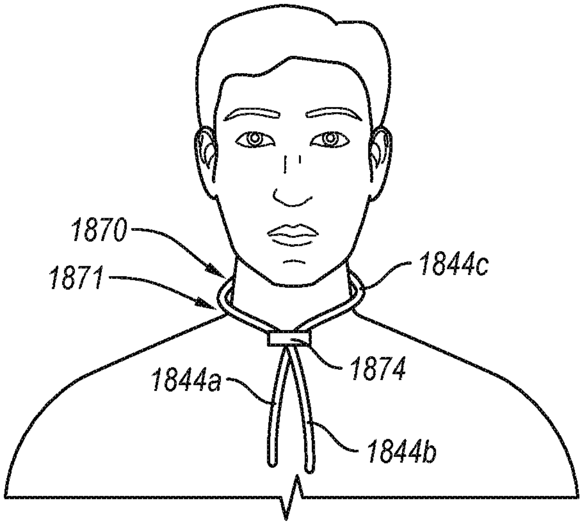

FIG. 18 is a partially-schematic front view of another wearable device 1870 configured in accordance with embodiments of the present technology. The wearable device 1870 includes a collar or other neck-worn wearable 1871 ("neck-worn wearable 1871"). At least some aspects of the neck-worn wearable 1871 can be generally similar or identical in structure and/or function to the collar 1671 of FIGS. 16A and 16B. However, the attachment feature 1874 can be a separate component, and at least part of the end portions 1844*a-b* and/or the intermediate portion 1844*c* of the neck-worn wearable 1871 can be positioned within and/or inserted through the attachment feature 1874, such that the neck-worn-wearable 1871 can have a bollo tie-like configuration. For example, the end portions 1844*a-b* and/or attachment feature 1874 can be moved relative to each other to loosen and/or tighten the fit of the neck-worn wearable 1871. In such embodiments, the attachment feature 1874, and/or one or more of the portions 1844*a-c* can carry the elements (e.g., circuitry, power transmission devices, sensors, etc.) of the neck-worn wearable.

Figure 19:
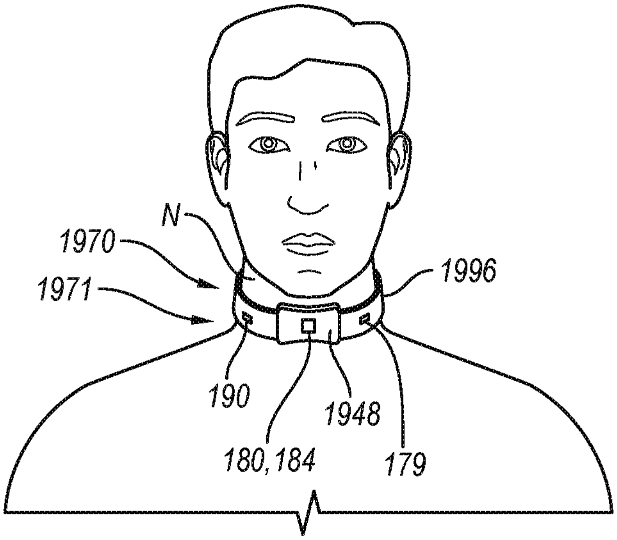

FIG. 19 is a partially schematic front view of another wearable device 1970 configured in accordance with embodiments of the present technology. The wearable device 1970 includes a collar 1971. At least some aspects of the collar 1971 can be generally similar or identical in structure and/or function to the collar 171 of FIG. 9. Additionally, the collar 1971 can include a casing or housing 1948 configured to contain at least some element of the wearable device 1970 (e.g., the circuitry 180, the power transmission device(s) 179, the sensor(s) 190, the power source 184, etc., described previously herein), and a neck portion 1996 coupled to one or more sides of the housing 1948 and configured to extend at least partially around the patient's neck N. Additionally, or alternatively, the neck portion 1996 can include one or more of the sensors 190 and/or power transmission devices 179. In some embodiments, the housing 1948 can be curved or otherwise configured to conform to the shape or a patient's neck N when worn, e.g., to reduce or prevent movement of the housing 1948 relative to the patient.

Figure 20:
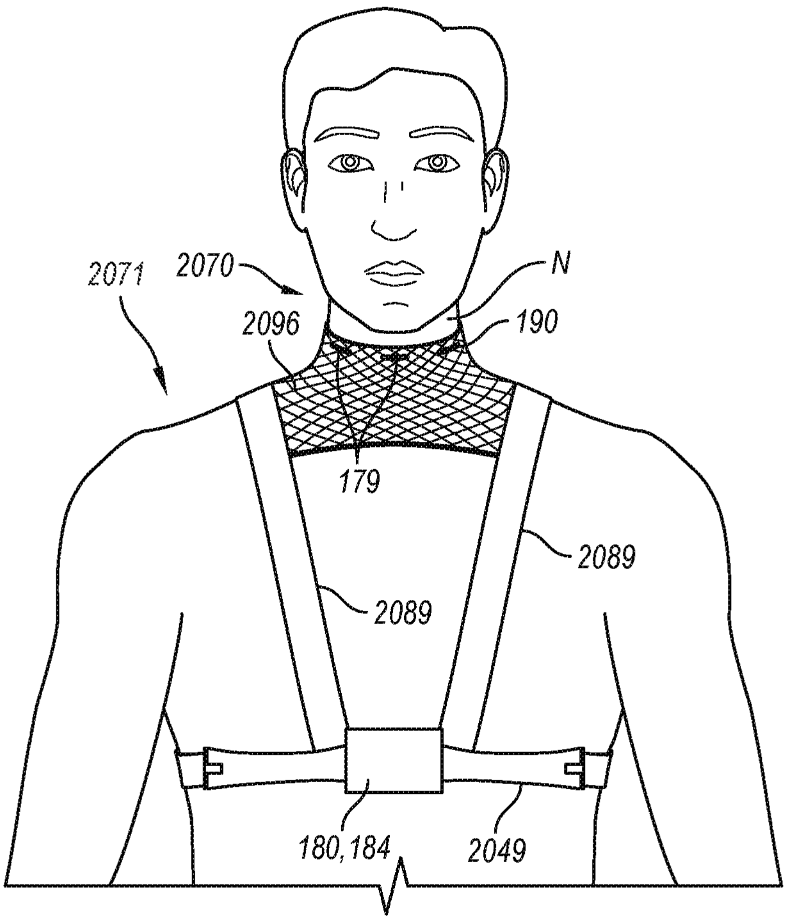

FIG. 20 is a partially schematic front view of another wearable device 2070 configured in accordance with embodiments of the present technology. The wearable device 2070 includes a vest or harness 2071 configured to be worn around at least a portion of the patient's torso/upper body. The harness 2071 can include a lower or chest portion 2049, an upper or neck portion 2096, and one or more strap portions 2089 extending between the chest portion 2049 and the neck portion 2096. The chest portion 2049 can include one or more straps configured to wrap around at least a portion of the patient's chest and/or the neck portion 2096 can be configured to wrap at least partially around the patient's neck N, such as shown in FIG. 20. In the illustrated embodiment, the neck portion 2096 includes the power transmission devices 179 and the sensor(s) 190 and the chest portion 2049 includes the circuitry 180 and the power source 184. Additionally, or alternatively, one or more of the strap portions 2089 can include the circuitry 180, the power source 184, one or more of the power transmission devices 179, one or more of the sensors 190, and/or other elements of the wearable device 2070. In at least some embodiments, for example, at least one of the strap portions 2089 can include a heart rate sensor positioned to be aligned with the patient's heart when the wearable device 2070 is worn. It is expected that combining the chest portion 2049 and/or the straps portion(s) 2089 can at least partially reduce or prevent movement of the neck portion 2096 relative to the patient.

Figure 21:
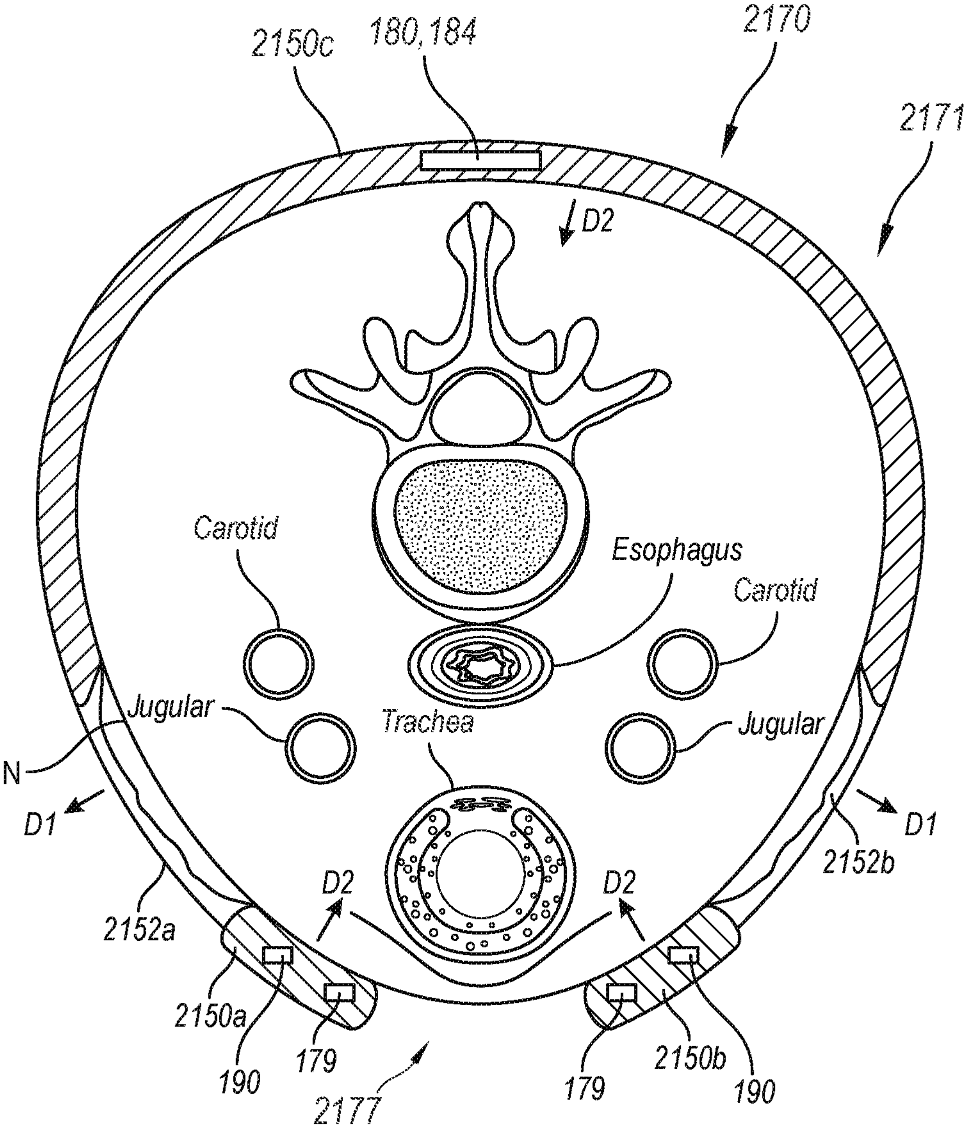

FIG. 21 is a partially schematic, cross-sectional top view of another wearable device 2170 and a portion of the patient's neck N anatomy, in accordance with embodiments of the present technology. The wearable device 2070 includes a collar or other neck-worn device 2171 configured to be worn at least partially around the neck N. At least some aspects of the neck-worn device 2171 can be generally similar or identical in structure and/or function to the collar 171 of FIG. 9. The neck-worn device 2171 can include one or more body portions 2150 (individually identified as a first body portion 2150*a*, a second body portion 2150*b*, and a third body portion 2150*c* in FIG. 21) configured to contact and/or press against the patient's neck, e.g., to secure the neck-worn device 2171 to the patient's neck N, and one or more relief portions 2152 (individually identified as a first relief portion 2152*a* and a second relief portion 2152*b* in FIG. 21) configured to be aligned with select portions of the patient's neck (e.g., the carotid, the jugular, the esophagus, etc.). Each of the relief portions 2152 can be positioned between two of the body portions 2150. In the illustrated embodiment, for example, the first relief portion 2152*a* is positioned between the first body portion 2150*a* and the third body portion 2150*c*, and the second relief portion 2152*b* is positioned between the third body portion 2150*c* and the second body portion 2150*b*. One or more of the body portions 2150 and/or the relief portions 2152 can be padded, e.g., to improve patient comfort.

The body portions 2150 can carry the circuitry 180 , power source 184, power transmission device(s) 179, sensor (s) 190, and/or other elements of the wearable device 2170. For example, the third body portion 2150*c* can include the power source 184 and the circuity 180, and the first and/or second body portions 2150*a-b* can include one or more of the sensors 190 and/or the power transmission antennas 179. In the illustrated embodiment, the relief portions 2152 are aligned with the patient's left and carotid artery and/or jugular vein, respectively. One or both of the relief portions 2152 can be spaced apart (e.g., not in contact with) the patient's neck N, and/or may not press against the patient's neck N. Additionally, or alternatively, the relief portions 2152 can be biased in a first direction D1 outwardly away from the patient's neck N, and/or the body portions 2150 can be biased in a second direction D2 opposite the first direction D1 and inwardly toward the patient's neck N. Accordingly, with continued reference to the illustrated embodiment, the body portions 2150 can secure the wearable device 2170 to the patient's neck N and the relief portions 2152 are not expected to alter or interrupt blood flow through the patient's neck N.

In some embodiments, the neck-worn device 2171 can have an open or horse-shoe shape defining a gap or opening 2177 such that the neck-worn device 2171 extends partially (e.g., not fully) around the patient's neck N. In the illustrated embodiment, for example, the opening 2177 is between the first and second body portions 2150*a-b* and can be aligned with a trachea of the patient when worn. Accordingly, the first and second body portions 2150*a-b* can be configured to "key" to or abut the trachea to at least partially reduce or prevent movement (e.g., rotational movement) of the neck-worn device 2171 when worn.

7. Representative Waveforms

Figure 22A:
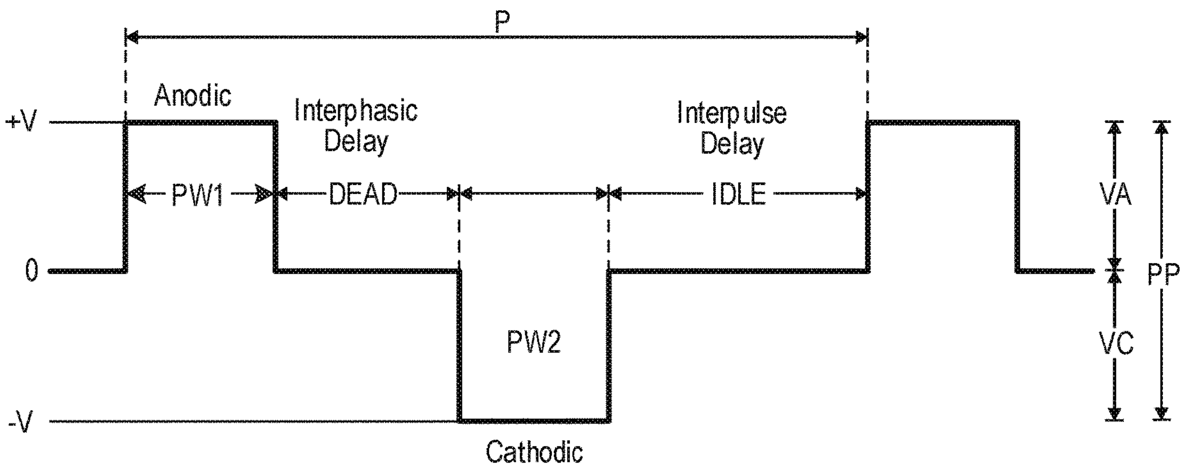
FIG. 22A is a representative example of a waveform having waveform parameters selected in accordance with embodiments of the present technology.
Figure 22B:
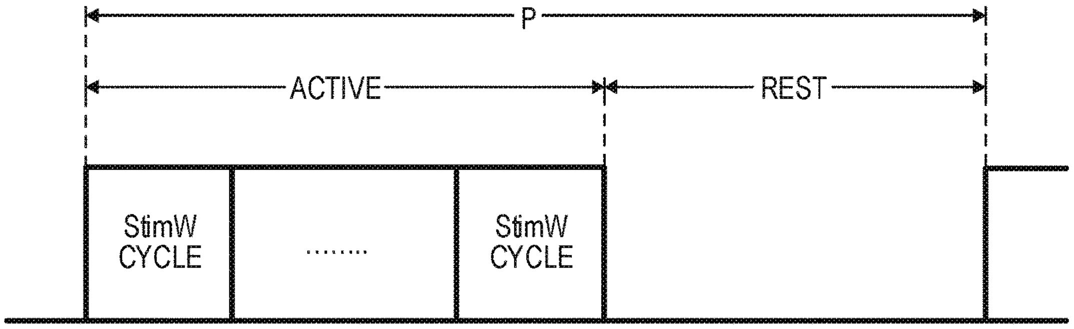
FIG. 22B is a representative example of a waveform having active and resting periods in accordance with embodiments of the present technology.

The signal generators and delivery devices described above can generate and deliver any of a variety of suitable electrical stimulation waveforms to modulate the actions of the patient's neurons and/or muscles. Representative examples are illustrated in FIGS. 22A and 22B and include a series of biphasic stimulation pulses that form stimulation wave cycles having a period as identified in FIGS. 22A and 22B. The waveform parameters can include active cycles and rest cycles. Each period P includes one or more pulses. The waveform shown in FIG. 22A comprises an anodic pulse followed by an interphasic delay, a cathodic pulse, and then an interpulse delay. Accordingly, the overall period P or cycle includes the following parameters: anodic pulse width (PW1), anodic amplitude (e.g., voltage or current amplitude VA), interphasic delay/dead time, cathodic pulse width (PW2), cathodic amplitude (e.g., voltage or current amplitude VC), interpulse delay/idle time, and peak-to-peak amplitude (PP). The parameters may also include the identity of the electrode(s) to which the signal is directed. The anodic pulse width (PW1) in some representative embodiments is between 30 μs and 300 μs. The anodic amplitude (VA) in some representative embodiments ranges from 1 mV to 5V, or 1 mA to 10 mA. The interphasic delay in some representative embodiments can be from 10 μs to 250 μs. The cathodic pulse width (PW1) in some representative embodiments is between 30 μs and 300μs. The cathodic amplitude (VA) in some representative embodiments ranges from 0.3V to 5V. In representative embodiments, the anodic and cathodic phases are charge balanced, though the phases need not be symmetrically shaped. The interpulse delay in some representative embodiments can be from 10 82 s to 100 μs. The peak-to-peak amplitude in some representative embodiments can be from about 2 mA to 12 mA. Representative frequencies range from about 10 Hz to about 500 Hz, such as from about 30 Hz to about 300 Hz in some embodiments, and up to 100 kHz (e.g., 10 kHz) in others. The pulses can be delivered continuously or in bursts. The frequency, the frequency range, the amplitude (e.g., peak-to-peak amplitude), the interpulse delay, the pulse width, and/or other signal delivery parameters can be varied based at least partially on the implanted location and/or the stimulation target of the implantable device. In some embodiments, multiple implantable devices are implanted in a patient, and each implantable device is configured to deliver a respective electrical signal having one or more respective signal delivery parameters. For example, a first implantable device implanted at a first location can be configured to deliver a first electrical signal having one or more first signal delivery parameters, a second implantable device implanted a second location can be configured to deliver a second electrical signal having one or more second delivery parameters, and individual ones of the first signal delivery parameters (e.g., amplitude, frequency, etc.) can be the same and/or different than individual ones of the second signal delivery parameters. Continuing with this example, the first electrical signal can include a first frequency and/or a first amplitude, the second electrical signal can include a second frequency and/or a second amplitude, and the first frequency can be the same or different than the second frequency and/or the first amplitude can be the same or different than the second amplitude. Additionally, as described previously herein, one of more of the signal delivery parameters can be adjusted (e.g., increased or decreased) or updated based at least partially on data associated with a patient sleep state, a patient sleep position, a patient apneic event, and/or a change thereof.

FIG. 22B illustrates a representative waveform comprising an active portion and a rest portion. The active portion includes one or more periods having the characteristics described above with reference to FIG. 22A. The rest portion has no stimulation pulses. According to some representative embodiments, the ratio of active portion to rest portion can be between 1:1 and 1:9. As a representative example, if the ratio is 1:9, and there are 300 active periods, there can be 2700 rest portions.

In a representative example, the stimulation voltage may be presented independently to each contact or electrode. For the positive pulse, the positive contact can be pulled to the drive voltage and the negative contact is pulled to ground. For the negative pulse, the negative contact can be pulled to the drive voltage and the positive contact is pulled to ground. For dead time and idle time, both contacts are driven to ground. For the rest time, both contacts are at a high impedance. To prevent DC current in the contacts, each half-bridge can be coupled to the contact through a capacitor, for example, a 100 μF capacitor. In addition, a resistor can be placed in series with each capacitor to limit the current in the case of a shorted contact. The pulses of the therapeutic waveform cycle may or may not be symmetric, but are generally shaped to provide a net-zero charge across the contacts.

Figure 23A:
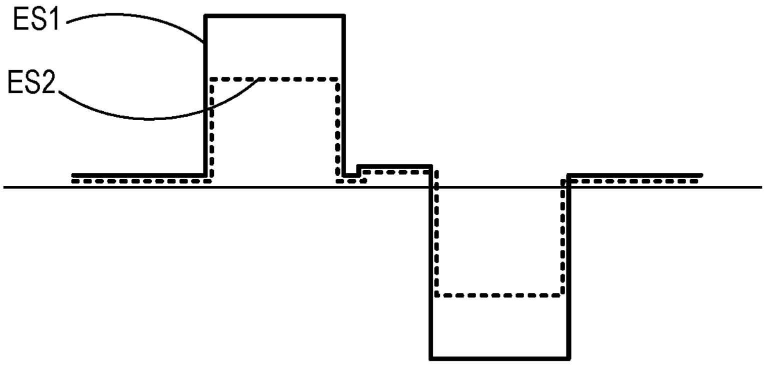
FIGS. 23A-24C are representative examples of waveforms in accordance with embodiments of the present technology.
Figure 23B:
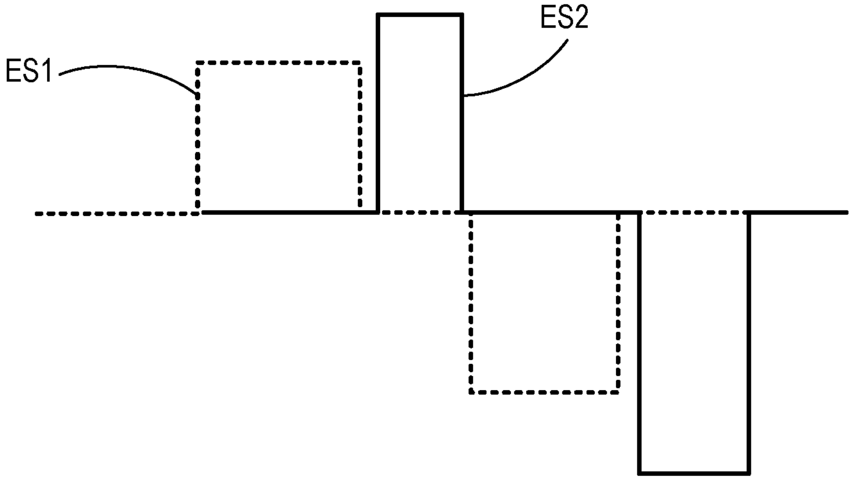
Figure 24A:
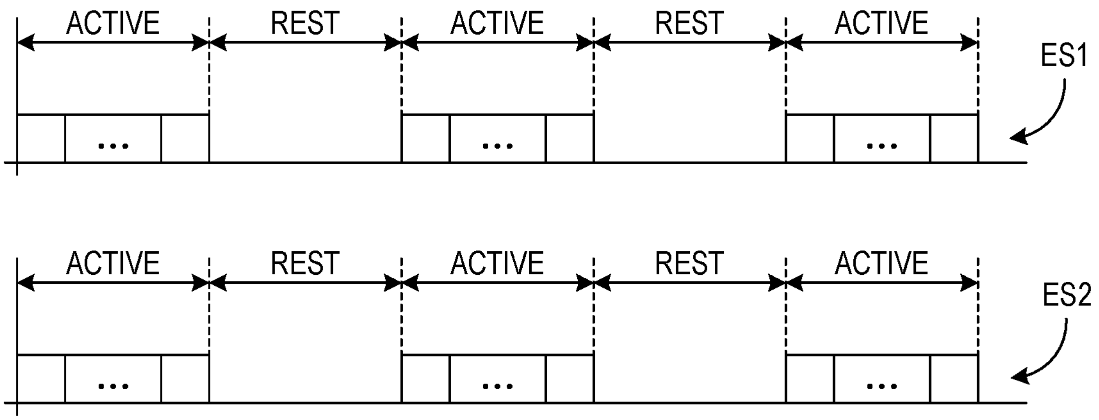
Figure 24B:
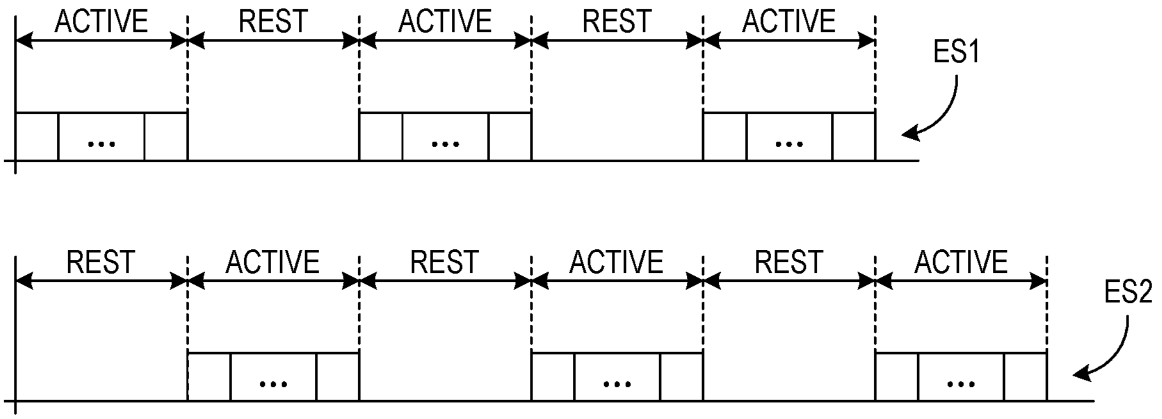
Figure 24C:
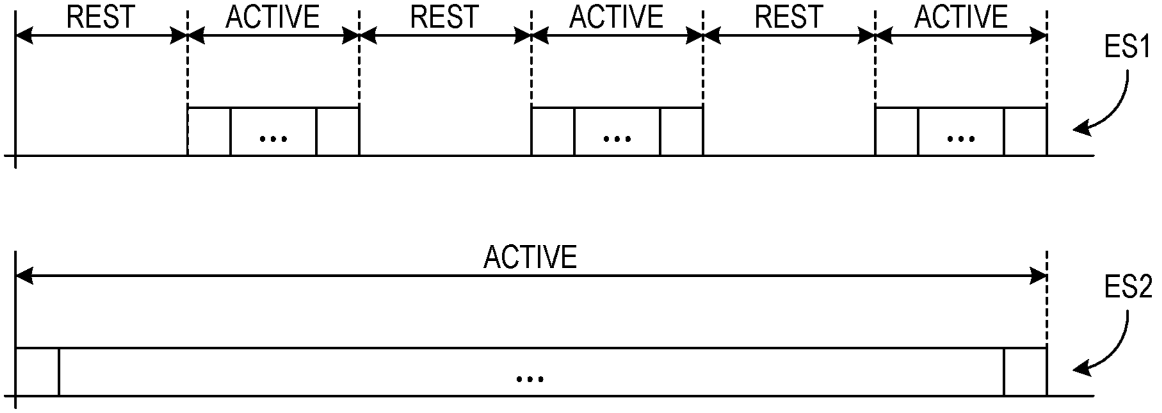

When multiple signals, such as a first electrical signal and a second electrical signal, are delivered to a patient (e.g., by multiple electrodes and/or multiple implantable devices), the first electrical signal and/or one or more portions thereof can be delivered at a same or different time as the second electrical signal and/or one or more portions thereof. For example, one or more individual pulses of a first electrical signal ES1 and a second electrical signal ES2 can be generated simultaneously (e.g., as shown in FIG. 23A), interleaved (e.g., as shown in FIG. 23B), and/or offset or overlapping, such that one or more of the individual pulses of the first and second electrical signals ES1, ES2 can be delivered at a same or different time. Additionally, or alternatively, individual ones of the active portions and/or the rest portions of the first electrical signal ES1 and the second electrical signal ES2 can be synchronous (e.g., occurring at a same time, such as shown in FIG. 24A), asynchronous or alternating (e.g., occurring at different times, such as shown in FIG. 24B), and/or at an offset or partially overlapping in time. Additionally, or alternatively, the active portions and/or the rest portions of the first and second electrical signals can have different time lengths. For example, one or more active portions and one or more rest portions of the first electrical signal ES1 can occur during a single active portion for the second electrical signal ES2 (e.g., as shown in FIG. 24C).

One feature of several embodiments of the systems described above is that the external wearable device, which carries the power source for the implantable device, is conformal. That is, the wearable device conforms, at least in part, to an individual patient's physiology. This feature is advantageous when compared to more rigid external devices because it is more comfortable for the patient to wear. This is turn is expected to produce higher patient compliance rates, and therefore improved patient outcomes, including a reduced number and/or severity of apneic events, and/or improved sleep quality.

Another feature of several embodiments of the systems described above is that they have a low profile, which facilitates patient comfort, and the ability to position the power transmission devices close to the patient's skin so as to transfer power efficiently to the implanted device(s) beneath the skin. An associated feature of several embodiments is that the implantable device provides distance between the system elements that deliver the therapy signals to the target location (e.g., the signal delivery electrodes), and the system elements that receive power from the wearable (e.g., the power receiver device). Accordingly, the electrodes can be positioned for improved (e.g., optimal) signal delivery, and the power receiver can be positioned for improved (e.g., optimal) power reception, with at least some degree of independence as to where each element is positioned.

While some embodiments may include elements or devices that are adhesively attached to the patient's skin, it is expected that avoiding temporary adhesives will provide further advantages. For example, embodiments that eliminate devices attached to the skin with temporary adhesives can simplify the process of using the wearable device, and the longevity of the device itself.

Yet a further feature of several embodiments of the present technology is that they include wearables specifically configured to be comfortably worn by the patient while sleeping. For example, the collar and chin strap form factors are expected to provide little or no resistance to the patient's natural movements directed to finding a comfortable sleeping position, while at the same time encouraging the patient to breathe through his or her mouth by gently restraining the jaw. The bed pillow form factor can present even less of an impediment, and the travel pillow form factor can provide an added measure of jaw motion restraint.

From the foregoing, it will be appreciated that specific embodiments of the disclosed technology have been described herein for purposes of illustration, but that various modifications may be made without deviating from the technology. For example, the power source and associated wearable device can have an intraoral mouthpiece configuration, that also delivers power wirelessly to one or more implanted electrodes. Further details are provided in co-pending U.S. application Ser. No. 17/749,025, filed on May 19, 2022, previously incorporated by reference herein, and U.S. application Ser. No. 17/518,414, filed Nov. 3, 2021, incorporated herein by reference.

Depending on the embodiment, the wearable device can include either a single power transmission device or multiple devices to supply power to any number of signal delivery devices positioned at the patient's head/neck region. For example, the wearable device can include a single power transmission device to power one or more signal delivery devices on one or both sides of the patient's lateral midline, or devices on both sides of the midline to do so. The particular arrangement of device(s) can depend on factors including the location of the implantable device in three dimensional space, including the depth beneath the patient's skin. An individual power transmission device can be formed as a unitary structure, or can be formed from multiple elements. For example, multiple smaller transmission elements can be arranged in an array to provide the desired electrical field for transmitting power to the implanted device(s).

In some embodiments, the components within the wearable device can be at least water-resistant, for example, to withstand moisture from the patient sweating. In other embodiments, the components can have different levels of water resistance or water-proof characteristics.

In some embodiments, the wearable device can include multiple microphones, to account for the directionality of an individual microphone, and/or to provide redundancy in case a microphone fails. Similarly, the wearable device can include one or more than one accelerometer to identify patient position. This information can be used to control the timing and/or other characteristics of the signal delivered to the patient. The accelerometer can also be used to determine whether the patient has properly placed the device on his/her body.

In general, the power transmission devices can emit conical radiation patterns, and in other embodiments, the radiation patterns may be shaped to fit particular patient physiologies and/or signal delivery implant locations. In at least some embodiments (for example, in the case of the wearable device including a pillow), the implanted signal delivery device can provide feedback to the wearable device if it is not receiving sufficient power. In response, the wearable device can increase the power provided to the implanted signal delivery device via the power transmission device.

Embodiments of the present technology can include wearable devices having configurations different than those expressly shown herein. For example, a collar-type wearable device can be integrated or integral with a night shirt (gown, pajamas, T shirt, and/or other clothing element), and not a separate item.

Certain aspects of the technology described in the context of particular embodiments may be combined or eliminated in other embodiments. For example, signal delivery devices having any of a variety of suitable configurations can be used with any one signal generator, and signal generators having any of a variety of suitable configurations can be used with any one signal delivery device. Further, while advantages associated with certain embodiments of the disclosed technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

As used herein, the phrase "and/or," as in "A" and/or "B" refers to A alone, B alone and both A and B. As used herein, the terms "about" and "approximately" refer to values within 10% of the stated value.

To the extent any materials incorporated herein by reference conflict with the present disclosure, the present disclosure controls.

The following examples provide additional representative features of the present technology.

EXAMPLES

1. A system for treating sleep apnea, comprising:
   - an implantable device implantably positionable at a patient's head and/or neck, proximate to the patient's oral cavity, the implantable device including:
     - a signal generator configured to generate a pulsed electrical signal, wherein at least a portion of the pulsed electrical signal has a first frequency in a first frequency range from about 10 Hz to about 500 Hz;
     - an electrode coupled to the signal generator to direct the electrical signal to the patient's tissue; and
     - a power receiver device coupled to the signal generator; and
   - a wearable device, including:
     - a power source; and
     - a power transmission device coupled to the power source and configured to transmit power wirelessly to the implantable device, wherein at least a portion of the power has a second frequency in a second frequency range from about 300 MHz to about 6 GHz.
2. The system of example 1 wherein the wearable device includes a collar configured to extend at least partially around the patient's neck.
3. The system of example 2 wherein the wearable device further includes a garment, and wherein the garment includes a pocket configured to receive the collar.
4. The system of example 3 wherein the garment includes a collar portion, and wherein the pocket includes an undercollar region defined at least partially by the collar portion.
5. The system of example 2 wherein the collar includes one or more body regions biased in a first direction toward the patient's neck and one or more relief region biased in a second direction away from the patient's neck.
6. The system of example 5 wherein an individual one of the one or more body regions is configured to contact the patient's neck, and wherein an individual one of the one or more relief regions is spaced apart from the patient's neck.
7. The system of example 5 wherein the individual one of the one or more relief regions is configured to be aligned with at least one of a vein or an artery within the patient's neck.

8. The system of example 2 wherein the collar includes a first end portion, a second end portion, and an intermediate portion between the first end portion and the second end portion, wherein
 the intermediate portion is configured to extend at least partially around the patient's neck, and
 the first end portion and the second end portion are configured to extend at least partially onto the patient's chest to at least partially prevent movement of the collar relative to the implantable device.
9. The system of example 8 wherein the first end portion and the second end portion include respective attachment features configured to releasably couple to each other when the first end portion and the second end portion are overlapped.
10. The system of example 1 wherein the wearable device includes a chin strap having a chin portion and a strap portion, wherein the chin portion includes at least one of the power transmission device and/or the power source, and wherein the strap portion is configured to extend at least partially around the patient's head.
11. The system of example 10 wherein the wearable device further includes a neck portion coupled to the chin portion and configured to extend at least partially around the patient's neck, wherein chin portion includes a first power transmission device, and wherein the neck portion includes a second power transmission device.
12. The system of example 10 wherein the strap portion includes an $SPO_2$ sensor positionable proximate the patient's ear.
13. The system of example 1 wherein the wearable device includes a headband configured to extend at least partially around the patient's head, wherein the headband includes an arm configured to extend toward the patient's chin and/or neck and carrying the power transmission device and a strap configured to wrap at least partially around the patient's head and/or neck to at least partially prevent movement of the arm relative to the patient.
14. The system of example 13 wherein the arm is a first arm and the power transmission device is a first power transmission device, the headband further comprising a second arm carrying a second power transmission device, wherein—
 the first arm is configured to position the first power transmission device at the patient's chin, and
 the second arm is configured to position the second power transmission device at the patient's neck.
15. The system of example 1 wherein the wearable device includes an earpiece configured to extend at least partially around the patient's ear, wherein the earpiece includes an arm configured to extend toward the patient's chin and/or neck and carrying the power transmission device.
16. The system of example 15 wherein the arm is a first arm and the power transmission device is a first power transmission device, the earpiece further comprising a second arm carrying a second power transmission device, wherein
 the first arm is configured to position the first power transmission device at the patient's chin, and
 the second arm is configured to position the second power transmission device at the patient's neck.
17. The system of example 1 wherein the wearable device includes a pillow having a notch shaped to conform to the patient's head and configured to support the patient's head in alignment with the patient's neck.
18. The system of any of examples 1-17 wherein the implantable device is a first implantable device implantably positionable at a first location at the patient's head and/or neck, the system further comprising a second implantable device implantably positionable at a second location, different than the first location, at the patient's head and/or neck, proximate to the patient's oral cavity, wherein the power transmission device is configured to transmit power to at least one of the first implantable device and/or the second implantable device.
19. The system of example 18 wherein the power transmission device is configured to move between a first position in which the power transmission device transmits the power to the first implantable device, and a second position in which the power transmission device transmits the power to the second implantable device.
20. The system of example 18 wherein the power transmission device is configured to transmit the power to the first implantable device at a first point in time and the second implantable device at a second point in time.
21. The system of any of examples 18-20 wherein the power transmission device is a first power transmission device configured to wirelessly transmit a first power signal to the first implantable device, the wearable device further comprising a second power transmission device coupled to the power source and configured to wirelessly transmit a second power signal to the second implantable device.
22. The system of any of examples 1-18 wherein the power transmission device is a first power transmission device configured to wirelessly transmit power to the implantable device at a first point in time, the wearable device further comprising a second power transmission device coupled to the power source and configured to wirelessly transmit power to the implantable device at a second point in time.
23. The system of any of examples 1-22 wherein the power transmission device is a first power transmission device configured to transmit power at a first power level, the wearable device further comprising a second power transmission device configured to transmit power at a second power level different than the first power level.
24. The system of example 23 wherein the implantable device is configured to: (i) at the first power level, communicate with the wearable device, and (ii) at the second power level, receive data via a sensor carried by the implantable device.
25. The system of example 23 or example 24 wherein the first power level is between about 0.01 W to about 0.05 W, and wherein the second power level is between about 0.1 W to about 0.3 W.
26. The system of example 23 or example 24, wherein the wearable device further comprises a third power transmission device configured to transmit power at a third power level different than at least one of the first power level or second power level, wherein the implantable device is configured to generate the pulse electrical signal at the third power level.
27. The system of example 26 wherein the third power level is between about 0.5 W to about 1 W.
28. The system of any of examples 1-27 wherein the power transmission device is configured to intermittently transmit power to the implantable device.

29. The system of example 28 wherein the wearable device includes one or more sensors configured to receive data associated with a patient sleep state and/or a patient apneic event, and wherein the power transmission device is configured to transmit the power based at least partially on the patient sleep state and/or the patient apneic event.
30. The system of example 29 wherein the one or more sensors includes both a heart rate sensor and an $SPO_2$ sensor.
31. The system of example 29 or example 30 wherein the one or more sensors include an electromyography sensor positioned to detect a muscle tone of one or more muscles in the patient's head, neck, face, and/or jaw.
32. A method of directing an electrical signal to a person, comprising:
    - programming a wearable device to
        - receive, via one or more sensors of the wearable device, data associated with at least one of a sleep state, a sleep position, or an apneic event of the person,
        - identify, based at least partially on the data, at least one of the sleep state, the sleep position, or the apneic event, and
        - transmit power based at least partially on the identified sleep state, sleep position, or apneic event, via a power transmission antenna of the wearable device positioned to be in wireless RF communication with a receiver antenna of an implantable device, wherein at least a portion of the power has a first frequency in a first frequency range from about 300 MHz to about 6 GHz; and
    - programming a pulse generator of the implantable device to
        - receive the power via the electrode receiver antenna; and
        - deliver, via at least one electrode of the implantable device positioned to be in electrical communication with a target location of the person, an electrical therapy signal, at least a portion of the electrical therapy signal having a second frequency in a second frequency range of up to 100 kHz.
33. The method of example 32 wherein programming the wearable device includes programming the wearable device to identify a change in at least one of the sleep state, the sleep position, or the apneic event; and wherein programming the pulse generator of the implantable device includes programming the pulse generator to change at least one signal delivery parameter of the electrical therapy signal based at least partially on the identified change in at least one of the sleep state, the sleep position, or the apneic event.
34. The method of example 32 or example 33 wherein programming the wearable device includes programming the wearable device to identify a change in at least one of the sleep state, the sleep position, or the apneic event; and wherein programming the pulse generator of the implantable device includes programming the wearable device to change at least one signal delivery parameter of the power based at least partially on the identified change in at least one of the sleep state, the sleep position, or the apneic event.
35. The method of any of examples 32-34 wherein the one or more sensors include at least one of a heart rate sensor, an $SPO_2$ sensor, a PPG sensor, an EEG sensor, an EMG sensor, a motion sensor, or an audio sensor.
36. The method of any of examples 32-35 wherein programming the wearable device includes programming the wearable device to transmit the power at a plurality of power levels, wherein each of the plurality of power levels is associated with a different operational state of the implantable device.
37. The method of any of examples 32-36 wherein the implantable device is a first implantable device, and wherein programming the wearable device includes:
    - programming the wearable device to transmit the power to the first implantable device via the power transmission device and at a first point in time; and
    - programming the wearable device to transmit the power to a second implantable device via the power transmission device and at a second point in time.
38. The method of any of examples 32-37, further comprising programming the implantable device to transmit, via a wireless transmission link with the wearable device, a power receipt verification to the wearable device in response to receiving the power via the electrode receiver antenna.
39. The method of any of examples 32-38 wherein the power transmission device is a first power transmission device, and wherein
    - programming the wearable device includes
        - programming the first power transmission device to transmit a first power signal, wherein at least a portion of the first power signal is at the first frequency, and
        - programming a second power transmission device of the wearable device to transmit a second power signal different than the first power signal, wherein at least a portion of the second power signal is at a third frequency different than the first frequency and within the first frequency range; and
    - programming the pulse generator includes programming the pulse generator to receive a third power signal different that the first power signal and the second power signal, wherein at least a portion of the third power signal is at a fourth frequency different that the first frequency and the third frequency.
40. The method of example 39 wherein the fourth frequency of the third power signal is a beat frequency resulting from the difference between the first frequency of the first power signal and the third frequency of the second power signal.
41. The method of example 39 or example 40 wherein the first frequency is 904 MHz and wherein the second frequency is 906 MHz.
42. The method of any of examples 39-41, further comprising programming the implantable device to communicate with the wearable device, including programming circuitry of the implantable device to modulate at least a portion of the third power signal and reflect the modulated portion of the third power signal to the wearable device.
43. A system for treating sleep apnea, comprising:
    - a first implantable device percutaneously positionable at a first location proximate a medial branch of a hypoglossal nerve of a patient, the first implantable device including
        - a first signal generator configured to generate a first electrical signal, wherein at least a portion of the first electrical signal has a first frequency in a first frequency range from about 10 Hz to about 500 Hz;

a first electrode coupled to the first signal generator to direct the first electrical signal to the medial branch; and a first power receiver device coupled to the first signal generator;

a second implantable device percutaneously positionable at a second location proximate an ansa cervicalis nerve of the patient, the second implantable device including a second signal generator configured to generate a second electrical signal, wherein at least a portion of the second electrical signal has a second frequency in a second frequency range from about 10 Hz to about 500 Hz;

a second electrode coupled to the second signal generator to direct the second electrical therapy signal to the ansa cervicalis; and a second power receiver device coupled to the second signal generator; and a wearable device including at least one of collar or a chinstrap, the wearable device including one or more sensors configured to detect at least one of a patient sleep state, a patient sleep position, or a patient apneic event, wherein the one or more sensors include a heart rate sensor, and $SPO_2$ sensor, and an EMG sensor;

a power source; and at least one power transmission device coupled to the power source and configured to transmit power wirelessly to at least one of the first implantable device or the second implantable device based at least partially on at least one of the patient sleep state, the patient sleep position, or the patient apneic event, wherein at least a portion of the power has a third frequency in a third frequency range from about 300 MHz to about 6 GHz.

44. The system of example 43 wherein the at least one power transmission device is configured to move between a first position in which the at least one power transmission device transmits the power to the first implantable device, and a second position in which the at least one power transmission device transmits the power to the second implantable device.

45. The system of example 43 or example 44 wherein the at least one power transmission device is configured to transmit the power to the first implantable device at a first point in time and the second implantable device at a second point in time.

46. The system of any of examples 43-45 wherein the at least one power transmission device includes at least one first power transmission device configured to wirelessly transmit power to at least one of the first implantable device or the second implantable device at a first point in time, the wearable device further comprising at least one second power transmission device coupled to the power source and configured to wirelessly transmit power to at least one of the first implantable device or the second implantable device at a second point in time.

47. The system of any of examples 43-46 wherein the at least one power transmission device is configured to intermittently transmit power to at least one of the first implantable device or the second implantable device.

48. The system of example 43-47 wherein the at least one power transmission device is configured to transmit power only in response to at least one of the patient sleep state, the patient sleep position, or the patient apneic event being detected.

49. The system of any of examples 43-48 wherein the one or more sensors are configured to detect a change in at least one of the patient sleep state, the patient sleep position, or the patient apneic event; and wherein the at least one power transmission device is configured to adjust transmission of at least one delivery parameter of the power based at least partially in response to the detected change in at least one of the patient sleep state, the patient sleep position, or the patient apneic event.

50. The system of any of examples 43-49 wherein the at least one power transmission device includes:

at least one first power transmission device configured to wirelessly transmit a first power signal having a first power level;

at least one second power transmission device coupled to the power source and configured to wirelessly transmit a second power signal having a second power level greater than the first power level; and at least one third power transmission device coupled to the power source and configured to wirelessly transmit a third power signal having a third power level greater than the second power level, wherein each of the first, second and third power levels are associated with a different operational state of at least one of the first implantable device or the second implantable device.

51. The system of example 50 wherein the first power level is between about 0.01 W to about 0.05 W, wherein the second power level is between about 0.1 W to about 0.3 W, and wherein the third power level is between about 0.5 W and about 1 W.

52. The system of any of examples 43-51 wherein the one or more sensors are configured to detect at least one of a patient supine sleep position, a patient side sleep position, a patient REM sleep state, a patient NREM sleep state, an obstructive apneic event, or a central apneic event.

53. The system of any of examples 43-52 wherein the wearable device includes a chin portion and a neck portion, and wherein the chin portion is configured to extend at least partially around the patient's chin and includes at least one first power transmission device positioned to transmit power to the first implantable device, and the neck portion is coupled to the chin portion, is configured to extend at least partially around the patient's neck, and includes at least one second power transmission device positioned to transmit power to the second implantable device.

We claim:

1. A system for addressing sleep apnea in a patient, the system comprising:

a wearable device including— a collar configured to be worn at least partially around a neck of the patient, the collar including— a first body portion having a first contact surface configured to be seated against a first anterior portion of the patient's neck to at least partially support the collar about the neck;

a second body portion having a second contact surface configured to be seated against a second anterior portion of the patient's neck to at least partially support the collar about the neck, wherein, when the collar is worn, the first body portion and the second body portion are biased in a first direction relative to the neck and are spaced apart to define an opening therebetween that is aligned with a trachea of the patient;

a third body portion extending at least partially between the first body portion and the second body portion and having a third contact surface configured to be seated against a posterior portion of the patient's neck to at least partially support the collar about the neck; and a relief portion coupling the first body portion to another portion of the collar, the relief portion biased in a second direction relative to the neck different than the first direction and including an innermost surface configured to face toward but be spaced apart from the neck when the collar is worn;

a first sensor coupled to the first body portion;

a second sensor coupled to the second body portion; and control circuitry coupled to the collar and configured to receive data from the first sensor and the second sensor and to generate, based at least in part on the received data, instructions for an implantable device configured to be positioned within the patient to deliver an electrical signal that addresses the patient's sleep apnea, wherein the instructions include instructions regarding the delivery of the electrical signal.

2. The system of claim 1 wherein the first and second body portions are configured to abut the patient's trachea to at least partially prevent movement of the wearable device relative to the patient's neck when worn.

3. The system of claim 1 wherein, when the wearable device is worn, the first body portion and the second body portion are configured to abut the patient's trachea to at least partially prevent rotational movement of the wearable device relative to the patient's neck.

4. The system of claim 1 wherein, when the wearable device is worn, no portion of the wearable device contacts the patient within the opening defined between the first body portion and the second body portion.

5. The system of claim 1 wherein the control circuitry is carried by the third body portion.

6. The system of claim 1 wherein, when the wearable device is worn, the first, second, and third body portions are configured to apply a compressive force to the patient's neck to securely seat the collar around the patient's neck.

7. The system of claim 1 wherein the first sensor includes an audio sensor and wherein the second sensor includes an SpO2 sensor.

8. The system of claim 1 wherein the collar further includes an orientation sensor, wherein the control circuitry is configured to determine a position or change to the position of the patient's body, head, and/or neck based at least in part on data from the orientation sensor, and wherein the instructions are further based at least in part on the determined position or change to the position of the patient's body, head, and/or neck.

9. The system of claim 1 wherein, based at least in part on the received data, the control circuitry is further configured to identify a structural collapse in a portion of the patient's oral tissues, and wherein the instructions are based at least in part on the identified structural collapse.

10. The system of claim 1 wherein, based at least in part on the received data, the control circuitry is further configured to compare a first identified structural collapse in a first portion of the patient's oral tissues with a second identified structural collapse in a second portion of the patient's oral tissues, and wherein the instructions are based at least in part on the comparison.

11. The system of claim 1 wherein the first body portion and/or the second body portion further include a power transmission device configured to wirelessly provide power to the implantable device.

12. The system of claim 11 wherein the power transmission device is further configured to transmit the instructions to the implantable device.

13. The system of claim 11 wherein, based at least in part on the received data, the control circuitry is further configured to:

determine that the patient is experiencing an apneic event, and in response to the determination, cause the power transmission device to transmit power to the implantable device.

14. The system of claim 11 wherein:

the power transmission device is configured to wirelessly provide power to the implantable device at multiple power levels, each of the multiple power levels associated with a different operating state of the implantable device; and the multiple power levels include a first power level configured to allow the implantable device to communicate with the wearable device and a second power level configured to allow the implantable device to deliver the electrical signal to the patient, the second power level greater than the first power level.

15. The system of claim 11 wherein the power transmission device includes an RF antenna.

16. The system of claim 11 wherein the power transmission device includes an inductive coil.

17. The system of claim 1 wherein the collar is configured to extend partially around the patient's neck when the wearable device is worn.

18. The system of claim 1, further comprising the implantable device, wherein the implantable device is configured to be positioned to deliver the electrical signal to a hypoglossal nerve of the patient or an ansa cervicalis nerve of the patient.

19. The system of claim 1 wherein:

the wearable device further includes— a first power transmission device operably coupled to the control circuitry and configured to transmit a first power signal at a first frequency, and a second power transmission device operably coupled to the control circuitry configured to transmit a second power signal at a second frequency different than the first frequency; and the control circuitry is further configured to cause the first and second power transmission devices to transmit the first and second power signals, respectively, at a same time to thereby cause the implantable device to wirelessly receive a third power signal at a third frequency equal to the difference between the first frequency and the second frequency.

* * * * *